(12) United States Patent
Brauker et al.

(10) Patent No.: US 10,022,078 B2
(45) Date of Patent: Jul. 17, 2018

(54) ANALYTE SENSOR

(75) Inventors: James H. Brauker, San Diego, CA (US); Peter C. Simpson, Encinitas, CA (US); Robert Boock, San Diego, CA (US); Monica Rixman, San Diego, CA (US); Mark Brister, Encinitas, CA (US)

(73) Assignee: DexCom, Inc., San Diego, CA (US)

( * ) Notice: Subject to any disclaimer, the term of this patent is extended or adjusted under 35 U.S.C. 154(b) by 199 days.

(21) Appl. No.: 11/439,630

(22) Filed: May 23, 2006

(65) Prior Publication Data

US 2006/0270923 A1    Nov. 30, 2006

Related U.S. Application Data

(63) Continuation-in-part of application No. 11/077,715, filed on Mar. 10, 2005, now Pat. No. 7,497,827.

(Continued)

(51) Int. Cl.
*A61B 5/1486* (2006.01)
*A61B 5/1473* (2006.01)
*G01N 33/66* (2006.01)
*A61B 5/145* (2006.01)
*A61B 5/00* (2006.01)

(Continued)

(52) U.S. Cl.
CPC ...... *A61B 5/14865* (2013.01); *A61B 5/14532* (2013.01); *A61B 5/411* (2013.01); *A61B 5/6848* (2013.01); *C12Q 1/006* (2013.01); *G01N 33/54366* (2013.01); *G01N 33/66* (2013.01); *A61B 5/1473* (2013.01); *A61B 5/418* (2013.01); *A61B 2562/08* (2013.01)

(58) Field of Classification Search
CPC . A61B 5/145; A61B 5/14503; A61B 5/14532; A61B 5/14546; A61B 5/1468; A61B 5/1473; A61B 5/14735; A61B 5/1477; A61B 5/1486; A61B 5/14865
USPC .............. 600/309, 345–366; 6/345, 347, 365
See application file for complete search history.

(56) References Cited

U.S. PATENT DOCUMENTS 1,564,641 A    12/1925  St. James
2,057,029 A    10/1936  Johnstone
(Continued)

FOREIGN PATENT DOCUMENTS

DE    4105222 A1    8/1992
DE    3933373 C2    9/1992
(Continued)

OTHER PUBLICATIONS

US 7,530,950, 05/2009, Brister et al. (withdrawn)
(Continued)

*Primary Examiner* — Navin Natnithithadha
(74) *Attorney, Agent, or Firm* — Knobbe Martens Olson & Bear, LLP

(57) ABSTRACT

The present invention relates generally to biointerface membranes utilized with implantable devices, such as devices for the detection of analyte concentrations in a biological sample. More particularly, the invention relates to novel biointerface membranes, to devices and implantable devices including these membranes, methods for forming the biointerface membranes on or around the implantable devices, and to methods for monitoring glucose levels in a biological fluid sample using an implantable analyte detection device.

13 Claims, 14 Drawing Sheets

Related U.S. Application Data

(60) Provisional application No. 60/683,923, filed on May 23, 2005, provisional application No. 60/614,764, filed on Sep. 30, 2004, provisional application No. 60/614,683, filed on Sep. 30, 2004, provisional application No. 60/587,800, filed on Jul. 13, 2004, provisional application No. 60/587,787, filed on Jul. 13, 2004.

(51) Int. Cl.
*C12Q 1/00* (2006.01)
*G01N 33/543* (2006.01)

(56) References Cited

U.S. PATENT DOCUMENTS

| | | |
|---|---|---|
| 2,402,306 A | 6/1946 | Turkel |
| 2,719,797 A | 10/1955 | Rosenblatt et al. |
| 3,210,578 A | 10/1965 | Sherer |
| 3,652,475 A | 3/1972 | Wada et al. |
| 3,728,678 A | 4/1973 | Tong |
| 3,775,182 A | 11/1973 | Patton et al. |
| 3,780,727 A | 12/1973 | King |
| 3,791,871 A | 2/1974 | Rowley |
| 3,826,244 A | 7/1974 | Salcman et al. |
| 3,838,033 A | 9/1974 | Mindt et al. |
| 3,898,984 A | 8/1975 | Mandel et al. |
| 3,926,760 A | 12/1975 | Allen et al. |
| 3,933,593 A | 1/1976 | Sternberg |
| 3,943,918 A | 3/1976 | Lewis |
| 3,957,613 A | 5/1976 | Macur |
| 3,957,651 A | 5/1976 | Kesting |
| 3,964,974 A | 6/1976 | Banauch et al. |
| 3,966,580 A | 6/1976 | Janata et al. |
| 3,982,530 A | 9/1976 | Storch |
| 4,003,621 A | 1/1977 | Lamp |
| 4,024,312 A | 5/1977 | Korpman |
| 4,036,749 A | 7/1977 | Anderson |
| 4,037,563 A | 7/1977 | Pflueger et al. |
| 4,040,908 A | 8/1977 | Clark, Jr. |
| 4,052,754 A | 10/1977 | Homsy |
| 4,067,322 A | 1/1978 | Johnson |
| 4,068,660 A | 1/1978 | Beck |
| 4,073,713 A | 2/1978 | Newman |
| 4,076,656 A | 2/1978 | White et al. |
| 4,116,920 A | 9/1978 | Honma et al. |
| 4,172,770 A | 10/1979 | Semersky et al. |
| 4,187,390 A | 2/1980 | Gore |
| 4,197,840 A | 4/1980 | Beck et al. |
| 4,215,703 A | 8/1980 | Willson |
| 4,225,410 A | 9/1980 | Pace |
| 4,240,889 A | 12/1980 | Yoda et al. |
| 4,253,469 A | 3/1981 | Aslan |
| 4,255,500 A | 3/1981 | Hooke |
| 4,259,540 A | 3/1981 | Sabia |
| 4,260,725 A | 4/1981 | Keogh et al. |
| 4,260,726 A | 4/1981 | Keogh et al. |
| 4,319,578 A | 3/1982 | Enger |
| 4,327,725 A | 5/1982 | Cortese et al. |
| 4,353,888 A | 10/1982 | Sefton |
| 4,374,013 A | 2/1983 | Enfors |
| 4,378,016 A | 3/1983 | Loeb |
| 4,388,166 A | 6/1983 | Suzuki et al. |
| 4,402,694 A | 9/1983 | Ash et al. |
| 4,403,847 A | 9/1983 | Chrestensen |
| 4,403,984 A | 9/1983 | Ash et al. |
| 4,419,535 A | 12/1983 | O'hara |
| 4,431,004 A | 2/1984 | Bessman et al. |
| 4,431,507 A | 2/1984 | Nankai et al. |
| 4,436,094 A | 3/1984 | Cerami |
| 4,442,841 A * | 4/1984 | Uehara et al. ............ 600/360 |
| 4,477,314 A | 10/1984 | Richter et al. |
| 4,486,290 A | 12/1984 | Cahalan et al. |
| 4,494,950 A | 1/1985 | Fischell |
| 4,506,680 A | 3/1985 | Stokes |
| RE31,916 E | 6/1985 | Oswin et al. |
| 4,538,616 A | 9/1985 | Rogoff |
| 4,554,927 A | 11/1985 | Fussell |
| 4,565,666 A | 1/1986 | Cahalan et al. |
| 4,571,292 A | 2/1986 | Liu et al. |
| 4,577,642 A | 3/1986 | Stokes |
| 4,578,215 A | 3/1986 | Bradley |
| 4,579,120 A | 4/1986 | MacGregor |
| 4,583,976 A | 4/1986 | Ferguson |
| 4,619,793 A | 10/1986 | Lee |
| 4,650,547 A | 3/1987 | Gough |
| 4,655,880 A | 4/1987 | Liu |
| 4,663,824 A | 5/1987 | Kenmochi |
| 4,672,970 A | 6/1987 | Uchida et al. |
| 4,675,346 A | 6/1987 | Lin et al. |
| 4,680,268 A | 7/1987 | Clark, Jr. |
| 4,703,756 A | 11/1987 | Gough et al. |
| 4,703,989 A | 11/1987 | Price et al. |
| 4,711,251 A | 12/1987 | Stokes |
| 4,721,677 A | 1/1988 | Clark, Jr. |
| 4,731,726 A | 3/1988 | Allen |
| 4,734,092 A | 3/1988 | Millerd |
| 4,753,652 A | 6/1988 | Langer et al. |
| 4,757,022 A | 7/1988 | Shults et al. |
| 4,761,748 A | 8/1988 | Le Rat et al. |
| 4,776,343 A | 10/1988 | Hubbard et al. |
| 4,781,680 A | 11/1988 | Redmond et al. |
| 4,795,435 A | 1/1989 | Steer |
| 4,803,243 A | 2/1989 | Fujimoto et al. |
| 4,805,624 A | 2/1989 | Yao et al. |
| 4,805,625 A | 2/1989 | Wyler |
| 4,810,470 A | 3/1989 | Burkhardt et al. |
| 4,813,424 A | 3/1989 | Wilkins |
| 4,826,706 A | 5/1989 | Hilker et al. |
| 4,831,070 A | 5/1989 | McInally et al. |
| 4,849,458 A | 7/1989 | Reed et al. |
| 4,852,573 A | 8/1989 | Kennedy |
| 4,858,615 A | 8/1989 | Meinema |
| 4,871,440 A | 10/1989 | Nagata et al. |
| 4,883,057 A | 11/1989 | Broderick |
| 4,889,744 A | 12/1989 | Quaid |
| 4,890,620 A | 1/1990 | Gough |
| 4,919,141 A | 4/1990 | Zier et al. |
| 4,927,407 A | 5/1990 | Dorman |
| 4,952,618 A | 8/1990 | Olsen |
| 4,953,552 A | 9/1990 | DeMarzo |
| 4,955,861 A | 9/1990 | Enegren et al. |
| 4,958,148 A | 9/1990 | Olson |
| 4,960,594 A | 10/1990 | Honeycutt |
| 4,963,595 A | 10/1990 | Ward et al. |
| 4,970,145 A | 11/1990 | Bennetto et al. |
| 4,974,929 A | 12/1990 | Curry |
| 4,975,175 A | 12/1990 | Karube et al. |
| 4,984,929 A | 1/1991 | Rock et al. |
| 4,986,271 A | 1/1991 | Wilkens et al. |
| 4,988,341 A | 1/1991 | Columbus et al. |
| 4,988,758 A | 1/1991 | Fukuda et al. |
| 4,994,167 A | 2/1991 | Shults et al. |
| 5,007,929 A | 4/1991 | Quaid |
| 5,034,112 A | 7/1991 | Murase et al. |
| 5,050,612 A | 9/1991 | Matsumura |
| 5,055,171 A | 10/1991 | Peck |
| 5,059,654 A | 10/1991 | Hou et al. |
| 5,082,550 A | 1/1992 | Rishpon et al. |
| 5,089,112 A | 2/1992 | Skotheim et al. |
| 5,108,819 A | 4/1992 | Heller et al. |
| 5,127,405 A | 7/1992 | Alcala et al. |
| 5,130,231 A | 7/1992 | Kennedy et al. |
| 5,137,028 A | 8/1992 | Nishimura |
| 5,160,418 A | 11/1992 | Mullen |
| 5,162,407 A | 11/1992 | Turner |
| 5,165,407 A | 11/1992 | Wilson et al. |
| 5,171,689 A | 12/1992 | Kawaguri et al. |
| 5,176,662 A | 1/1993 | Bartholomew et al. |
| 5,190,041 A | 3/1993 | Palti |
| 5,202,261 A | 4/1993 | Musho et al. |
| 5,222,980 A | 6/1993 | Gealow |
| 5,235,003 A | 8/1993 | Ward et al. |
| 5,243,696 A | 9/1993 | Carr et al. |

(56) References Cited

U.S. PATENT DOCUMENTS

| | | |
|---|---|---|
| 5,249,576 A | 10/1993 | Golberger et al. |
| 5,261,892 A | 11/1993 | Bertaud et al. |
| 5,264,104 A | 11/1993 | Gregg et al. |
| 5,265,999 A | 11/1993 | Wenschhof et al. |
| 5,266,179 A | 11/1993 | Nankai et al. |
| 5,269,891 A | 12/1993 | Colin |
| 5,271,736 A | 12/1993 | Picha |
| 5,281,319 A | 1/1994 | Kaneko et al. |
| 5,282,844 A | 2/1994 | Stokes et al. |
| 5,282,848 A | 2/1994 | Schmitt |
| 5,284,140 A | 2/1994 | Allen et al. |
| 5,284,570 A | 2/1994 | Savage et al. |
| 5,285,513 A | 2/1994 | Kaufman et al. |
| 5,287,753 A | 2/1994 | Routh et al. |
| 5,298,144 A | 3/1994 | Spokane |
| 5,299,571 A | 4/1994 | Mastrototaro |
| 5,302,440 A | 4/1994 | Davis |
| 5,307,263 A | 4/1994 | Brown |
| 5,312,361 A | 5/1994 | Zadini et al. |
| 5,314,471 A | 5/1994 | Brauker et al. |
| 5,316,008 A | 5/1994 | Suga et al. |
| 5,322,063 A | 6/1994 | Allen et al. |
| 5,324,322 A | 6/1994 | Grill et al. |
| 5,326,356 A | 7/1994 | Della Valle et al. |
| 5,330,634 A | 7/1994 | Wong et al. |
| 5,331,555 A | 7/1994 | Hashimoto et al. |
| 5,336,102 A | 8/1994 | Cairns et al. |
| 5,337,747 A | 8/1994 | Neftel |
| 5,344,454 A | 9/1994 | Clarke et al. |
| 5,348,788 A | 9/1994 | White |
| 5,352,348 A | 10/1994 | Young et al. |
| 5,354,449 A | 10/1994 | Band et al. |
| 5,356,786 A | 10/1994 | Heller et al. |
| 5,358,409 A | 10/1994 | Obara |
| 5,362,761 A | 11/1994 | Uragami et al. |
| 5,368,028 A | 11/1994 | Palti |
| 5,368,224 A | 11/1994 | Richardson et al. |
| 5,372,133 A | 12/1994 | Hogen Esch |
| 5,372,719 A | 12/1994 | Afejan et al. |
| 5,380,536 A | 1/1995 | Hubbell et al. |
| 5,382,514 A | 1/1995 | Passaniti et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney et al. |
| 5,397,848 A | 3/1995 | Yang et al. |
| 5,411,647 A | 5/1995 | Johnson et al. |
| 5,411,866 A | 5/1995 | Luong |
| 5,425,717 A | 6/1995 | Mohiuddin |
| 5,426,032 A | 6/1995 | Phillips |
| 5,429,129 A | 7/1995 | Lovejoy et al. |
| 5,429,735 A | 7/1995 | Johnson et al. |
| 5,431,160 A | 7/1995 | Wilkins |
| 5,431,921 A | 7/1995 | Thombre |
| 5,451,260 A | 9/1995 | Versteeg et al. |
| 5,453,199 A | 9/1995 | Afejan et al. |
| 5,453,278 A | 9/1995 | Chan et al. |
| 5,458,631 A | 10/1995 | Xavier et al. |
| 5,462,051 A | 10/1995 | Oka et al. |
| 5,462,645 A | 10/1995 | Albery et al. |
| 5,466,356 A | 11/1995 | Schneider et al. |
| 5,474,552 A | 12/1995 | Palti |
| 5,476,776 A | 12/1995 | Wilkins |
| 5,480,711 A | 1/1996 | Ruefer |
| 5,482,473 A | 1/1996 | Lord et al. |
| 5,486,776 A | 1/1996 | Wilkins |
| 5,490,323 A | 2/1996 | Thacker4 et al. |
| 5,494,562 A | 2/1996 | Maley et al. |
| 5,497,772 A * | 3/1996 | Schulman et al. ............ 600/347 |
| 5,502,396 A | 3/1996 | Desarzens et al. |
| 5,507,288 A | 4/1996 | Bocker et al. |
| 5,513,636 A | 5/1996 | Palti |
| 5,516,832 A | 5/1996 | Kennan et al. |
| 5,518,601 A | 5/1996 | Foos et al. |
| 5,529,066 A | 6/1996 | Palti |
| 5,531,878 A | 7/1996 | Vadgama et al. |
| 5,545,200 A | 8/1996 | West et al. |
| 5,545,220 A | 8/1996 | Andrews et al. |
| 5,545,223 A | 8/1996 | Neuenfeldt et al. |
| 5,549,675 A | 8/1996 | Neuenfeldt et al. |
| 5,552,112 A | 9/1996 | Schiffmann et al. |
| 5,564,439 A | 10/1996 | Picha |
| 5,568,806 A | 10/1996 | Cheney et al. |
| 5,569,186 A * | 10/1996 | Lord et al. ...................... 604/67 |
| 5,569,462 A | 10/1996 | Martinson et al. |
| 5,571,395 A | 11/1996 | Park et al. |
| 5,575,293 A | 11/1996 | Miller et al. |
| 5,575,930 A | 11/1996 | Tietje-Girault et al. |
| 5,582,184 A | 12/1996 | Ericson et al. |
| 5,582,697 A | 12/1996 | Ikeda et al. |
| 5,584,813 A | 12/1996 | Livingston et al. |
| 5,584,876 A | 12/1996 | Bruchman et al. |
| 5,586,553 A | 12/1996 | Halili et al. |
| 5,587,273 A | 12/1996 | Yan et al. |
| 5,588,560 A | 12/1996 | Benedict et al. |
| 5,589,133 A | 12/1996 | Suzuki |
| 5,589,563 A | 12/1996 | Ward et al. |
| 5,590,651 A | 1/1997 | Shaffer et al. |
| 5,593,440 A | 1/1997 | Brauker et al. |
| 5,593,852 A | 1/1997 | Heller et al. |
| 5,611,900 A | 3/1997 | Worden |
| 5,626,561 A | 5/1997 | Butler et al. |
| 5,628,890 A | 5/1997 | Carter et al. |
| 5,640,954 A | 6/1997 | Pfeiffer |
| 5,653,756 A | 8/1997 | Clarke et al. |
| 5,658,330 A | 8/1997 | Carlisle et al. |
| 5,660,163 A | 8/1997 | Schulman et al. |
| 5,662,616 A | 9/1997 | Bousquet |
| 5,665,215 A | 9/1997 | Bussmann et al. |
| 5,676,820 A | 10/1997 | Wang et al. |
| 5,682,884 A | 11/1997 | Hill |
| 5,686,829 A | 11/1997 | Girault |
| 5,695,623 A | 12/1997 | Michel et al. |
| 5,696,314 A | 12/1997 | McCaffrey et al. |
| 5,704,354 A | 1/1998 | Priedel et al. |
| 5,706,807 A | 1/1998 | Picha |
| 5,707,502 A | 1/1998 | McCaffrey et al. |
| 5,711,302 A | 1/1998 | Lampropoulos et al. |
| 5,711,861 A | 1/1998 | Ward et al. |
| 5,713,888 A | 2/1998 | Neuenfeldt et al. |
| 5,714,123 A | 2/1998 | Sohrab |
| 5,733,336 A | 3/1998 | Neuenfeldt et al. |
| 5,735,273 A | 4/1998 | Kurnik et al. |
| 5,741,319 A | 4/1998 | Woloszko et al. |
| 5,741,330 A | 4/1998 | Brauker et al. |
| 5,741,634 A | 4/1998 | Nozoe et al. |
| 5,743,262 A | 4/1998 | Lepper, Jr. et al. |
| 5,749,832 A | 5/1998 | Vadgama et al. |
| 5,756,632 A | 5/1998 | Ward et al. |
| 5,763,787 A | 6/1998 | Gravel et al. |
| 5,766,151 A | 6/1998 | Valley et al. |
| 5,776,324 A | 7/1998 | Usala |
| 5,777,060 A | 7/1998 | Van Antwerp |
| 5,782,912 A | 7/1998 | Brauker et al. |
| 5,786,439 A | 7/1998 | Van Antwerp et al. |
| 5,787,900 A | 8/1998 | Butler et al. |
| 5,791,344 A | 8/1998 | Schulman et al. |
| 5,798,065 A | 8/1998 | Picha |
| 5,800,420 A | 9/1998 | Gross |
| 5,800,529 A | 9/1998 | Brauker et al. |
| 5,804,048 A | 9/1998 | Wong et al. |
| 5,807,375 A | 9/1998 | Gross et al. |
| 5,807,406 A | 9/1998 | Brauker et al. |
| 5,811,487 A | 9/1998 | Schulz, Jr. et al. |
| 5,820,622 A | 10/1998 | Gross et al. |
| 5,822,715 A | 10/1998 | Worthington et al. |
| 5,823,802 A | 10/1998 | Bartley |
| 5,833,603 A | 11/1998 | Kovacs et al. |
| 5,836,886 A | 11/1998 | Itoigawa |
| 5,837,728 A | 11/1998 | Purcell |
| 5,840,240 A | 11/1998 | Stenoien et al. |
| 5,851,197 A | 12/1998 | Marano et al. |
| 5,858,365 A | 1/1999 | Feller |
| 5,863,400 A | 1/1999 | Drummond et al. |

(56) References Cited

U.S. PATENT DOCUMENTS

| | | | |
|---|---|---|---|
| 5,871,499 A | 2/1999 | Hahn et al. | |
| 5,871,514 A | 2/1999 | Wiklund et al. | |
| 5,874,500 A | 2/1999 | Rhee et al. | |
| 5,879,373 A | 3/1999 | Roper et al. | |
| 5,882,494 A * | 3/1999 | Van Antwerp | 600/347 |
| 5,897,578 A | 4/1999 | Wiklund et al. | |
| 5,913,998 A | 6/1999 | Butler et al. | |
| 5,914,026 A | 6/1999 | Blubaugh, Jr. et al. | |
| 5,916,445 A | 6/1999 | Hjerten et al. | |
| 5,919,215 A | 7/1999 | Wiklund et al. | |
| 5,928,130 A | 7/1999 | Schmidt | |
| 5,931,814 A | 8/1999 | Alex et al. | |
| 5,935,785 A | 8/1999 | Reber et al. | |
| 5,944,661 A | 8/1999 | Swette et al. | |
| 5,954,643 A | 9/1999 | Van Antwerp et al. | |
| 5,954,954 A | 9/1999 | Houck et al. | |
| 5,957,854 A | 9/1999 | Besson et al. | |
| 5,959,050 A | 9/1999 | Mosbach et al. | |
| 5,961,451 A | 10/1999 | Reber et al. | |
| 5,964,745 A | 10/1999 | Lyles et al. | |
| 5,964,804 A | 10/1999 | Brauker et al. | |
| 5,964,993 A | 10/1999 | Blubaugh et al. | |
| 5,967,986 A | 10/1999 | Cimochowski et al. | |
| 5,972,199 A | 10/1999 | Heller | |
| 5,985,129 A | 11/1999 | Gough et al. | |
| 5,999,849 A | 12/1999 | Gord et al. | |
| 6,001,067 A | 12/1999 | Shults et al. | |
| 6,011,984 A | 1/2000 | Van Antwerp et al. | |
| 6,013,113 A | 1/2000 | Mika | |
| 6,017,435 A | 1/2000 | Hassard et al. | |
| 6,036,924 A | 3/2000 | Simons et al. | |
| 6,048,691 A | 4/2000 | Maracas | |
| 6,049,727 A | 4/2000 | Crothall | |
| 6,051,372 A | 4/2000 | Bayerl et al. | |
| 6,051,389 A | 4/2000 | Ahl et al. | |
| 6,057,377 A | 5/2000 | Sasaki et al. | |
| 6,059,946 A | 5/2000 | Yukawa et al. | |
| 6,060,640 A | 5/2000 | Pauley et al. | |
| 6,063,637 A | 5/2000 | Arnold et al. | |
| 6,065,154 A | 5/2000 | Hulings et al. | |
| 6,066,083 A | 5/2000 | Slater et al. | |
| 6,066,448 A | 5/2000 | Wohlstadter et al. | |
| 6,074,775 A | 6/2000 | Gartstein et al. | |
| 6,081,736 A | 6/2000 | Colvin et al. | |
| 6,088,608 A | 7/2000 | Schulman et al. | |
| 6,091,975 A | 7/2000 | Daddona et al. | |
| 6,093,156 A | 7/2000 | Cunningham et al. | |
| 6,093,172 A | 7/2000 | Funderburk et al. | |
| 6,101,404 A | 8/2000 | Yoon et al. | |
| 6,103,033 A | 8/2000 | Say et al. | |
| 6,103,533 A | 8/2000 | Hassard et al. | |
| 6,115,622 A | 9/2000 | Minoz | |
| 6,117,290 A | 9/2000 | Say | |
| 6,119,028 A * | 9/2000 | Schulman et al. | 600/345 |
| 6,122,536 A | 9/2000 | Sun et al. | |
| 6,134,461 A * | 10/2000 | Say et al. | 600/345 |
| 6,135,978 A | 10/2000 | Houben et al. | |
| 6,144,869 A | 11/2000 | Berner et al. | |
| 6,144,871 A * | 11/2000 | Saito et al. | 600/395 |
| 6,157,860 A | 12/2000 | Hauser et al. | |
| 6,168,568 B1 | 1/2001 | Gavriely | |
| 6,169,155 B1 | 1/2001 | Alvarez et al. | |
| 6,175,752 B1 | 1/2001 | Say et al. | |
| 6,187,062 B1 | 2/2001 | Oweis et al. | |
| 6,198,969 B1 | 3/2001 | Kuzma | |
| 6,200,772 B1 | 3/2001 | Vadgama et al. | |
| 6,212,416 B1 | 4/2001 | Ward et al. | |
| 6,214,901 B1 | 4/2001 | Chudzik et al. | |
| 6,219,574 B1 | 4/2001 | Cormier et al. | |
| 6,231,879 B1 | 5/2001 | Li et al. | |
| 6,232,783 B1 | 5/2001 | Merrill | |
| 6,233,471 B1 | 5/2001 | Berner et al. | |
| 6,248,067 B1 | 6/2001 | Causey, III et al. | |
| 6,251,280 B1 | 6/2001 | Dai et al. | |
| 6,255,592 B1 | 7/2001 | Pennington et al. | |
| 6,264,825 B1 | 7/2001 | Blackburn et al. | |
| 6,266,551 B1 | 7/2001 | Osadchy et al. | |
| 6,268,161 B1 * | 7/2001 | Han et al. | 435/14 |
| 6,274,285 B1 | 8/2001 | Gries et al. | |
| 6,274,686 B1 | 8/2001 | Mosbach | |
| 6,275,717 B1 | 8/2001 | Gross et al. | |
| 6,284,478 B1 | 9/2001 | Heller et al. | |
| 6,285,897 B1 | 9/2001 | Kilcoyne et al. | |
| 6,293,925 B1 | 9/2001 | Safabash et al. | |
| 6,294,281 B1 | 9/2001 | Heller | |
| 6,296,615 B1 | 10/2001 | Brockway et al. | |
| 6,300,002 B1 | 10/2001 | Webb et al. | |
| 6,306,424 B1 | 10/2001 | Vyakarnam et al. | |
| 6,309,384 B1 | 10/2001 | Harrington et al. | |
| 6,310,110 B1 | 10/2001 | Markowitz et al. | |
| 6,315,738 B1 | 11/2001 | Nishikawa et al. | |
| 6,319,566 B1 | 11/2001 | Polanyi et al. | |
| 6,325,978 B1 | 12/2001 | Labuda et al. | |
| 6,325,979 B1 | 12/2001 | Hahn et al. | |
| 6,326,160 B1 | 12/2001 | Dunn et al. | |
| 6,329,161 B1 | 12/2001 | Heller et al. | |
| 6,330,464 B1 | 12/2001 | Colvin, Jr. et al. | |
| 6,336,269 B1 | 1/2002 | Eldridge et al. | |
| 6,343,225 B1 * | 1/2002 | Clark, Jr. | 600/347 |
| 6,360,888 B1 | 3/2002 | McIvor et al. | |
| 6,365,670 B1 | 4/2002 | Fry | |
| 6,366,794 B1 | 4/2002 | Moussy et al. | |
| 6,368,141 B1 | 4/2002 | VanAntwerp et al. | |
| 6,368,274 B1 * | 4/2002 | Van Antwerp et al. | 600/365 |
| 6,371,963 B1 | 4/2002 | Nishtala et al. | |
| 6,379,317 B1 | 4/2002 | Kintzig et al. | |
| 6,400,974 B1 | 6/2002 | Lesho | |
| 6,406,066 B1 | 6/2002 | Uegane | |
| 6,409,674 B1 | 6/2002 | Brockway et al. | |
| 6,413,393 B1 | 7/2002 | Van Antwerp et al. | |
| 6,418,332 B1 | 7/2002 | Mastrototaro et al. | |
| 6,424,847 B1 | 7/2002 | Mastrototaro et al. | |
| 6,442,413 B1 | 8/2002 | Silver | |
| 6,447,448 B1 | 9/2002 | Ishikawa et al. | |
| 6,447,542 B1 | 9/2002 | Weadock | |
| 6,454,710 B1 | 9/2002 | Ballerstadt et al. | |
| 6,459,917 B1 | 10/2002 | Gowda et al. | |
| 6,461,496 B1 | 10/2002 | Feldman et al. | |
| 6,466,810 B1 | 10/2002 | Ward et al. | |
| 6,468,287 B1 | 10/2002 | Baugh | |
| 6,471,993 B1 | 10/2002 | Shastri et al. | |
| 6,484,045 B1 | 11/2002 | Holker et al. | |
| 6,484,046 B1 | 11/2002 | Say et al. | |
| 6,484,132 B1 | 11/2002 | Hively et al. | |
| 6,487,429 B2 | 11/2002 | Hockersmith et al. | |
| 6,494,830 B1 | 12/2002 | Wessel | |
| 6,497,729 B1 | 12/2002 | Moussy et al. | |
| 6,498,043 B1 | 12/2002 | Schulman et al. | |
| 6,498,941 B1 | 12/2002 | Jackson | |
| 6,510,329 B2 | 1/2003 | Heckel | |
| 6,512,939 B1 | 1/2003 | Colvin et al. | |
| 6,514,718 B2 | 2/2003 | Heller et al. | |
| 6,517,508 B1 | 2/2003 | Utterberg et al. | |
| 6,520,326 B2 | 2/2003 | Mcivor et al. | |
| 6,520,997 B1 | 2/2003 | Pekkarinen et al. | |
| 6,528,584 B2 | 3/2003 | Kennedy et al. | |
| 6,537,318 B1 | 3/2003 | Ita et al. | |
| 6,541,107 B1 | 4/2003 | Zhong et al. | |
| 6,545,085 B2 | 4/2003 | Kilgour et al. | |
| 6,546,268 B1 * | 4/2003 | Ishikawa et al. | 600/345 |
| 6,547,839 B2 | 4/2003 | Zhang et al. | |
| 6,553,241 B2 | 4/2003 | Mannheimer et al. | |
| 6,558,320 B1 | 5/2003 | Causey | |
| 6,558,321 B1 | 5/2003 | Burd et al. | |
| 6,558,351 B1 | 5/2003 | Steil et al. | |
| 6,560,471 B1 | 5/2003 | Heller et al. | |
| 6,565,509 B1 | 5/2003 | Say et al. | |
| 6,569,309 B2 | 5/2003 | Otsuka et al. | |
| 6,572,745 B2 | 6/2003 | Rappin et al. | |
| 6,579,690 B1 | 6/2003 | Bonnecaze et al. | |
| 6,584,335 B1 | 6/2003 | Haar et al. | |
| 6,587,705 B1 | 7/2003 | Kim et al. | |
| 6,591,125 B1 | 7/2003 | Buse et al. | |
| 6,612,984 B1 | 9/2003 | Kerr | |

(56) References Cited

U.S. PATENT DOCUMENTS

| | | |
|---|---|---|
| 6,613,379 B2 | 9/2003 | Ward et al. |
| 6,618,934 B1 | 9/2003 | Feldman et al. |
| 6,633,772 B2 | 10/2003 | Ford et al. |
| 6,645,181 B1 | 11/2003 | Lavi et al. |
| 6,654,625 B1 | 11/2003 | Say et al. |
| 6,666,821 B2 | 12/2003 | Keimel |
| 6,689,265 B2 | 2/2004 | Heller et al. |
| 6,695,860 B1 | 2/2004 | Ward et al. |
| 6,702,857 B2 | 3/2004 | Brauker et al. |
| 6,702,972 B1 | 3/2004 | Markle |
| 6,705,833 B2 | 3/2004 | Tam et al. |
| 6,721,587 B2 | 4/2004 | Gough |
| 6,733,655 B1 | 5/2004 | Davies et al. |
| 6,736,777 B2 | 5/2004 | Kim et al. |
| 6,737,158 B1 | 5/2004 | Thompson |
| 6,740,059 B2 | 5/2004 | Flaherty |
| 6,741,877 B1 | 5/2004 | Shults et al. |
| 6,742,635 B2 | 6/2004 | Neel et al. |
| 6,743,635 B2 | 6/2004 | Neel et al. |
| 6,773,565 B2 | 8/2004 | Kunimoto et al. |
| 6,793,632 B2 | 9/2004 | Sohrab |
| 6,793,802 B2 | 9/2004 | Lee et al. |
| 6,801,041 B2 | 10/2004 | Karinka et al. |
| 6,802,957 B2 | 10/2004 | Jung et al. |
| 6,804,544 B2 | 10/2004 | van Antwerp et al. |
| 6,809,653 B1 | 10/2004 | Mann et al. |
| 6,815,186 B2 | 11/2004 | Clark, Jr. |
| 6,830,551 B1 | 12/2004 | Uchigaki et al. |
| 6,862,465 B2 | 3/2005 | Shults et al. |
| 6,875,386 B1 | 4/2005 | Ward et al. |
| 6,885,883 B2 | 4/2005 | Parris et al. |
| 6,891,317 B2 | 5/2005 | Pei et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,931,327 B2 | 8/2005 | Goode, Jr. et al. |
| 6,936,006 B2 | 8/2005 | Sabra |
| 6,952,604 B2 | 10/2005 | DeNuzzio et al. |
| 6,965,791 B1 | 11/2005 | Hitchcock et al. |
| 6,972,080 B1 | 12/2005 | Tomioka et al. |
| 6,991,643 B2 | 1/2006 | Saadat |
| 7,003,336 B2 | 2/2006 | Holker et al. |
| 7,003,341 B2 | 2/2006 | Say et al. |
| 7,058,437 B2 | 6/2006 | Buse et al. |
| 7,060,059 B2 | 6/2006 | Keith et al. |
| 7,070,580 B2 | 7/2006 | Nielsen |
| 7,074,307 B2 | 7/2006 | Simpson et al. |
| 7,078,582 B2 | 7/2006 | Stebbings et al. |
| 7,081,195 B2 | 7/2006 | Simpson et al. |
| 7,098,803 B2 | 8/2006 | Mann et al. |
| 7,110,803 B2 | 9/2006 | Shults et al. |
| 7,115,884 B1 | 10/2006 | Walt et al. |
| 7,134,999 B2 | 11/2006 | Brauker et al. |
| 7,136,689 B2 | 11/2006 | Shults et al. |
| 7,153,265 B2 | 12/2006 | Vachon |
| 7,166,074 B2 | 1/2007 | Reghabit et al. |
| 7,169,289 B2 | 1/2007 | Schulein et al. |
| 7,190,988 B2 | 3/2007 | Say et al. |
| 7,192,450 B2 | 3/2007 | Brauker et al. |
| 7,207,974 B2 | 4/2007 | Safabash et al. |
| 7,225,535 B2 | 6/2007 | Feldman et al. |
| 7,267,665 B2 | 9/2007 | Steil et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,324,012 B2 | 1/2008 | Mann et al. |
| 7,344,499 B1 * | 3/2008 | Prausnitz et al. ............ 600/309 |
| 7,364,592 B2 | 4/2008 | Carr-Brendel et al. |
| 7,366,556 B2 | 4/2008 | Brister et al. |
| 7,366,566 B2 | 4/2008 | Brister et al. |
| 7,381,184 B2 | 6/2008 | Funderburk et al. |
| 7,399,277 B2 | 7/2008 | Saidara et al. |
| 7,402,153 B2 | 7/2008 | Steil et al. |
| 7,404,819 B1 | 7/2008 | Darios et al. |
| 7,417,164 B2 | 8/2008 | Suri |
| 7,424,318 B2 | 9/2008 | Brister et al. |
| 7,426,408 B2 | 9/2008 | DeNuzzio et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,525,298 B2 | 4/2009 | Morgan et al. |
| 7,582,059 B2 | 9/2009 | Funderburk et al. |
| 7,632,228 B2 | 12/2009 | Brauker et al. |
| 7,636,602 B2 | 12/2009 | Baru Fassio et al. |
| 7,637,868 B2 | 12/2009 | Saint et al. |
| 7,640,048 B2 | 12/2009 | Dobbles et al. |
| 7,654,956 B2 | 2/2010 | Brister et al. |
| 7,657,297 B2 | 2/2010 | Simpson et al. |
| 7,697,967 B2 | 4/2010 | Stafford |
| 7,713,574 B2 | 5/2010 | Brister et al. |
| 7,862,622 B2 | 1/2011 | Dunlap et al. |
| 7,879,010 B2 | 2/2011 | Hunn et al. |
| 7,885,697 B2 | 2/2011 | Brister et al. |
| 7,946,984 B2 | 5/2011 | Brister et al. |
| 7,949,381 B2 | 5/2011 | Brister et al. |
| 8,118,877 B2 | 2/2012 | Brauker et al. |
| 8,229,534 B2 | 7/2012 | Brister et al. |
| 8,290,560 B2 | 10/2012 | Kamath et al. |
| 8,353,881 B2 * | 1/2013 | Jennewine ........... A61M 5/1723 604/265 |
| 8,366,614 B2 | 2/2013 | Say et al. |
| 8,457,708 B2 | 6/2013 | Brister et al. |
| 8,463,350 B2 | 6/2013 | Kamath et al. |
| 9,669,156 B2 * | 6/2017 | Jennewine .......... A61B 5/15142 |
| 2001/0016682 A1 | 8/2001 | Berner et al. |
| 2001/0020546 A1 | 9/2001 | Eldridge |
| 2001/0044413 A1 | 11/2001 | Pierce et al. |
| 2001/0051766 A1 | 12/2001 | Gazdzinski |
| 2001/0051768 A1 | 12/2001 | Schulman et al. |
| 2001/0053933 A1 | 12/2001 | Phaneuf et al. |
| 2002/0016535 A1 | 2/2002 | Martin et al. |
| 2002/0019330 A1 | 2/2002 | Murray et al. |
| 2002/0022883 A1 | 2/2002 | Burg |
| 2002/0023852 A1 | 2/2002 | McIvor et al. |
| 2002/0032531 A1 | 3/2002 | Mansky et al. |
| 2002/0042561 A1 | 4/2002 | Schulman et al. |
| 2002/0055673 A1 * | 5/2002 | Van Antwerp et al. ....... 600/365 |
| 2002/0077599 A1 | 6/2002 | Wojcik |
| 2002/0084196 A1 | 7/2002 | Liamos et al. |
| 2002/0099282 A1 | 7/2002 | Knobbe et al. |
| 2002/0099997 A1 | 7/2002 | Piret |
| 2002/0100474 A1 | 8/2002 | Kellner et al. |
| 2002/0100725 A1 | 8/2002 | Lee et al. |
| 2002/0119711 A1 | 8/2002 | Vanantwerpt et al. |
| 2002/0128546 A1 | 9/2002 | Silver |
| 2002/0133224 A1 | 9/2002 | Shults et al. |
| 2002/0137991 A1 | 9/2002 | Scarantino et al. |
| 2002/0151796 A1 | 10/2002 | Koulik |
| 2002/0151816 A1 | 10/2002 | Rich et al. |
| 2002/0161288 A1 | 10/2002 | Shin et al. |
| 2002/0169369 A1 * | 11/2002 | Ward et al. .................... 600/347 |
| 2002/0177763 A1 | 11/2002 | Burns et al. |
| 2002/0182241 A1 | 12/2002 | Boerenstein et al. |
| 2002/0185384 A1 | 12/2002 | Leong et al. |
| 2002/0188185 A1 * | 12/2002 | Sohrab .......................... 600/347 |
| 2002/0188216 A1 | 12/2002 | Kayyali et al. |
| 2002/0193885 A1 | 12/2002 | Legeay et al. |
| 2003/0004457 A1 | 1/2003 | Andersson |
| 2003/0006669 A1 | 1/2003 | Pei et al. |
| 2003/0023317 A1 | 1/2003 | Brauker et al. |
| 2003/0032874 A1 | 2/2003 | Rhodes et al. |
| 2003/0036773 A1 | 2/2003 | Whitehurst et al. |
| 2003/0049166 A1 | 3/2003 | Pendo et al. |
| 2003/0059631 A1 | 3/2003 | Al-Lamee |
| 2003/0065254 A1 | 4/2003 | Schulman et al. |
| 2003/0070548 A1 | 4/2003 | Clausen |
| 2003/0097082 A1 | 5/2003 | Purdy et al. |
| 2003/0100821 A1 | 5/2003 | Heller et al. |
| 2003/0125613 A1 | 7/2003 | Enegren et al. |
| 2003/0130616 A1 | 7/2003 | Steil et al. |
| 2003/0132227 A1 | 7/2003 | Geisler |
| 2003/0134347 A1 | 7/2003 | Heller et al. |

(56) References Cited

U.S. PATENT DOCUMENTS

| | | |
|---|---|---|
| 2003/0138674 A1 | 7/2003 | Zeikus et al. |
| 2003/0181794 A1* | 9/2003 | Rini et al. .................. 600/300 |
| 2003/0186457 A1 | 10/2003 | Iwaki et al. |
| 2003/0199745 A1 | 10/2003 | Burson et al. |
| 2003/0199878 A1 | 10/2003 | Pohjonen |
| 2003/0203498 A1 | 10/2003 | Neel et al. |
| 2003/0211625 A1 | 11/2003 | Cohan |
| 2003/0225437 A1 | 12/2003 | Ferguson |
| 2003/0235817 A1 | 12/2003 | Bartkowiak et al. |
| 2004/0002682 A1 | 1/2004 | Kovelman et al. |
| 2004/0008761 A1 | 1/2004 | Kelliher et al. |
| 2004/0011671 A1 | 1/2004 | Shults et al. |
| 2004/0015063 A1 | 1/2004 | DeNuzzio et al. |
| 2004/0015134 A1 | 1/2004 | Lavi et al. |
| 2004/0024327 A1 | 2/2004 | Brodnick |
| 2004/0030285 A1 | 2/2004 | Lavi et al. |
| 2004/0052689 A1 | 3/2004 | Yao |
| 2004/0064156 A1 | 4/2004 | Shah et al. |
| 2004/0068230 A1 | 4/2004 | Estes et al. |
| 2004/0074785 A1 | 4/2004 | Holker |
| 2004/0078219 A1 | 4/2004 | Kaylor |
| 2004/0088023 A1 | 5/2004 | Imran et al. |
| 2004/0106857 A1 | 6/2004 | Gough |
| 2004/0106859 A1 | 6/2004 | Say et al. |
| 2004/0120848 A1 | 6/2004 | Teodorczyk |
| 2004/0133131 A1 | 7/2004 | Kuhn et al. |
| 2004/0133164 A1 | 7/2004 | Funderburk et al. |
| 2004/0158207 A1 | 8/2004 | Hunn et al. |
| 2004/0167801 A1 | 8/2004 | Say et al. |
| 2004/0173472 A1 | 9/2004 | Jung et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0199059 A1 | 10/2004 | Brauker et al. |
| 2004/0204687 A1 | 10/2004 | Morgensen |
| 2004/0236200 A1 | 11/2004 | Say et al. |
| 2004/0236251 A1 | 11/2004 | Roe et al. |
| 2004/0242982 A1 | 12/2004 | Sakata et al. |
| 2004/0254433 A1 | 12/2004 | Bandis |
| 2005/0006122 A1 | 1/2005 | Burnette |
| 2005/0010265 A1 | 1/2005 | Baru Fassio et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0038332 A1 | 2/2005 | Saidara et al. |
| 2005/0043598 A1 | 2/2005 | Goode et al. |
| 2005/0051427 A1 | 3/2005 | Brauker et al. |
| 2005/0051440 A1 | 3/2005 | Simpson et al. |
| 2005/0054909 A1 | 3/2005 | Petisce et al. |
| 2005/0056551 A1 | 3/2005 | White et al. |
| 2005/0056552 A1 | 3/2005 | Simpson et al. |
| 2005/0059871 A1 | 3/2005 | Gough et al. |
| 2005/0090607 A1 | 4/2005 | Tapsak et al. |
| 2005/0096519 A1 | 5/2005 | DeNuzzio et al. |
| 2005/0103625 A1 | 5/2005 | Rhodes et al. |
| 2005/0112169 A1 | 5/2005 | Brauker et al. |
| 2005/0115832 A1 | 6/2005 | Simpson et al. |
| 2005/0121322 A1 | 6/2005 | Say |
| 2005/0133368 A1 | 6/2005 | Davies et al. |
| 2005/0139489 A1 | 6/2005 | Oliver et al. |
| 2005/0143635 A1 | 6/2005 | Kamath et al. |
| 2005/0143636 A1 | 6/2005 | Zhang et al. |
| 2005/0143675 A1 | 6/2005 | Neel et al. |
| 2005/0173245 A1 | 8/2005 | Feldman et al. |
| 2005/0176136 A1 | 8/2005 | Burd et al. |
| 2005/0177036 A1 | 8/2005 | Shults et al. |
| 2005/0181012 A1 | 8/2005 | Saint et al. |
| 2005/0183954 A1 | 8/2005 | Hitchcock et al. |
| 2005/0192557 A1 | 9/2005 | Brauker et al. |
| 2005/0195930 A1 | 9/2005 | Spital et al. |
| 2005/0211571 A1 | 9/2005 | Schulein et al. |
| 2005/0215871 A1 | 9/2005 | Feldman et al. |
| 2005/0225361 A1 | 10/2005 | Rhee |
| 2005/0242479 A1 | 11/2005 | Petisce et al. |
| 2005/0245795 A1 | 11/2005 | Goode et al. |
| 2005/0245799 A1 | 11/2005 | Brauker et al. |
| 2005/0251083 A1 | 11/2005 | Carr-Brendel et al. |
| 2005/0258037 A1 | 11/2005 | Hajizadeh et al. |
| 2005/0261563 A1 | 11/2005 | Zhou et al. |
| 2005/0267440 A1* | 12/2005 | Herman ................. A61N 1/306 604/501 |
| 2005/0272989 A1 | 12/2005 | Shah et al. |
| 2006/0008370 A1 | 1/2006 | Massaro et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0040402 A1 | 2/2006 | Brauker et al. |
| 2006/0047215 A1 | 3/2006 | Newman et al. |
| 2006/0155180 A1 | 7/2006 | Brister et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189856 A1 | 8/2006 | Petisce et al. |
| 2006/0195029 A1 | 8/2006 | Shults et al. |
| 2006/0198864 A1 | 9/2006 | Shults et al. |
| 2006/0200020 A1 | 9/2006 | Brister et al. |
| 2006/0200022 A1 | 9/2006 | Brauker et al. |
| 2006/0204536 A1 | 9/2006 | Shults et al. |
| 2006/0211921 A1 | 9/2006 | Brauker et al. |
| 2006/0222566 A1 | 10/2006 | Brauker et al. |
| 2006/0224108 A1 | 10/2006 | Brauker et al. |
| 2006/0229512 A1 | 10/2006 | Petisce et al. |
| 2006/0235285 A1 | 10/2006 | Brister et al. |
| 2006/0257995 A1 | 11/2006 | Simpson et al. |
| 2006/0257996 A1 | 11/2006 | Simpson et al. |
| 2006/0258761 A1 | 11/2006 | Boock et al. |
| 2006/0263763 A1 | 11/2006 | Simpson et al. |
| 2006/0270922 A1 | 11/2006 | Brauker et al. |
| 2006/0281985 A1 | 12/2006 | Ward et al. |
| 2007/0017805 A1 | 1/2007 | Hodges et al. |
| 2007/0027370 A1 | 2/2007 | Brauker et al. |
| 2007/0027384 A1 | 2/2007 | Brister et al. |
| 2007/0027385 A1 | 2/2007 | Brister et al. |
| 2007/0032717 A1 | 2/2007 | Brister et al. |
| 2007/0032718 A1 | 2/2007 | Shults et al. |
| 2007/0045902 A1 | 3/2007 | Brauker et al. |
| 2007/0073129 A1 | 3/2007 | Shah et al. |
| 2007/0093704 A1 | 4/2007 | Brister et al. |
| 2007/0173711 A1 | 7/2007 | Shah et al. |
| 2007/0197889 A1 | 8/2007 | Brister et al. |
| 2007/0200254 A1 | 8/2007 | Curry |
| 2007/0202672 A1 | 8/2007 | Curry |
| 2007/0203966 A1 | 8/2007 | Brauker et al. |
| 2007/0208246 A1 | 9/2007 | Brauker et al. |
| 2007/0213611 A1 | 9/2007 | Simpson et al. |
| 2007/0232879 A1 | 10/2007 | Brister et al. |
| 2007/0235331 A1 | 10/2007 | Simpson et al. |
| 2007/0259217 A1 | 11/2007 | Logan |
| 2008/0021666 A1 | 1/2008 | Goode et al. |
| 2008/0033268 A1 | 2/2008 | Stafford |
| 2008/0045824 A1 | 2/2008 | Tapsak et al. |
| 2008/0064944 A1 | 3/2008 | Van Antwerp et al. |
| 2008/0242961 A1 | 6/2008 | Brister et al. |
| 2008/0187655 A1 | 8/2008 | Markle et al. |
| 2008/0188722 A1 | 8/2008 | Markle et al. |

(56) References Cited

U.S. PATENT DOCUMENTS

| | | |
|---|---|---|
| 2008/0188725 A1 | 8/2008 | Markle et al. |
| 2008/0188731 A1 | 8/2008 | Brister et al. |
| 2008/0194935 A1 | 8/2008 | Brister et al. |
| 2008/0194938 A1 | 8/2008 | Brister et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0275313 A1 | 11/2008 | Brister et al. |
| 2008/0296155 A1 | 12/2008 | Shults et al. |
| 2008/0305009 A1 | 12/2008 | Gamsey et al. |
| 2008/0305506 A1 | 12/2008 | Suri |
| 2009/0018418 A1 | 1/2009 | Markle et al. |
| 2009/0018426 A1 | 1/2009 | Markle et al. |
| 2009/0036763 A1 | 2/2009 | Brauker et al. |
| 2009/0045055 A1 | 2/2009 | Rhodes et al. |
| 2009/0061528 A1 | 3/2009 | Suri |
| 2009/0062633 A1 | 3/2009 | Brauker et al. |
| 2009/0076356 A1 | 3/2009 | Simpson |
| 2009/0076360 A1 | 3/2009 | Brister et al. |
| 2009/0081803 A1 | 3/2009 | Gamsey et al. |
| 2009/0099434 A1 | 4/2009 | Liu et al. |
| 2009/0099436 A1 | 4/2009 | Brister et al. |
| 2009/0124879 A1 | 5/2009 | Brister et al. |
| 2009/0143660 A1 | 6/2009 | Brister et al. |
| 2009/0177143 A1 | 7/2009 | Markle et al. |
| 2009/0182217 A1 | 7/2009 | Li et al. |
| 2009/0187090 A1 | 7/2009 | Say et al. |
| 2009/0187091 A1 | 7/2009 | Say et al. |
| 2009/0192751 A1 | 7/2009 | Kamath et al. |
| 2009/0242399 A1 | 10/2009 | Kamath et al. |
| 2009/0242425 A1 | 10/2009 | Kamath et al. |
| 2009/0264719 A1 | 10/2009 | Markle et al. |
| 2010/0069728 A1 | 3/2010 | Funderburk et al. |
| 2010/0081908 A1 | 4/2010 | Dobbles et al. |
| 2010/0087724 A1 | 4/2010 | Brauker et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0212583 A1 | 8/2010 | Brister et al. |
| 2011/0087196 A1 | 4/2011 | Hunn et al. |
| 2011/0178378 A1 | 7/2011 | Brister et al. |
| 2011/0190614 A1 | 8/2011 | Brister et al. |
| 2011/0290645 A1 | 12/2011 | Brister et al. |
| 2011/0313543 A1 | 12/2011 | Brauker et al. |
| 2012/0277562 A1 | 11/2012 | Brister et al. |
| 2013/0281931 A1 | 10/2013 | Hunn et al. |

FOREIGN PATENT DOCUMENTS

| | | |
|---|---|---|
| EP | 0098592 | 1/1984 |
| EP | 0 127 958 | 12/1984 |
| EP | 0 284 518 | 9/1988 |
| EP | 0143517 B1 | 4/1989 |
| EP | 0 320 109 | 6/1989 |
| EP | 0 353 328 | 2/1990 |
| EP | 0 390 390 | 10/1990 |
| EP | 0 476 980 | 3/1992 |
| EP | 0520443 A2 | 12/1992 |
| EP | 0319277 B1 | 3/1993 |
| EP | 0 563 795 | 10/1993 |
| EP | 0567725 A1 | 11/1993 |
| EP | 0 561 966 | 10/1994 |
| EP | 0 286 118 B1 | 1/1995 |
| EP | 0 776 628 A2 | 6/1997 |
| EP | 0 838 230 A | 4/1998 |
| EP | 0777122 B1 | 4/2002 |
| EP | 1 077 636 | 1/2004 |
| EP | 2327362 A1 | 6/2011 |
| EP | 2329770 B1 | 9/2014 |
| EP | 2335584 B1 | 6/2015 |
| FR | 2656423 | 6/1991 |
| FR | 2760962 | 9/1998 |
| GB | 2149918 | 6/1985 |
| JP | 02002913 | 1/1990 |
| JP | 3-293556 | 12/1991 |
| WO | WO 1981-003614 | 12/1981 |
| WO | WO 89/02720 | 4/1989 |
| WO | WO 90/13021 | 11/1990 |
| WO | WO 91/09302 | 6/1991 |
| WO | WO 92/07525 | 5/1992 |
| WO | WO 1992-007525 | 5/1992 |
| WO | WO 92/10584 | 6/1992 |
| WO | WO 92/13271 | 8/1992 |
| WO | WO 93/14693 | 8/1993 |
| WO | WO 93/19701 | 10/1993 |
| WO | WO 93/23744 | 11/1993 |
| WO | WO 95/02357 | 1/1995 |
| WO | WO 96/25089 | 2/1995 |
| WO | WO 95/07109 | 3/1995 |
| WO | WO 1997-019344 | 11/1995 |
| WO | WO 96/01611 | 1/1996 |
| WO | WO 96/14026 | 5/1996 |
| WO | WO 96/25088 | 8/1996 |
| WO | WO 96/25089 | 8/1996 |
| WO | WO 96/32076 | 10/1996 |
| WO | WO 96/36296 | 11/1996 |
| WO | WO 97/01986 | 1/1997 |
| WO | WO 97/06727 | 2/1997 |
| WO | WO 97/17884 | 5/1997 |
| WO | WO 97/43633 | 11/1997 |
| WO | WO 98/01071 | 1/1998 |
| WO | WO 98/19159 | 5/1998 |
| WO | WO 98/24358 | 6/1998 |
| WO | WO 98/33549 | 8/1998 |
| WO | WO 98/38906 | 9/1998 |
| WO | WO 1998-038906 | 9/1998 |
| WO | WO 98/42249 | 10/1998 |
| WO | WO 98/56293 | 12/1998 |
| WO | WO 1998-058250 | 12/1998 |
| WO | WO 1999-012607 | 3/1999 |
| WO | WO 99/56613 | 4/1999 |
| WO | WO 1999-029230 | 6/1999 |
| WO | WO 99/33504 | 7/1999 |
| WO | WO 1999-033504 | 7/1999 |
| WO | WO 1999-056613 | 11/1999 |
| WO | WO 00/13003 | 3/2000 |
| WO | WO 2000-013003 | 3/2000 |
| WO | WO 00/19887 | 4/2000 |
| WO | WO 00/32098 | 6/2000 |
| WO | WO 00/33065 | 6/2000 |
| WO | WO 00/49940 | 8/2000 |
| WO | WO 00/049941 | 8/2000 |
| WO | WO 00/049942 | 8/2000 |
| WO | WO 00/59373 | 10/2000 |
| WO | WO 00/074753 | 12/2000 |
| WO | WO 01/12158 | 2/2001 |
| WO | WO 2001-012158 | 2/2001 |
| WO | WO 01/20019 A2 | 3/2001 |
| WO | WO 01/20334 A1 | 3/2001 |
| WO | WO 01/43660 | 6/2001 |
| WO | WO 01/052935 | 7/2001 |
| WO | WO 01/58348 | 8/2001 |
| WO | WO 01/064105 | 9/2001 |
| WO | WO 01/073109 | 10/2001 |
| WO | WO 2002-007617 | 1/2002 |
| WO | WO 2002-043585 | 6/2002 |
| WO | WO 02/058537 | 8/2002 |
| WO | WO 2002-058537 | 8/2002 |
| WO | WO 2002-100457 | 12/2002 |
| WO | WO 2003-028797 | 4/2003 |
| WO | WO 03/082091 | 9/2003 |
| WO | WO 2003-072164 | 9/2003 |
| WO | WO 03/094714 | 11/2003 |
| WO | WO 03/097866 | 11/2003 |
| WO | WO 2005-065542 | 12/2003 |
| WO | WO 2004-010844 | 2/2004 |
| WO | WO 04/030726 | 4/2004 |
| WO | WO 04/052190 | 6/2004 |
| WO | WO 04/060455 | 7/2004 |
| WO | WO 04/098685 | 11/2004 |
| WO | WO 05/012873 | 2/2005 |
| WO | WO 2005-011489 | 2/2005 |

(56) References Cited

FOREIGN PATENT DOCUMENTS

| WO | WO 05/018443 | 3/2005 |
|---|---|---|
| WO | WO 05/026689 | 3/2005 |
| WO | WO 05/032400 | 4/2005 |
| WO | WO 06/017358 | 2/2006 |
| WO | WO 06/105146 | 10/2006 |
| WO | WO 2008-088490 | 12/2006 |
| WO | WO 08/028644 | 3/2008 |
| WO | WO 08/069931 | 6/2008 |
| WO | WO 08/079616 | 7/2008 |
| WO | WO 08/101217 | 8/2008 |
| WO | WO 08/138006 | 11/2008 |

OTHER PUBLICATIONS

Armour et al., *Application of Chronic Intravascular Blood Glucose Sensor in Dogs*, , Diabetes, vol. 39, Dec. 1990 pp. 1519-1526.

Asberg et al., *Hydrogels of a Conducting Conjugated Polymer as 3-D Enzyme Electrode*, Biosensors Bioelectronics, pp. 199-207 (2003).

Atanasov et al. 1994. Biosensor for continuos glucose monitoring. *Biotechnology and Bioengineering*, 43:262-266.

Baker et al. 1993. Dynamic concentration challenges for biosensor characterization. *Biosensors & Bioelectronics*, 8:433-441.

Bland et al. 1990. A note on the e of the intraclass correlation coefficient in the evaluation of agreement between two methods of measurement. *Comput. Biol. Med.*, 20(5):337-340.

Bott, A. W. A Comparison of Cyclic Voltammetryand Cyclic Staircase Voltammetry. Current Separations 1997, 16:1, 23-26.

Brauker et al. Sustained expression of high levels of human factor IX from human cells implanted within an immunoisolation device into athymic rodents. Hum Gene Ther 1998, 9, 879-888.

Dai et al., *Hydrogel Membranes with Mesh Size Asymmetry Based on the Gradient Crosslink of Poly(vinyl alcohol)*, Journal of Membrane Science 156 (1999) 67-79.

D'Arrigo et al. Poro-Si based bioreactors for glucose monitoring and drugs production. Proc. of SPIE 2003, 4982, 178-184.

El-Sa'Ad et al. Moisture Absorption by Epoxy Resins: the Reverse Thermal Effect. Journal of Materials Science 1990, 25, 3577-3582.

Fare et al. 1998. Functional characterization of a conducting polymer-based immunoassay system. *Biosensors & Bioelectronics*, 13(3-4):459-470.

Fraser et al. *Biosensors in the Body*, Continous in Vivo Monitoring, Wiley Series of Biomaterials Science and Engineering, 1997, Chapter 4, Principles of Long-term Fully Implantable Sensors with Emphasis on Radiotelemetric Monitoring of Blood Glucose from inside a Subcutaneous Foreign Body Capsule pp. 118-137.

Geller et al. use of an immunoisolation device for cell transplantation and tumor immunotherapy. Ann NY Acad Sci 1997, 831, 438-451.

Gerritsen et al. Influence of inflammatory cells and serum on the performance of implantable glucose sensors. J Biomed Mater Res 2001, 54, 69-75.

Godsland et al., *Maximizing the Success Rate of Minimal Model Insulin Sensivity Mearsurement in Humans: The Importance of Basal Glucose Levels*, , The Biochemical Society and the Medical Research Society, (2001) 1-9.

Gregg et al. *Cross-Linked Redox Gels Containing Glucose Oxidase for Amperometric Biosensor Applications*, Anal. Chem. (1990) 62, 258-263.

Heller, A., *Electrical Connection of Enzyme Redox Centers to Electrodes*, J. Phys. Chem. 1992, 96, pp. 3579-3587.

Hitchman, M. L. 1978. "Measurement of Dissolved Oxygen." In Elving et al. (Eds.). Chemical Analysis, vol. 49, Chap. 3, pp. 34-49, 59-123. New York: John Wiley & Sons.

Jensen et al. 1997. Fast wave forms for pulsed electrochemical detection of glucose by incorporation of reductive desorption of oxidation products. *Analytical Chemistry*, 69(9):1776-1781.

Kargol et al. Studies on the structural properties of porous membranes: measurement of linear dimensions of solutes. Biophys Chem 2001, 91, 263-271.

Kurnik et al. 1999. Application of the mixtures of experts algorithm for signal processing in a noninvasive glucose monitoring system. *Sensors and Actuators*, B 60:19-26.

Lee et al. Effects of pore size, void volume, and pore connectivity on tissue responses. Society for Biomaterials 1999, 25th Annual Meeting, 171.

Luong et al., *Solubilization of Multiwall Carbon Nanotubes by 3-Aminopropyltriethoxysilane Towards the Fabrication of Electrochemical Biosensors with Promoted Elecron Transfer*, Electronanalysis 16 No. 1-2, pp. 132-139 (2004).

Makale et al. 2003. Tissue window chamber system for validation of implanted oxygen sensors. *Am. J. Physiol. Heart Circ. Physiol.*, 284:H2288-2294.

Mangy et al. 1962. A galvanic cell oxygen analyzer. *Journal of Electroanalytical Chemistry*, 4:65-92.

McKean, et al. *A Telemetry Instrumentation System for Chronically Implanted Glucose and Oxygen Sensors*, Transactions on Biomedical Engineering vol. 35, No. 7 Jul. 1988 pp. 526-532.

Miller, A. Human monocyte/macrophage activation and interleukin 1 generation by biomedical polymers. J Biomed Mater Res 1988, 23, 713-731.

Miller et al. Generation of IL-1 like activity in response to biomedical polymer implants: a comparison of in vitro and in vivo models. J Biomed Mater Res 1989, 23, 1007-1026.

Miller et al. In vitro stimulation of fibroblast activity by factors generated from human monocytes activated by biomedical polymers. Journal of J Biomed Mater Res 1989, 23, 911-930.

Mowery et al. Preparation and characterization of hydrophobic polymeric films that are thromboresistant via nitric oxide release. Biomaterials 2000, 21, 9-21.

Nam et al. A novel fabrication method of macroporous biodegradable polymer scaffolds using gas foaming salt as a porogen additive. J Biomed Mater Res 2000, 53, 1-7.

Okuda, J.; Miwa, I. Mutarotase effect on micro determinations of D-glucose and its anomers with -D-glucose oxidase. Anal Biochem 1971, 43, 312-315.

Pickup et al., *Responses and Calibration of Amperometric Glucose Sensors Implanted in the Subcutaneous Tissue of Man*, ACTA Diabetol, pp. 143-148. (1993).

Ratner, B.D. Reducing capsular thickness and enhancing angiogenesis around implant drug release systems. J Control Release 2002, 78, 211-218.

Rhodes et al. 1994. Prediction of pocket-portable and implantable glucose enzyme electrode performance from combined species permeability and digital simulation analysis. *Analytical Chemistry*, 65(9):1520-1529.

Sakakida et al. *Development of Ferrocene-Mediated Needle-Type Glucose Sensor as a Measure of True Subcutaneous Tissue Glucose Concentrations*, Artif. Organs Today, vol. 2 No. 2, pp. 145-158 (1992).

Sakakida et al. *Ferrocene-Mediated Needle Type Glucose Sensor Covered with Newly Designed Biocompatible Membran*, Sensors and Actuators B, vol. 13-14, pp. 319-322 (1993).

Schmidt et al. 1993. Glucose concentration in subcutaneous extracellular space. *Diabetes Care*, 16(5):695-700.

Schmidtke, D. W.; Heller, A. Accuracy of the one-point in vivo calibration of "wired" glucose oxidase electrodes implanted in jugular veins of rats in periods of rapid rise and decline of the glucose concentration. Anal Chem 1998, 70, 2149-2155.

Shichiri et al. *Glycaemic Control in Pancreatectomized Dogs with a Wearable Artificial Endocrine Pancreas*, Diabetologia (1983) 24 pp. 179-184.

Shichiri et al., *Membrane Design for Extending the Long-Life of an Implantable Glucose Sensor*, Diab. Nutr. Metab., 2, pp. 309-313 (1989).

Shichiri et al., *Needle Type Glucose Sensor for Wearable Artificial Endocrine Pancreas*, Implantable Sensors for Closed-Loop Prosthetic Systems, Chapter 15, pp. 197-210.

(56) References Cited

OTHER PUBLICATIONS

Shichiri et al., *Telemetry Glucose Monitoring Device with Needle-Type Glucose Sensor: A Useful Tool for Blood Glucose Monitoring in Diabetic Individuals*, Diabetes Care, Inc. Vo. 9, No. 3, 1986 pp. 298-301.
Shults et al. *A Telemetry-Instrumentation System for Monitoring Multiple Subcutaneously Implanted Glucose Sensors*, Transactions on Biomedical Engineering vol. 41, No. 10 Oct. 1994. pp. 937-942.
Sieminski et al. Biomaterial-microvasculature interactions. Biomaterials 2000, 21, 2233-2241.
Sternberg et al. *Study and Development of Multilayer Needle-type Enzymebased Glucose Microsensors*, Biosensors vol. 4 pp. 27-40 (1988).
Tang et al. Fibrin(ogen) mediates acute inflammatory responses to biomaterials. J Exp Med 1993, 178, 2147-2156.
Tang et al. Inflammatory responses to biomaterials. Am J Clin Pathol 1995, 103, 466-471.
Tang et al. Mast cells mediate acute inflammatory responses to implanted biomaterials. Proc Natl Aced Sci U S A 1998, 95, 8841-8846.
Tang et al. Molecular determinants of acute inflammatory responses to biomaterials. J Clin Invest 1996, 97, 1329-1334.
Thompson et al., *In Vivo Probes: Problems and Perspectives*, Department of Chemistry, University of Toronto, Canada, pp. 255-261.
Tibell et al. Survival of macroencapsulated allogeneic parathyroid tissue one year after transplantation in nonimmunosuppressed humans. Cell Transplant 2001, 10, 591-9.
Trajanoski et al. 1998. Neural predictive controller for insulin delivery using the subcutaneous route. *IEEE Transactions on Biomedical Engineering*, 45(9):1122-1134.
Updike et al. 1982. Implanting the glucose enzyme electrode: Problems, progress, and alternative solutions. *Diabetes Care*, 5(3):207-212.
Velho et al., *Strategies for Calibrating a Subcutaneous Glucose Sensor*, Biomed. Biochim. 48, 11/12, 957-964.
Wade Jr., L.G. *Organic Chemistry*, Chapter 17, Reactions of Aromatic Compounds pp. 762-763.
Wilson et al., *Progress Toward the Development of an Implantable Sensor for Glucose*, Clinical Chemistry, vol. 38, No. 9, 1992 pp. 1613-1617.
Wood, W. et al., Hermetic Sealing with Epoxy. Mechanical Engineering Mar. 1990, 1-3.
Wu et al. 1999. In situ electrochemical oxygen generation with an immunoisolation device. Ann. N.Y. Acad. Sci., 875:105-125.
Yang, el al., *A Comparison of Physical Properties and Fuel Cell Performance of Nafion and Zirconium Phosphate/Nation Composite Membranes*, Journal of Membrane Science 237 (2004) 145-161.
Brooks, et al. "Development of an on-line glucose sensor for fermentation monitoring," Biosensors, 3:45-56 (1987/88).
Heller, "Electrical wiring of redox enzymes," Acc. Chem. Res., 23:128-134 (1990).
Kerner, et al. "The function of a hydrogen peroxide-detecting electroenzymatic glucose electrode is markedly impaired in human sub-cutaneous tissue and plasma," Biosensors & Bioelectronics, 8:473-482 (1993).
Koschinsky, et al. 1998. New approach to technical and clinical evaluation of devices for self-monitoring of blood glucose. Diabetes Care 11(8): 619-619.
Mastrototaro, et al. "An electroenzymatic glucose sensor fabricated on a flexible substrate," Sensors and Actuators B, 5:139-44 (1991).
Pickup, et al. "Implantable glucose sensors: choosing the appropriate sensor strategy," *Biosensors*, 3:335-346 (1987/88).
Pickup, et al. "In vivo molecular sensing in diabetes mellitus: an implantable glucose sensor with direct electron transfer," *Diabetologia*, 32:213-217 (1989).
Rebrin, et al. "Automated feedback control of subcutaneous glucose concentration in diabetic dogs," Diabetologia, 32:573-76 (1989).

Shaw, et al. "In vitro testing of a simply constructed, highly stable glucose sensor suitable for implantation in diabetic patients," Biosensors & Bioelectronics, 6:401-406 (1991).
Turner and Pickup, "Diabetes mellitus: biosensors for research and management," Biosensors, 1:85-115 (1985).
Wagner, et al. 1998. Continuous amperometric monitoring of glucose in a brittle diabetic chimpanzee with a miniature subcutaneous electrode. Proc. Natl. Acad. Sci. A, 95:6379-6382.
Office Action dated May 18, 2007 in U.S. Appl. No. 11/543,707.
Office Action dated May 23, 2007 in U.S. Appl. No. 11/543,539.
Office Action dated May 18, 2007 in U.S. Appl. No. 11/543,683.
Office Action dated Jun. 5, 2007 in U.S. Appl. No. 11/543,734.
Office Action dated Sep. 21, 2007 in U.S. Appl. No. 10/838,912.
Office Action dated May 17, 2007 in U.S. Appl. No. 11/077,759.
Office Action dated Oct. 9, 2007 in U.S. Appl. No. 11/077,883.
Office Action dated Jul. 27, 2007 in U.S. Appl. No. 11/077,714.
Office Action dated Apr. 10, 2007 in U.S. Appl. No. 11/077,714.
Office Action dated Oct. 11, 2006 in U.S. Appl. No. 11/077,714.
Office Action dated Jan. 30, 2007 in U.S. Appl. No. 11/077,763.
Office Action dated Sep. 25, 2007 in U.S. Appl. No. 11/334,876.
Answers.com. "xenogenic." The American Heritage Stedman's Medical Dictionary. Houghton Mifflin Company, 2002. Answers.com Nov. 7, 2006 http://www. Answers.com/topic/xenogenic.
Brauker, et al. 1995. Neovascularization of synthetic membranes directed by membrane Microarchitecture. J. Biomed Mater Res 29:1517-1524.
Cameron, et al. 1997. Micromodular Implants to provide electrical stimulation of paralyzed muscles and limbs. IEEE Transactions on Biomedical Engineering 44(9):781-790.
Gilligan, et al. 1994. Evaluation of a subcutaneous glucose sensor out to 3 months in a dog model. Diabetes Care 17(8):882-887.
Jeutter, et al. 1993. Design of a radio-linked implantable cochlear prosthesis using surface acoustic wave devices. IEEE Transactions on ultrasonics, ferroelectrics and frequency control 40(5):469-477.
Joung et al. 1998. An energy transmission system for an artificial heart using leakage inductance compensation of transcutaneous transformer. IEEE Transactions on Power Electronics 13(6):1013-1022.
Loffler, et al. 1995. Separation and determination of traces of ammonia in air by means of chromatomembrane cells. Fresenius J Anal Chem 352:613-614.
Matsuki. 1994. Energy transfer system utilizing amorphous wires for implantable medical devices. IEEE Transactions on Magnetics 31(2):1276-1282.
Miller, et al. 1993. Development of an autotuned transcutaneous energy transfer system ASAIO Journal 39:M706-M710.
Panetti 2002. Differential effects of sphingosine 1-phosphate and lysophosphatidic acid on endothelial cells. Biochimica et Biophysica Acta 1582:190-196.
Philips. 1995. A high capacity transcutaneous energy transmission system. ASAIO Journal 41:M259-M262.
Pineda, et al. 1996. Bone regeneration with resorbable polymeric membranes. III. Effect of poly(L-lactide) membrane pore size on the bone healing process in large defects. J. Biomedical Materials Research 31:385-394.
Shichiri, et al., Needle Type Glucose Sensor for Wearable Artificial Endocrine Pancreas, Implantable Sensors for Closed-Loop Prosthetic Systems, Chapter 15, pp. 197-210, 1985.
Smith, et al. 1998. An externally powered, multichannel, implantable stimulator-telemeter for control of paralyzed muscle. IEEE Transactions on Biomedical Engineering 45(4):463-475.
Thompson, et al., In Vivo Probes: Problems and Perspectives, Department of Chemistry, University of Toronto, Canada, pp. 255-261, 1986.
Velho, et al., Strategies for Calibrating a Subcutaneous Glucose Sensor, Biomed. Biochim. 48, 11/12, 957-964, 1989.
Wade Jr., L.G. Organic Chemistry, Chapter 17, Reactions of Aromatic Compounds pp. 762-763, 1987.
Zhang, et al. 1994. Elimination of the acetaminophen interference in an implantable glucose sensor. Analytical Chemistry 66(7):1183-1188.

(56) References Cited

OTHER PUBLICATIONS

Ziaie, et al. 1997. A single-channel implantable microstimulator for functional neuromuscular stimulation. IEEE Transactions on Biomedical Engineering 44(10):909-920.
Office Action dated Jan. 28, 2008 in U.S. Appl. No. 11/077,715.
Office Action dated Jul. 26, 2007 in U.S. Appl. No. 11/077,715.
Office Action dated Apr. 10, 2007 in U.S. Appl. No. 11/077,715.
Office Action dated Oct. 31, 2006 in U.S. Appl. No. 11/077,715.
Office Action dated Apr. 9, 2003 in U.S. Appl. No. 09/916,386.
Office Action dated Dec. 7, 1998 in U.S. Appl. No. 08/811,473.
Office Action dated Jan. 23, 2008 in U.S. Appl. No. 09/447,227.
Office Action dated Jul. 17, 2007 in U.S. Appl. No. 09/447,227.
Office Action dated Mar. 9, 2007 in U.S. Appl. No. 09/447,227.
Office Action dated Aug. 1, 2006 in U.S. Appl. No. 09/447,227.
Office Action dated Apr. 4, 2006 in U.S. Appl. No. 09/447,227.
Office Action dated Sep. 22, 2005 in U.S. Appl. No. 09/447,227.
Office Action dated Nov. 28, 2003 in U.S. Appl. No. 09/447,227.
Office Action dated Jul. 9, 2003 in U.S. Appl. No. 09/447,227.
Office Action dated Jan. 16, 2003 in U.S. Appl. No. 09/447,227.
Office Action dated Jul. 15, 2002 in U.S. Appl. No. 09/447,227.
Office Action dated Jan. 17, 2002 in U.S. Appl. No. 09/447,227.
Office Action dated Aug. 15, 2001 in U.S. Appl. No. 09/447,227.
Office Action dated Dec. 26, 2007 in U.S. Appl. No. 11/021,046.
Office Action dated Aug. 14, 2001 in U.S. Appl. No. 09/489,588.
Office Action dated Feb. 27, 2002 in U.S. Appl. No. 09/489,588.
Office Action dated Jun. 12, 12003 in U.S. Appl. No. 09/489,588.
Office Action dated Sep. 21, 2004 in U.S. Appl. No. 10/657,843.
Office Action dated Sep. 21, 2004 in U.S. Appl. No. 09/916,858.
Office Action dated Mar. 22, 2004 in U.S. Appl. No. 09/916,858.
Office Action dated Aug. 14, 2006 in U.S. Appl. No. 11/039,269.
Office Action dated Feb. 24, 2006 in U.S. Appl. No. 11/039,269.
Office Action dated Nov. 2, 2005 in U.S. Appl. No. 11/039,269.
Office Action dated May 4, 2005 in U.S. Appl. No. 11/039,269.
Office Action dated Feb. 24, 2006 in U.S. Appl. No. 10/646,333.
Office Action dated Jun. 6, 2003 in U.S. Appl. No. 10/646,333.
Office Action dated Sep. 22, 2004 in U.S. Appl. No. 10/646,333.
Office Action dated Oct. 16, 2006 in U.S. Appl. No. 10/647,065.
Office Action dated May 21, 2007 in U.S. Appl. No. 10/842,716.
Office Action dated Nov. 17, 2006 in U.S. Appl. No. 10/842,716.
Office Action dated May 23, 2007 in U.S. Appl. No. 11/055,779.
Office Action dated Oct. 24, 2007 in U.S. Appl. No. 11/055,779.
Office Action dated Dec. 12, 007 in U.S. Appl. No. 11/543,707.
Office Action dated Dec. 12, 2007 in U.S. Appl. No. 11/543,539.
Office Action dated Dec. 12, 2007 in U.S. Appl. No. 11/543,683.
Office Action dated Dec. 17, 2007 in U.S. Appl. No. 11/543,734.
Office Action dated Nov. 1, 2007 in U.S. Appl. No. 11/034,343.
Office Action dated Jan. 10, 2008 in U.S. Appl. No. 11/077,714.
Office Action dated Jan. 3, 2008 in U.S. Appl. No. 11/157,746.
Office Action dated Oct. 4, 2006 in U.S. Appl. No. 11/334,876.
ISR and WO for PCT/US06/31496, filed Aug. 10, 2006.
International Search Report dated Feb. 20, 2007 for PCT International Application No. PCT/US06/19889.
Velho, et al. Strategies for calibrating a subcutaneous glucose sensor. Biomed Biochim Acta 48(11/12):957-964, (1989).
Wade Jr., L.G. Organic Chemistry, Chapter 17, Reactions of Aromatic Compounds pp. 762-763, (2003).
Shichiri et al. Needle-type Glucose Sensor for Wearable Artificial Endocrine Pancreas in Implantable Sensors 197-210 (1985).
Thompson, et al., In Vivo Probes: Problems and Perspectives, Department of Chemistry, University of Toronto, Canada, pp. 255-261 (1986).
Bindra et al. 1991. Design and in Vitro Studies of a Needle-Type Glucose Senso for Subcutaneous Monitoring. Anal. Chem 63:1692-96.
Bobbioni-Harsch et al. 1993. Lifespan of subcutaneous glucose sensors and their performances during dynamic glycaemia changes in rats, J. Biomed. Eng. 15:457-463.
Bode, B. W. 2000. Clinical utility of the continuous glucose monitoring system. Diabetes Technol Ther, 2(Suppl 1):S35-41.
Cass et al. "Ferrocene-mediated enzyme electrodes for amperonnetric determination of glucose," Anal. Chem., 36:667-71 (1984).
Chia et al. 2004. Glucose sensors: toward closed loop insulin delivery. Endocrinol Metab Clin North Am 33:175-95.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Davies, et al. 1992. Polymer membranes in clinical sensor applications. I. An overview of membrane function, Biomaterials, 13(14):971-978.
El Degheidy et al. 1986. Optimization of an implantable coated wire glucose sensor. J. Biomed Eng. 8:121-129.
Fischer et al. 1995. Hypoglycaemia-warning by means of subcutaneous electrochemical glucose sensors: an animal study, Horm. Metab. Rese. 27:53.
Frost et al. 2002. Implantable chemical sensors for real-time clinical monitoring: Progress and challenges. Current Opinion in Chemical Biology 6:633-641.
Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," Diabetes Care, 17(5): 387-396.
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Johnson (1991). "Reproducible electrodeposition of biomolecules for the fabrication of miniature electroenzymatic biosensors," *Sensors and Actuators B*, 5:85-89.
Johnson et al. 1992. In vivo evaluation of an electroenzymatic glucose sensor implanted in subcutaneous tissue. Biosensors & Bioelectronics, 7:709-714.
Kawagoe et al. 1991. Enzyme-modified organic conducting salt microelectrode, Anal. Chem. 63:2961-2965.
Ladd et al., Structure Determination by X-ray Crystallography, 3rd ed. Plenum, 1996, Ch. 1, pp. xxi-xxiv and -58.
Maidan et al. 1992. Elimination of Electrooxidizable Interferent-Produced Currents in Amperometric Biosensors, Analytical Chemistry, 64:2889-2896.
Moatti-Sirat et al. 1992. Towards continuous glucose monitoring: in vivo evaluation of a miniaturized glucose sensor implanted for several days in rat subcutaneous tissue. Diabetologia 35:224-230.
Moatti-Sirat et al., Reduction of acetaminophen interference in glucose sensors by a composite Nafion membrane: demonstration in rats and man, Diabetologia 37(6):610-616, Jun. 1994.
Morff et al. 1990. Microfabrication of reproducible, economical, electroenzymatic glucose sensors, Annual International Conference of the IEEE Engineering in Medicine and Biology Society, 12(2):0483-0484.
Murphy, et al. 1992. Polymer membranes in clinical sensor applications. II. The design and fabrication of permselective hydrogels for electrochemical devices, Biomaterials, 13(14):979-990.
Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.
Pishko et al. "Amperometric glucose microelectrodes prepared through immobilization of glucose oxidase in redox hydrogels," Anal. Chem., 63:2268-72 (1991).
Poitout, et al. 1991. In Vitro and in Vivo Evaluation in Dogs of a Miniaturized Glucose Sensor, ASAIO Transactions, 37:M298-M300.
Rebrin et al. 1992. Subcutaenous glucose monitoring by means of electrochemical sensors: fiction or reality? J. Biomed. Eng. 14:33-40.
Sharkawy et al. 1996. Engineering the tissue which encapsulates subcutaneous implants. I. Diffusion properties, J Biomed Mater Res, 37:401-412.
Sokol et al. 1980, Immobilized-enzyme rate-determination method for glucose analysis, Clin. Chem. 26(1):89-92.

(56) References Cited

OTHER PUBLICATIONS

Thome et al. 1995. Can the decrease in subcutaneous glucose concentration precede the decrease in blood glucose level? Proposition for a push-pull kinetics hypothesis, Horm. Metab. Res. 27:53.
Thomé-Duret et al. 1996. Modification of the sensitivity of glucose sensor implanted into subcutaneous tissue. Diabetes Metabolism, 22:174-178.
Updike et al. 1979. Continuous glucose monitor based on an immobilized enzyme electrode detector. J Lab Clin Med, 93(4):518-527.
Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons, pp. 117-137.
von Woedtke et al. 1989. In situ calibration of implanted electrochemical glucose sensors. Biomed Biochim. Acta 48(11/12):943-952.
Ward et al. 1999. Assessment of chronically implanted subcutaneous glucose sensors in dogs: The effect of surrounding fluid masses. ASAIO Journal, 45:555-561.
Ward et al. 2000. Rise in background current over time in a subcutaneous glucose sensor in the rabbit: Relevance to calibration and accuracy. Biosensors & Bioelectronics, 15:53-61.
Yang et al (1996). "A glucose biosensor based on an oxygen electrode: In-vitro performances in a model buffer solution and in blood plasma," Biomedical Instrumentation & Technology, 30:55-61.
Zhang et al (1993). Electrochemical oxidation of H2O2 on Pt and Pt + Ir electrodes in physiological buffer and its applicability to H2O2-based biosensors. J. Electroanal. Chem., 345:253-271.
Zhu et al. (1994). "Fabrication and characterization of glucose sensors based on a microarray H2O2 electrode." Biosensors & Bioelectronics, 9: 295-300.
Office Action dated Feb. 4, 2009 in U.S. Appl. No. 10/768,889.
Office Action dated Jun. 19, 2008 in U.S. Appl. No. 11/021,162.
Office Action dated Dec. 11, 2008 in U.S. Appl. No. 09/447,227.
Office Action dated Jun. 12, 2008 in U.S. Appl. No. 09/447,227.
Office Action dated Jun. 23, 2008 in U.S. Appl. No. 11/021,046.
Office Action dated Feb. 4, 2009 in U.S. Appl. No. 11/021,046.
Office Action dated Jun. 5, 2008 in U.S. Appl. No. 10/846,150.
Office Action dated Dec. 9, 2008 in U.S. Appl. No. 10/846,150.
Office Action dated Sep. 29, 2008 in U.S. Appl. No. 12/037,830.
Office Action dated Feb. 26, 2009 in U.S. Appl. No. 12/037,830.
Office Action dated Sep. 29, 2008 in U.S. Appl. No. 12/037,812.
Office Action dated Apr. 1, 2009 in U.S. Appl. No. 12/037,812.
Office Action dated Oct. 8, 2008 in U.S. Appl. No. 10/842,716.
Office Action dated Oct. 8, 2008 in U.S. Appl. No. 10/896,637.
Office Action dated Mar. 5, 2009 in U.S. Appl. No. 10/896,637.
Office Action dated Jan. 22, 2009 in U.S. Appl. No. 11/692,154.
Office Action dated Jul. 10, 2008 in U.S. Appl. No. 11/034,343.
Office Action dated Dec. 30, 2008 in U.S. Appl. No. 11/034,343.
Office Action dated Mar. 24, 2008 in U.S. Appl. No. 10/838,912.
Office Action dated Jul. 16, 2008 in U.S. Appl. No. 10/838,912.
Office Action dated Jun. 5, 2008 in U.S. Appl. No. 10/838,909.
Office Action dated Mar. 16, 2009 in U.S. Appl. No. 10/838,909.
Office Action dated Mar. 31, 2008 in U.S. Appl. No. 11/077,759.
Office Action dated Jul. 10, 2008 in U.S. Appl. No. 11/077,759.
Office Action dated May 12, 2008 in U.S. Appl. No. 11/077,715.
Office Action dated Nov. 12, 2008, 2008 in U.S. Appl. No. 11/077,715.
Office Action dated Jun. 24, 2008 in U.S. Appl. No. 11/077,883.
Office Action dated Sep. 18, 2008 in U.S. Appl. No. 11/077,883.
Office Action dated Apr. 6, 2009 in U.S. Appl. No. 11/077,883.
Office Action dated Sep. 18, 2007 in U.S. Appl. No. 11/078,230.
Office Action dated Sep. 5, 2008 in U.S. Appl. No. 11/078,230.
Office Action dated Jan. 26, 2009 in U.S. Appl. No. 11/078,230.
Office Action dated May 5, 2008 in U.S. Appl. No. 11/078,232.
Office Action dated Nov. 12, 2008 in U.S. Appl. No. 11/078,232.
Office Action dated Mar. 5, 2009 in U.S. Appl. No. 11/078,232.
Office Action dated May 5, 2008 in U.S. Appl. No, 11/077,713.
Office Action dated Feb. 10, 2009 in U.S. Appl. No. 11/077,713.
Office Action dated Sep. 16, 2008 in U.S. Appl. No. 11/077,714.
Office Action dated Apr. 16, 2009 in U.S. Appl. No. 11/077,714.
Office Action dated Apr. 21, 2008 in U.S. Appl. No. 11/077,643.
Office Action dated Oct. 1, 2008 in U.S. Appl. No. 11/077,643.
Office Action dated Mar. 11, 2009 in U.S. Appl. No. 11/077,643.
Office Action dated Dec. 1, 2008 in U.S. Appl. No. 11/503,367.
IPRP for PCT/US05/024993 filed Jul. 13, 2005.
ISR and WO for PCT/US05/024993 filed Jul. 13, 2005.
Office Action dated May 1, 2008 in U.S. Appl. No. 11/157,746.
Office Action dated Jun. 26, 2008 in U.S. Appl. No. 11/157,365.
Office Action dated Jan. 7, 2009 in U.S. Appl. No. 11/157,365.
Office Action dated Jun. 30, 2008 in U.S. Appl. No. 11/360,252.
Office Action dated Jan. 29, 2009, in U.S. Appl. No. 11/360,252.
Office Action dated Aug. 11, 2008 in U.S. Appl. No. 11/360,819.
Office Action dated Dec. 26, 2008 in U.S. Appl. No. 11/360,819.
Office Action dated Nov. 28, 2008 in U.S. Appl. No. 11/333,837.
Office Action dated Nov. 28, 2008 in U.S. Appl. No. 11/360,250.
Bellucci et al. Jan. 1986. Electrochemical behaviour of graphite-epoxy composite materials (GECM) in aqueous salt solutions, Journal of Applied Electrochemistry, 16(1):15-22.
Bode, B. W. 2000. Clinical utility of the continuous glucose monitoring system. Diabetes Technol Ther, 2(Suppl 1):S35-41.
Reach et al. 1992. Can continuous glucose monitoring be used for the treatment of diabetes? Analytical Chemistry 64(5):381-386.
Office Action dated May 26, 2009 in U.S. Appl. No. 11/077,759.
Office Action dated Jun. 15, 2009 in U.S. Appl. No. 11/360,250.
Office Action dated Jun. 29, 2009 in U.S. Appl. No. 11/333,837.
Office Action dated Jul. 8, 2009 in U.S. Appl. No. 11/692,154.
Office Action dated Jul. 20, 2009 in U.S. Appl. No. 10/896,637.
Office Action dated Jul. 21, 2009 in U.S. Appl. No. 11/078,232.
Office Action dated Jul. 21, 2009 in U.S. Appl. No. 11/157,365.
Office Action dated Jul. 23, 2009, in U.S. Appl. No. 11/360,252.
Aalders et al. 1991. Development of a wearable glucose sensor; studies in healthy volunteers and in diabetic patients. The International Journal of Artificial Organs 14(2):102-108.
Abe et al. 1992. Characterization of glucose microsensors for intracellular measurements. Anal. Chem. 64(18):2160-2163.
Abel et al. 1984. Experience with an implantable glucose sensor as a prerequisite of an artificial beta cell, Biomed. Biochim. Acta 43(5):577-584.
Abel et al. 2002. Biosensors for in vivo glucose measurement: can we cross the experimental stage. Biosens Bioelectron 17:1059-1070.
Alcock & Turner. 1994. Continuous Analyte Monitoring to Aid Clinical Practice. IEEE Engineering in Med. & Biol. Mag. 13:319-325.
American Heritage Dictionary, 4th Edition. 2000. Houghton Mifflin Company, p. 82.
Amin et al. 2003. Hypoglycemia prevalence in prepubertal children with type 1 diabetes on standard insulin regimen: Use of continuous glucose monitoring system. Diabetes Care 26(3):662-667.
Atanasov et al. 1997. Implantation of a refillable glucose monitoring-telemetry device. Biosens Bioelectron 12:669-680.
Aussedat et al. 1997. A user-friendly method for calibrating a subcutaneous glucose sensor-based hypoglycaemic alarm. Biosensors & Bioelectronics 12(11):1061-1071.
Bailey et al. 2007. Reduction in hemoglobin A1c with real-time continuous glucose monitoring: results from a 12-week observational study. Diabetes Technology & Therapeutics 9(3):203-210.
Beach et al. 1999. Subminiature implantable potentiostat and modified commercial telemetry device for remote glucose monitoring. IEEE Transactions on Instrumentation and Measurement 48(6):1239-1245.
Bessman et al., Progress toward a glucose sensor for the artificial pancreas, Proceedings of a Workshop on Ion-Selective Microelectrodes, Jun. 4-5, 1973, Boston, MA, 189-197.
Biermann et al. 2008. How would patients behave if they were continually informed of their blood glucose levels? A simulation study using a "virtual" patient. Diab. Thechnol. & Therapeut., 10:178-187.

(56) References Cited

OTHER PUBLICATIONS

Bindra et al. 1989. Pulsed amperometric detection of glucose in biological fluids at a surface-modified gold electrode. Anal Chem 61:2566-2570.
Bisenberger et al. 1995. A triple-step potential waveform at enzyme multisensors with thick-film gold electrodes for detection of glucose and sucrose. Sensors and Actuators, B 28:181-189.
Bode et al. 2000. Using the continuous glucose monitoring system to improve the management of type 1 diabetes. Diabetes Technology & Therapeutics, 2(Suppl 1):S43-48.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bowman, L.; Meindl, J. D. 1986. The packaging of implantable integrated sensors. IEEE Trans Biomed Eng BME33(2):248-255.
Brauker et al. Jun. 27, 1996. Local Inflammatory Response Around Diffusion Chambers Containing Xenografts Transplantation 61(12):1671-1677.
Brauker et al. 2001. Unraveling Mysteries at the Biointerface: Molecular Mediator of Inhibition of Blood vessel Formation in the Foreign Body Capsule Revealed. Surfacts Biomaterials 6. 1;5.
Braunwald, 2008. Biomarkers in heart failure. *N. Engl. J. Med.*, 358: 2148-2159.
Bremer et al. 2001. Benchmark data from the literature for evaluation of new glucose sensing technologies. Diabetes Technology & Therapeutics 3(3):409-418.
Bruckel et al. 1989. In vivo measurement of subcutaneous glucose concentrations with an enzymatic glucose sensor and a wick method. Klin Wochenschr 67:491-495.
Brunner et al. 1998. Validation of home blood glucose meters with respect to clinical and analytical approaches. Diabetes Care 21(4):585-590.
Cai et al. 2004. A wireless, remote query glucose biosensor based on a pH-sensitive polymer. Anal Chem 76(4):4038-4043.
Campanella et al. 1993. Biosensor for direct determination of glucose and lactate in undiluted biological fluids. Biosensors & Bioelectronics 8:307-314.
Candas et al (1994). "An adaptive plasma glucose controller basedon a nonlinear insulin/glucose model." *IEEE Transactions on Biomedical Engineering*, 41(2): 116-124.
Cassidy et al., Apr. 1993. Novel electrochemical device for the detection of cholesterol or glucose, Analyst, 118:415-418.
Cellulose Acetate Product Description, Product No. 419028, Sigma-Aldrich Corp., St. Louis, MO. 2005.
Chase et al.2001. Continuous subcutaneous glucose monitoring in children with type 1 diabetes. Pediatrics 107:222-226.
Chatterjee et al. 1997. Poly(ether Urethane) and poly(ether urethane urea) membranes with high $H_2S/CH_4$ selectivity, Journal of Membrane Science 135:99-106.
Chen et al. 2006. A noninterference polypyrrole glucose biosensor. Biosensors and Bioelectronics 22:639-643.
Ciba® Irgacure 2959 Photoinitiator Product Description, Ciba Specialty Chemicals Inc., Basel, Switzerland.
Claremont et al. 1986. Subcutaneous implantation of a ferrocene-mediated glucose sensor in pigs. Diabetologia 29:817-821.
Claremont et al. Jul. 1986. Potentially-implantable, ferrocene-mediated glucose sensor. J. Biomed. Eng. 8:272-274.
Clark et al., 1981. One-minute electrochemical enzymic assay for cholesterol in biological materials, Clin. Chem. 27(12):1978-1982.
Clark et al. 1988. Long-term stability of electroenzymatic glucose sensors implanted in mice. Trans Am Soc Artif Intern Organs 34:259-265.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.

Colowick et al. 1976. Methods in Enzymlology, vol. XLIV, Immobilized Enzymes. New York: Academic Press.
Cox et al. 1985. Accuracy of perceiving blood glucose in IDDM. Diabetes Care 8(6):529-536.
Csoregi et al., 1994. Design, characterization, and one-point in vivo calibration of a subcutaneously implanted glucose electrode. Anal Chem. 66(19):3131-3138.
Danielsson et al. 1988. Enzyme thermistors, Methods in Enzymology, 137:181-197.
Dassau et al., In silico evaluation platform for artifical pancreatic β-cell development—a dynamic simulator for closed loop control with hardware-in-the-loop, Diabetes Technology & Therapeutics, 11(3):1-8, 2009.
Davis et al. 1983. Bioelectrochemical fuel cell and sensor based on a quinoprotein, alcohol dehydrogenase. *Enzyme Microb. Technol.*, vol. 5, September, 383-388.
Direct 30/30® meter (Markwell Medical) (Catalog).
Dixon et al. 2002. Characterization in vitro and in vivo of the oxygen dependence of an enzyme/polymer biosensor for monitoring brain glucose. Journal of Neuroscience Methods 119:135-142.
DuPont[1] Dimension AR® (Catalog), 1998.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
Ernst et al. 2002. Reliable glucose monitoring through the use of microsystem technology. Anal. Bioanal. Chem. 373:758-761.
Fahy et al., An analysis: hyperglycemic intensive care patients need continuous glocuse monitoring—easier said than done, Journal of Diabetese Science and Technology, 2(2):201-204, Mar. 2008.
Feldman et al. 2003. A continuous glucose sensor based on wired enzyme technology—results from a 3-day trial in patients with type 1 diabetes. Diabetes Technol Ther 5(5):769-779.
Fischer et al. 1987. Assessment of subcutaneous glucose concentration: validation of the wick technique as a reference for implanted electrochemical sensors in normal and diabetic dogs, Diabetologia 30:940-945.
Fischer et al. 1989. Oxygen Tension at the Subcutaneous Implantation Site of Glucose Sensors. Biomed. Biochem 11/12:965-972.
Freedman et al. 1991. Statistics, Second Edition, W.W. Norton & Company, p. 74.
Frohnauer et al. 2001. Graphical human insulin time-activity profiles using standardized definitions. Diabetes Technology & Therapeutics 3(3):419-429.
Gabbay et al. 2008. Optical coherence tomography-based continuous noninvasive glucose monitoring in patients with diabetes. Diab. Thechnol. & Therapeut., 10:188-193.
Ganesan et al., Gold layer-based dual crosslinking procedure of glucose oxidase with ferrocene monocarboxylic acid provides a stable biosensor, Analytical Biochemistry 343:188-191, 2005.
Ganesh et al., Evaluation of the VIA@ blood chemistry monitor for glucose in healthy and diabetic volunteers, Journal of Diabetese Science and Technology, 2(2):182-193, Mar. 2008.
Gao et al. 1989. Determination of Interfacial parameters of cellulose acetate membrane materials by HPLC, *J. Liquid Chromatography*, VI. 12, n. 11, 2083-2092.
Garg et al. 2004. Improved Glucose Excursions Using an Implantable Real-Time continuous Glucose Sensor in Adults with Type I Diabetes. Diabetes Care 27:734-738.
Gerritsen et al. 1999. Performance of subcutaneously implanted glucose sensors for continuous monitoring. The Netherlands Journal of Medicine 54:167-179.
Gerritsen, M. 2000. Problems associated with subcutaneously implanted glucose sensors. Diabetes Care 23(2):143-145.
Gilligan et al. 2004, Feasibility of continuous long-term glucose monitoring from a subcutaneous glucose sensor in humans. Diabetes Technol Ther 6:378-386.

(56) References Cited

OTHER PUBLICATIONS

Gouda et al., Jul. 4, 2003. Thermal inactivation of glucose oxidase, The Journal of Biological Chemistry, 278(27):24324-24333.
Gough et al. 2000. Immobilized glucose oxidase in implantable glucose sensor technology. Diabetes Technology & Therapeutics 2(3):377-380.
Gough et al. 2003. Frequency characterization of blood glucose dynamics. Annals of Biomedical Engineering 31:91-97.
Gross et al. 2000. Efficacy and reliability of the continuous glucose monitoring system. Diabetes Technology & Therapeutics, 2(Suppl 1):S19-26.
Gross et al. 2000. Performance evaluation of the MiniMed® continuous glucose monitoring system during patient home use. Diabetes Technology & Therapeutics 2(1):49-56.
Guerci et al., Clinical performance of CGMS in type 1 diabetic patents treated by continuous subcutaneous insulin infusion using insulin analogs, Diabetes Care, 26:582-589, 2003.
Guo et al., Modification of cellulose acetate ultrafiltration membrane by gamma ray radiation, Shuichuli Jishi Bianji Weiyuanhui, 23(6):315-318, 1998 (Abstract only).
Hall et al. 1998. Electrochemical oxidation of hydrogen peroxide at platinum electrodes. Part I: An adsorption-controlled mechanism. Electrochimica Acta, 43(5-6):579-588.
Hall et al. 1998. Electrochemical oxidation of hydrogen peroxide at platinum electrodes. Part II: Effect of potential. Electrochimica Acta 43(14-15):2015-2024.
Hall et al. 1999. Electrochemical oxidation of hydrogen peroxide at platinum electrodes. Part III: Effect of temperature. Electrochimica Acta, 44:2455-2462.
Hall et al. 1999. Electrochemical oxidation of hydrogen peroxide at platinum electrodes. Part IV: Phosphate buffer dependence. Electrochimica Acta, 44:4573-4582.
Hall et al. 2000. Electrochemical oxidation of hydrogen peroxide at platinum electrodes. Part V: Inhibition by chloride. Electrochimica Acta, 45:3573-3579.
Hamilton Syringe Selection Guide. 2006. Syringe Selection. www.hamiltoncompany.com.
Harrison et al. 1988. Characterization of perfluorosulfonic acid polymer coated enzyme electrodes and a miniaturized integrated potentiostat for glucose analysis in whole blood. Anal. Chem. 60:2002-2007.
Heller, A. 1999. Implanted electrochemical glucose sensors for the management of diabetes. Annu Rev Biomed Eng 1:153-175.
Heller, A. 2003. Plugging metal connectors into enzymes. Nat Biotechnol 21:631-2.
Hoel, Paul G. 1976. Elementary Statistics, Fourth Edition. John Wiley & Sons, Inc.. pp. 113-114.
Hrapovic et al. 2003. Picoamperometric detection of glucose at ultrasmall platinum-based biosensors: preparation and characterization. Anal Chem 75:3308-3315.
http://www.merriam-webster.com/dictionary, definition for "aberrant," Aug. 19, 2008, p. 1.
Huang et al. A 0.5mV passive telemetry IC for biomedical applications. Swiss Federal Institute of Technology. 4 pp.
Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum E.
Hunter et al. 2000. Minimally Invasive Glucose Sensor and Insulin Delivery System. MIT Home Automation and Healthcare Consortium. Progress Report No. 25.
Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Compl.
Jeutter, D. C. 1982. A transcutaneous implanted battery recharging and biotelemeter power switching system. IEEE Trans Biomed Eng 29:314-321.

Johnson, R.C. et al., Abstract: Neovascularization of cell transplantation devices: Role of membrane architecture and encapsulated tissue, Abstracts of Papers, Am. Chem. Soc., 1997, 214:2 p. 305-PMSE.
Jovanovic, L. 2000. The role of continuous glucose monitoring in gestational diabetes mellitus. Diabetes Technology & Therapeutics, 2 Suppl 1, S67-71.
Kacaniklic May-Jun. 1994. Electroanalysis, 6(5-6):381-390.
Kamath et al. Calibration of a continuous glucose monitor: effect of glucose rate of change, Eighth Annual Diabetes Technology Meeting, Nov. 13-15, 2008, p. A88.
Kang et al. 2003. In vitro and short-term in vivo characteristics of a Kel-F thin film modified glucose sensor. Anal Sci 19:1481-1486.
Karube et al. 1993. Microbiosensors for acetylcholine and glucose. Biosensors & Bioelectronics 8:219-228.
Kaufman. 2000. Role of the continuous glucose monitoring system in pediatric patients. Diabetes Technology & Therapeutics 2(1):S-49-S-52.
Kaufman et al. 2001. A pilot study of the continuous glucose monitoring system. Diabetes Care 24(12):2030-2034.
Keedy et al. 1991. Determination of urate in undiluted whole blood by enzyme electrode. *Biosensors & Bioelectronics*, 6: 491-499.
Kerner et al. 1988. A potentially implantable enzyme electrode for amperometric measurement of glucose, Horm Metab Res Suppl. 20:8-13.
Kiechle, F.L. 2001. The impact of continuous glucose monitoring on hospital point-of-care testing programs. Diabetes Technol Ther 3:647-649.
Klueh et al. 2003. Use of Vascular Endothelia Cell Growth Factor Gene Transfer to Enhance Implantable Sensor Function in Vivo, Biosensor Function and Vegf-Gene Transfer, pp. 1072-1086.
Klueh et al. 2007. Inflammation and glucose sensors: use of dexamethasone to extend glucose sensor function and life span in vivo. Journal of Diabetes Science and Technology 1(4):496-504.
Ko, Wen H. 1985. Implantable Sensors for Closed-Loop Prosthetic Systems, Futura Pub. Co., Inc., Mt. Kisco, NY, Chapter 15:197-210.
Kondo et al. 1982. A miniature glucose sensor, implantable in the blood stream. Diabetes Care. 5(3):218-221.
Koschinsky et al. 2001. Sensors for glucose monitoring: Technical and clinical aspects. Diabetes Metab. Res. Rev. 17:113-123.
Kost et al. 1985. Glucose-sensitive membranes containing glucose oxidase: activitiy, swelling, and permeability studies, Journal of Biomedical Materials Research 19:1117-1133.
Koudelka et al. 1989. In vivo response of microfabricated glucose sensors to glycemia changes in normal rats. Biomed Biochim Acta 48(11-12):953-956.
Koudelka et al. 1991. In-vivo behaviour of hypodermically implanted microfabricated glucose sensors. Biosensors & Bioelectronics 6:31-36.
Kraver et al. 2001. A mixed-signal sensor interface microinstrument. Sensors and Actuators A 91:266-277.
Kruger et al. 2000. Psychological motivation and patient education: A role for continuous glucose monitoring. Diabetes Technology & Therapeutics, 2(Suppl 1):S93-97.
Kulys et al., 1994. Carbon-paste biosensors array for long-term glucose measurement, Biosensors& Beioelectronics, 9:491-500.
Kunjan et al., Automated blood sampling and glocuse sensing in critical care settings, Journal of Diabetes Science and Technology 2(3):194-200, Mar. 2008.
Kunzler et al. 1993. Hydrogels based on hydrophilic side chain siloxanes. Poly Mat Sci and Eng 69:226-227.
Kunzler et al. Aug. 21, 1995. Contact lens materials. Chemistry & Industry. 651-655.
Kurtz et al. 2005. Recommendations for blood pressure measurement in humans and experimental animals, Part 2: Blood pressure measurement in experimental animals, a statement for professionals from the subcommittee of professional and public education of.
Lehmann et al. May 1994. Retrospective valication of a physiological model of glucose-iunsulin interaaction in tyhpe 1 diabetes mellitus, Med. Eng. Phys. 16:193-202.
Lerner et al. 1984. An implantable electrochemical glucose sensor. Ann. N. Y. Acad. Sci. 428:263-278.

(56) References Cited

OTHER PUBLICATIONS

Lewandowski et al. 1988. Evaluation of a miniature blood glucose sensor. Trans Am Soc Artif Intern Organs 34:255-258.
Leypoldt et al. 1984. Model of a two-substrate enzyme electrode for glucose. Anal. Chem. 56:2896-2904.
Linke et al. 1994. Amperometric biosensor for in vivo glucose sensing based on glucose oxidase immobilized in a redox hydrogel. Biosensors & Bioelectronics 9:151-158.
Lowe, 1984. Biosensors, Trends in Biotechnology, 2(3):59-65.
Lyandres et al. (2008). Progress toward an in vivo surface-enhanced raman spectroscopy glucose sensor. *Diabetes Technology & Therapeutics*, 10(4): 257-265.
Lyman D. 1960. Polyurethanes. I. The Solution Polymerization of Diisocyanates with Ethylene Glycol. J. Polymer Sci XLV:45:49.
Madaras et al. 1996. Microfabricated amperometric creatine and creatinine biosensors. Analytica Chimica Acta 319:335-345.
Malin et al. 1999. Noninvasive Prediction of Glucose by Near-Infrared Diffuse Reflectance Spectroscopy. Clinical Chemistry 45:9, 1651-1658.
Maran et al. 2002. Continuous subcutaneous glucose monitoring in diabetic patients: A multicenter analysis. Diabetes Care 25(2):347-352.
March, W. F. 2002. Dealing with the delay. Diabetes Technol Ther 4(1):49-50.
Marena et al. 1993. The artifical endocrine pancreas in clinical practice and research. Panminerva Medica 35(2):67-74.
Mascini et al. 1989. Glucose electrochemical probe with extended linearity for whole blood. *J Pharm Biomed Anal* 7(12): 1507-1512.
Mastrototaro, J. J. 2000. The MiniMed continuous glucose monitoring system. Diabetes Technol Ther 2(Suppl 1):S13-8.
Mastrototaro et al. 2003. Reproducibility of the continuous glucose monitoring system matches previous reports and the intended use of the product. Diabetes Care 26:256; author reply p. 257.
Matsumoto et al. 1998. A micro-planar amperometeric glucose sensor unsusceptible to interference species. Sensors and Actuators B 49:68-72.
Matsumoto et al. 2001. A long-term lifetime amperometric glucose sensor with a perfluorocarbon polymer coating. Biosens Bioelectron 16:271-276.
Matthews et al. 1988. An amperometric needle-type glucose sensor testing in rats and man. Diabetic Medicine 5:248-252.
Mazze et al. 2008. Characterizing glucose exposure for individuals with normal glucose tolerance using continuous glucose monitoring and ambulatory glucose profile analysis. Diab. Thechnol. & Therapeut., 10:149-159.
McCartney et al. 2001. Near-infrared fluorescence lifetime assay for serum glucose based on allophycocyanin-labeled concanavalin A. Anal Biochem 292:216-221.
McGrath et al. 1995. The use of differential measurements with a glucose biosensor for interference compensation during glucose determinations by flow injection analysis. Biosens Bioelectron 10:937-943.
Memoli et al. 2002. A comparison between different immobilised glucoseoxidase-based electrodes. J Pharm Biomed Anal 29:1045-1052.
Merriam-Webster Online Dictionary. Definition of "acceleration". http://www.merriam-webster.com/dictionary/Acceleration Jan. 11, 2010.
Merriam-Webster Online Dictionary. Definition of "system". http://www.merriam-webster.com/dictionary/System Jan. 11, 2010.
Merriam-Webster Online Dictionary. The term "nominal." http://www.m-w.com/dictionary/nominal.
Meyerhoff et al. 1992. On line continuous monitoring of subcutaneous tissue glucose in men by combining portable glucosensor with microdialysis. Diabetologia 35:1087-1092.
Moatti-Sirat et al. 1992. Evaluating in vitro and in vivo the interference of ascorbate and acetaminophen on glucose detection by a needle-type glucose sensor, Biosensors & Bioelectronics 7:345-352.

Mosbach et al. 1975. Determination of heat changes in the proximity of immobilized enzymes with an enzyme termistor and its use for the assay of metobolites, Biochim. Biophys. Acta. (Enzymology), 403:256-265.
Motonaka et al. 1993. Determination of cholesteral and cholesteral ester with novel enzyme microsensors, Anal. Chem. 65:3258-3261.
Moussy et al. 2000. Biomaterials community examines biosensor biocompatibility Diabetes Technol Ther 2:473-477.
Muslu. 1991. Trickling filter performance. Apllied Biochemistry and Biotechnology 37:211-224.
Myler et al. 2002. Ultra-thin-polysiloxane-film-composite membranes for the optimisation of amperometric oxidase enzyme electrodes. Biosens Bioelectron 17:35-43.
Nafion® 117 Solution Product Description, Product No. 70160, Sigma-Aldrich Corp., St. Louis, MO.
Nakayama et al. 1992. Surface fixation of hydrogels: heparin and glucose oxidase hydrogelated surfaces. ASAIO Journal M421-M424.
Ohara et al. 1994. "Wired" enzyme electrodes for amperometric determination of glucose or lactate in the presence of interfering substances. Anal Chem 66:2451-2457.
Oxford English Dictionary Online. Definition of "impending". http://www.askoxford.com/results/?view=dev dict&field-12668446 Impending&branch= Jan. 11, 2010.
Palmisano et al. 2000. Simultaneous monitoring of glucose and lactate by an interference and cross-talk free dual electrode amperometric biosensor based on electropolymerized thin films. Biosensors & Bioelectronics 15:531-539.
Park et al. 2002. Gas separation properties of polysiloxane/polyether mixed soft segment urethane urea membranes, *J. Membrane Science*, 204: 257-269.
Patel et al. 2003. Amperometric glucose sensors based on ferrocene containing polymeric electron transfer systems—a preliminary report. Biosens Bioelectron 18:1073-6.
Peacock et al. 2008. Cardiac troponin and outcome in acute heart failure. N. Engl. J. Med., 358:2117-2126.
Pegoraro et al. 1995. Gas transport properties of siloxane polyurethanes, Journal of Applied Polymer Science, 57:421-429.
Pfeiffer, E.F. 1990. The glucose sensor: the missing link in diabetes therapy, Horm Metab Res Suppl. 24:154-164.
Pfeiffer et al. 1992. On line continuous monitoring of subcutaneous tissue glucose is feasible by combining portable glucosensor with microdialysis. Horm. Metab. Res. 25:121-124.
Phillips and Smith. 1988. Bromedical Applications of Polyurethanes: Implications of Failure Mechanisms. J. Biomat. Appl. 3:202-227.
Pichert et al. 2000. Issues for the coming age of continuous glucose monitoring Diabetes Educ 26(6):969-980.
Pickup et al. 1988. Progress towards in vivo glucose sensing with a ferrocene-mediated amperometric enzyme electrode. 34-36.
Pickup et al. 1989. Potentially-implantable, amperometric glucose sensors with mediated electron transfer: improving the operating stability. Biosensors 4:109-119.
Pickup et al. 1993. Developing glucose sensors for in vivo use. Elsevier Science Publishers Ltd (UK), TIBTECH vol. 11: 285-291.
Pinner et al., Cross-linking of cellulose acetate by ionizing radiation, Nature, vol. 184, 1303-1304, Oct. 24, 1959.
Pitzer et al. 2001. Detection of hypoglycemia with the GlucoWatch biographer. Diabetes Care 24(5):881-885.
Poitout et al. 1993. A glucose monitoring system for on line estimation in man of blood glucose concentration using a miniaturized glucose sensor implanted in the subcutaneous tissue and a wearable control unit. Diabetologia 36:658-663.
Poitout et al. 1994. Development of a glucose sensor for glucose monitoring in man: the disposable implant concept. Clinical Materials 15:241-246.
Postlethwaite et al. 1996. Interdigitated array electrode as an alternative to the rotated ring-disk electrode for determination of the reaction products of dioxygen reduction. Analytical Chemistry 68:2951-2958.
Prabhu et al. 1981. Electrochemical studies of hydrogen peroxide at a platinum disc electrode, Electrochimica Acta 26(6):725-729.

(56) References Cited

OTHER PUBLICATIONS

Quinn et al. 1995. Kinetics of glucose delivery to subcutaneous tissue in rats measured with 0.3-mm amperometric microsensors. The American Physiological Society E155-E161.
Quinn et al. 1997. Biocompatible, glucose-permeable hydrogel for in situ coating of implantable biosensors. Biomaterials 18:1665-1670.
Rabah et al., 1991. Electrochemical wear of graphite anodes during electrolysis of brine, Carbon, 29(2):165-171.
Reach et al. 1986. A Method for Evaluating in vivo the Functional Characteristics of Glucose Sensors. Biosensors 2:211-220.
Reach, G. 2001. Which threshold to detect hypoglycemia? Value of receiver-operator curve analysis to find a compromise between sensitivity and specificity. Diabetes Care 24(5):803-804.
Reach, Gerard. 2001. Letters to the Editor Re: Diabetes Technology & Therapeutics, 2000;2:49-56. Diabetes Technology & Therapeutics 3(1):129-130.
Reusch. 2004. Chemical Reactivity. Organometallic Compounds. Virtual Textbook of Organic Chem. pp. 1-16, http://www.cem.msu.edu/~reusch/VirtualText/orgmetal.htm.
Rigla et al. 2008. Real-time continuous glucose monitoring together with telemedical assitance improves glycemic control and glucose stability in pump-treated patients. Diab. Thechnol. & Therapeut., 10:194-199.
Rivers et al., Central venous oxygen saturation monitoring in the critically ill patient, Current Opinion in Critical Care, 7:204-211, 2001.
Sachlos et al. 2003. Making Tissue Engineering Scaffolds Work. Review on the Application of Sold Freeform Fabrication Technology to the Production of Tissue Engineering Scaffolds. European Cells and Materials 5:29-40.
Salardi et al. 2002. The glucose area under the profiles obtained with continuous glucose monitoring system relationships with HbA1c in pediatric type 1 diabetic patients. Diabetes Care 25(10):1840-1844.
San Diego Plastics, Inc. 2009. Polyethylene Data Sheet, http://www.sdplastics.com/polyeth.html.
Sanders et al. 2003. Fibrous Encapsulation of Single Polymer Microfibers Depends on their Vertical Dimension in subcutaneous Tissue Polymer Microfibers pp. 1181-1187.
Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.
Sansen et al. 1990. A smart sensor for the voltammetric measurement of oxygen or glucose concentrations. Sensors and Actuators B 1:298-302.
Schmidtke et al., Measurement and modeling of the transient difference between blood and subcutaneous glucose concentrations in the rat after injection of insulin. *Proc Natl Acad Sci U S A* 1998, 95, 294-299.
Schoemaker et al. 2003. The SCGM1 system: Subcutaneous continuous glucose monitoring based on microdialysis technique. Diabetes Technology & Therapeutics 5(4):599-608.
Schoonen et al. 1990 Development of a potentially wearable glucose sensor for patients with diabetes mellitus: design and in-vitro evaluation. Biosensors & Bioelectronics 5:37-46.
Schuler et al. 1999. Modified gas-permeable silicone rubber membranes for covalent immobilisation of enzymes and their use in biosensor development. Analyst 124:1181-1184.
Selam, J. L. 1997. Management of diabetes with glucose sensors and implantable insulin pumps. From the dream of the 60s to the realities of the 90s. ASAIO J, 43:137-142.
Service et al. 1970. Mean amplitude of glycemic excursions, a measure of diabetic instability. Diabetes, 19: 644-655.
Service et al. 1987. Measurements of glucose control. Diabetes Care, 10: 225-237.
Service, R. F. 2002. Can sensors make a home in the body? Science 297:962-3.
Shichiri et al. 1982. Wearable artificial endocrine pancreas with needle-type glucose sensor. Lancet 2:1129-1131.
Skyler, J. S. 2000. The economic burden of diabetes and the benefits of improved glycemic control: The potential role of a continuous glucose monitoring system. Diabetes Technology & Therapeutics 2 Suppl 1:S7-12.
Slater-Maclean et al. 2008. Accuracy of glycemic measurements in the critically ill. Diab. Thechnol. & Therapeut., 10:169-177.
Sriyudthsak et al. 1996. Enzyme-epoxy membrane based glucose analyzing system and medical applications. Biosens Bioelectron 11:735-742.
Steil et al. 2003. Determination of plasma glucose during rapid glucose excursions with a subcutaneous glucose sensor. Diabetes Technology & Therapeutics 5(1):27-31.
Stern et al., 1957. Electrochemical polarization: 1. A theoretical analysis of the shape of polarization curves, Journal of the Electrochemical Society, 104(1):56-63.
Sternberg et al. 1988. Covalent enzyme coupling on cellulose acetate membranes for glucose sensor development. Anal. Chem. 69:2781-2786.
Stokes. 1988. Polyether Polyurethanes: Biostable or Not? J. Biomat. Appl. 3:228-259.
Suh et al. 2002. Behavior of fibroblasts on a porous hyaluronic acid incorporated collagen matrix. Yonsei Medical Journal 43(2):193-202.
Sumino T. et al. 1998. Preliminary study of continuous glucose monitoring with a microdialysis technique. Proceedings of the IEEE, 20(4):1775-1778.
Takegami et al. 1992. Pervaporation of ethanol water mixtures using novel hydrophobic membranes containing polydimethylsiloxane, Journal of Membrance Science, 75(93-105).
Tanenberg et al. 2000. Continuous glucose monitoring system: A new approach to the diagnosis of diabetic gastroparesis. Diabetes Technology & Therapeutics, 2 Suppl 1:S73-80.
Tatsuma et al. 1991. Oxidase/peroxidase bilayer-modified electrodes as sensors for lactate, pyruvate, cholesteral and uric acid, Analytica Chimica Acta, 242:85-89.
Thome-Duret et al. 1996. Use of a subcutaneous glucose sensor to detect decreases in glucose concentration prior to observation in blood, Anal. Chem. 68:3822-3826.
Thomé-Duret et al. 1998. Continuous glucose monitoring in the free-moving rat. Metabolism, 47:799-803.
Tierney et al. 2000. Effect of acetaminophen on the accuracy of glucose measurements obtained with the GlucoWatch biographer. Diabetes Technol Ther 2:199-207.
Tierney et al. 2000. The GlucoWatch® biographer: A frequent, automatic and noninvasive glucose monitor. Ann. Med. 32:632-641.
Torjman et al., Glucose monitoring in acute care: technologies on the horizon, Journal of Deabetes Science and Technology, 2(2):178-181, Mar. 2008.
Trecroci, D. 2002. A Glimpse into the Future—Continuous Monitoring of Glucose with a Microfiber. Diabetes Interview 42-43.
Tse and Gough. 1987. Time-Dependent Inactivation of Immobilized Glucose Oxidase and Catalase. Biotechnol. Bioeng. 29:705-713.
Turner et al. 1984. Carbon Monoxide: Acceptor Oxidoreductase from Pseudomonas Thermocarboxydovorans Strain C2 and its use in a Carbon Monoxide Sensor. Analytica Chimica Acta, 163: 161-174.
Turner, A.P.F. 1988. Amperometric biosensor based on mediator-modified electrodes. Methods in Enzymology 137:90-103.
Unger et al. 2004. Glucose control in the hospitalized patient. Emerg Med 36(9):12-18.
Updike et al. 1967. The enzyme electrode. Nature, 214:986-988.
Updike et al. 1988. Laboratory Evaluation of New Reusable Blood Glucose Sensor. Diabetes Care, 11:801-807.
Updike et al. 1994. Enzymatic glucose sensor: Improved long-term performance in vitro and in vivo. ASAIO Journal, 40(2):157-163.
Updike et al. 2000. A subcutaneous glucose sensor with improved longevity, dynamic range, and stability of calibration. Diabetes Care 23(2):208-214.
Utah Medical Products Inc., Blood Pressure Tranducers product specifications. 6 pp. 2003-2006, 2003.
Vadgama, P. Nov. 1981. Enzyme electrodes as practical biosensors. Journal of Medical Engineering & Technology 5(6):293-298.

(56) References Cited

OTHER PUBLICATIONS

Vadgama. 1988. Diffusion limited enzyme electrodes. NATO ASI Series: Series C, Math and Phys. Sci. 226:359-377.
Van den Berghe 2004. Tight blood glucose control with insulin in "real-life" intensive care. Mayo Clin Proc 79(8):977-978.
Velho et al. 1989. In vitro and in vivo stability of electrode potentials in needle-type glucose sensors. Influence of needle material. Diabetes 38:164-171.
Wang et al. 1994. Highly Selective Membrane-Free, Mediator-Free Glucose Biosensor. Anal. Chem. 66:3600-3603.
Wang et al. 1997. Improved ruggedness for membrane-based amperometric sensors using a pulsed amperometric method. Anal Chem 69:4482-4489.
Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.
Ward et al. 2002. A new amperometric glucose microsensor: In vitro and short-term in vivo evaluation. Biosensors & Bioelectronics, 17:181-189.
Wientjes, K. J. C. 2000. Development of a glucose sensor for diabetic patients (Ph.D. Thesis).
Wikipedia 2006. "Intravenous therapy," http://en.wikipedia.org/wiki/Intravenous_therapy, Aug. 15, 2006, 6 pp.
Wiley Electrical and Electronics Engineering Dictionary. 2004. John Wiley & Sons, Inc. pp. 141, 142, 548, 549.
Wilkins et al. 1988. The coated wire electrode glucose sensor, Horm Metab Res Suppl., 20:50-55.
Wilkins et al. 1995. Glucose monitoring: state of the art and future possibilities. Med Eng Phys 18:273-288.
Wilkins et al. 1995. Integrated implantable device for long-term glucose monitoring. Biosens. Bioelectron 10:485-494.
Wilson et al. 2000. Enzyme-based biosensors for in vivo measurements. Chem. Rev., 100:2693-2704.
Woodward. 1982. How Fibroblasts and Giant Cells Encapsulate Implants: Considerations in Design of Glucose Sensor. Diabetes Care 5:278-281.
Worsley et al., Measurement of glucose in blood with a phenylboronic acid optical sensor, Journal of Diabetes Science and Technology, 2(2):213-220, Mar. 2008.
Wright et al., Bioelectrochemical dehalogenations via direct electrochemistry of poly(ethylene oxide)-modified myoglobin, Electrochemistry Communications 1 (1999) 603-611.
Yamasaki, Yoshimitsu. Sep. 1984. The development of a needle-type glucose sensor for wearable artificial endocrine pancreas. Medical Journal of Osaka University 35(1-2):25-34.
Yamasaki et al. 1989. Direct measurement of whole blood glucose by a needle-type sensor. Clinica Chimica Acta. 93:93-98.
Yang et al. 1998. Development of needle-type glucose sensor with high selectivity. Science and Actuators B 46:249-256.
Ye et al. 1993. High Current Density 'Wired' Quinoprotein Glucose Dehydrogenase Electrode. Anal. Chem. 65:238-241.
Zamzow et al. 1990. Development and evaluation of a wearable blood glucose monitor, ASAIO Transactions; 36(3): pp. M588-M591.
Zethelius et al. 2008. Use of multiple biomarkers to improve the prediction of death from cardiovascular causes. N. Engl. J. Med., 358: 2107-2116.
Zhang et al. 1993. In vitro and in vivo evaluation of oxygen effects on a glucose oxidase based implantable glucose sensor. Analytica Chimica Acta, 281:513-520.
Zhu et al. 2002. Planar amperometric glucose sensor based on glucose oxidase immobilized by chitosan film on prussian blue layer. Sensors, 2:127-136.
Official Communication—EP Examination Report—in European App. No. 05771643.3, dated Aug. 19, 2009.
Office Action dated May 26, 2009 in U.S. Appl. No. 09/447,227.
Office Action dated Dec. 8, 2009 in U.S. Appl. No. 09/447,227.
Office Action dated Jan. 14, 2010 in U.S. Appl. No. 09/447,227.
Office Action dated Aug. 19, 2009 in U.S. Appl. No. 11/021,046.
Office Action dated Feb. 26, 2010 in U.S. Appl. No. 11/546,157.
Office Action dated Jun. 9, 2009 in U.S. Appl. No. 10/846,150.
Office Action dated Jan. 7, 2010 in U.S. Appl. No. 10/846,150.
Office Action dated Aug. 7, 2009 in U.S. Appl. No. 12/037,830.
Office Action dated Feb. 23, 2010 in U.S. Appl. No. 12/037,830.
Office Action dated Jul. 24, 2009 in U.S. Appl. No. 12/037,812.
Office Action dated Mar. 5, 2010 in U.S. Appl. No. 11/416,058.
Office Action dated Mar. 4, 2010 in U.S. Appl. No. 11/416,346.
Office Action dated Mar. 4, 2010 in U.S. Appl. No. 11/415,631.
Office Action dated Jul. 10, 2009 in U.S. Appl. No. 10/842,716.
Office Action dated Feb. 16, 2010 in U.S. Appl. No. 10/842,716.
Office Action dated Oct. 22, 2009 in U.S. Appl. No. 11/416,825.
Office Action dated Oct. 14, 2009 in U.S. Appl. No. 11/416,734.
Office Action dated May 17, 2010 in U.S. Appl. No. 11/416,734.
Office Action dated Jan. 13, 2010 in U.S. Appl. No. 12/139,305.
Office Action dated Mar. 3, 2010 in U.S. Appl. No. 12/111,062.
Office Action dated Nov. 12, 2009 in U.S. Appl. No. 11/077,883.
Office Action dated May 12, 2010 in U.S. Appl. No. 11/077,883.
Office Action dated Jan. 5, 2010 in U.S. Appl. No. 11/078,232.
Office Action dated Apr. 27, 2010 in U.S. Appl. No. 11/078,232.
Office Action dated Sep. 2, 2009 in U.S. Appl. No. 11/077,713.
Office Action dated Jan. 20, 2010 in U.S. Appl. No. 11/077,713.
Office Action dated Dec. 31, 2009 in U.S. Appl. No. 11/077,714.
Office Action dated Jan. 27, 2010 in U.S. Appl. No. 11/077,714.
Office Action dated Sep. 2, 2009 in U.S. Appl. No. 11/078,072.
Office Action dated Feb. 18, 2010 in U.S. Appl. No. 11/078,072.
Office Action dated Aug. 21, 2009 in U.S. Appl. No. 11/360,299.
Office Action dated May 12, 2010 in U.S. Appl. No. 11/360,299.
Office Action dated Dec. 31, 2009 in U.S. Appl. No. 11/503,367.
Office Action dated Feb. 3, 2010 in U.S. Appl. No. 11/503,367.
Office Action dated Jan. 21, 2010 in U.S. Appl. No. 11/157,365.
Office Action dated Oct. 29, 2009 in U.S. Appl. No. 11/360,819.
Office Action dated Apr. 7, 2010 in U.S. Appl. No. 11/360,819.
Office Action dated Apr. 12, 2010 in U.S. Appl. No. 11/333,837.
Office Action dated Feb. 23, 2010 in U.S. Appl. No. 12/113,508.
Office Action dated Nov. 20, 2009 in U.S. Appl. No. 11/360,250.
Office Action dated Mar. 5, 2010 in U.S. Appl. No. 11/360,250.
Ciba® Irgacure® 2959 Photoinitiator, Product Description. Apr. 2, 1998. Ciba Specialty Chemicals Inc., Basel, Switzerland. 3 pages. [corrected cite].
Direct 30/30® Blood Glucose Sensor, (Markwell Medical) Catalog, © 1990, ELCO Diagnostics Company. 1 page. [corrected cite].
Huang et al., Sep. 1997, A 0.5mW Passive Telemetry IC for Biomedical Applications, Proceedings of the 23rd European Solid-State Circuits Conference (ESSCIRC '97), pp. 172-175, Southampton, UK.
Huang et al. Aug. 1975. Electrochemical Generation of Oxygen. 1: The Effects of Anions and Cations on Hydrogen Chemisorption and Anodic Oxide Film Formation on Platinum Electrode. 2: The Effects of Anions and Cations on Oxygen Generation on Platinum Electrode. U.S. Department of Commerce/NTIS, pp. 1-116.
Hunter et al. Mar. 31, 2000. Minimally Invasive Glucose Sensor and Insulin Delivery System. MIT Home Automation and Healthcare Consortium. Progress Report No. 2-5. 17 pages.
Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications, 12:295-301.
Kurtz et al. 2005. Recommendations for blood pressure measurement in humans and experimental animals, Part 2: Blood pressure measurement in experimental animals, a statement for professionals from the subcommittee of professional and public education of the American Heart Association Council on High Blood Pressure Research. Hypertension 45:299-310.
Merriam-Webster Online Dictionary. Apr. 23, 2007. Definition of "nominal". http://www.merriam-webster.com/dictionary/nominal.
Nafion® 117 Solution Product Description, Product No. 70160, Sigma-Aldrich Corp., St. Louis, MO. Downloaded from https://www.signaaldrich.com/cgi-bin/hsrun/Suite7/Suite/HAHTpage/Suite.HsExternal Prod . . . on Apr. 7, 2005.
Bergveld et al., "Fabrication and Mass Production," Advances in Biosensors, Supplement 1 (1993) Chapter 6; 165-186.

(56) References Cited

OTHER PUBLICATIONS

Jablecki et al. 2000. Simulations of the frequency response of implantable glucose sensors. Analytical Chemistry 72:1853-1859.
Kovatchev et al. Aug. 2004. Evaluating the accuracy of continuous glucose-monitoring sensors: continuous glucose-error grid analysis illustrated by TheraSense Freestyle Navigator data. Diabetes Care 27(8):1922-1928.
Kusano, H. Glucose enzyme electrode with percutaneous interface which operates independently of dissolved oxygen. Clin Phys Physiol Meas. 1989. 10(1): 1-9.
Reach et al., "Clinical Needs for In Vivo Monitoring," Advances in Biosensors, Supplement 1 (1993) Chapter 1; 7-28.
Shichiri et al., "In Vivo Characteristics of Needle-Type Glucose Sensor—Measurements of Subcutaneous Glucose Concentrations in Human Volunteers," Implantable Glucose Sensors—The State of the Art, Hormone and Metabolic Research Supplement Series vol. No. 20 (1988) 17-20.
Office Action dated Jan. 20, 2012 for U.S. Appl. No. 12/359,207, filed Jan. 23, 2009.
European Office Action dated Dec. 15, 2011 in EP 10195496.4, filed Jul. 13, 2005.
European Response filed Jun. 22, 2012 in EP 10195496.4, filed Jul. 13, 2005.
European Extended Search Report dated Aug. 3, 2011 for Application No. EP 10195520.1, filed Jul. 13, 2005; 6 pages.
European Office Action dated Jul. 19, 2012 for Application No. EP 10195520.1, filed Jul. 13, 2005; 4 pages.
European Response/Claims to Office Action filed Jan. 16, 2013 for Application No. EP 10195520.1, filed Jul. 13, 2005; 7 pages.
Notice of Opposition dated Jul. 25, 2012 in European Patent No. 1986543, granted Dec. 14, 2011.
Japanese Office Action dated May 22, 2012 for Application No. 2011-121598, filed Jul. 13, 2005.
Request for Ex Parte Reexamination filed Apr. 29, 2011 for U.S. Appl. No. 11/077,693, filed Mar. 10, 2005 (now U.S. Pat. No. 7,713,574), 4 pgs.
Request for Ex Parte Reexamination dated Sep. 13, 2012 for U.S. Appl. No. 11/077,763, filed Mar. 10, 2005 (now U.S. Pat. No. 7,310,544), 3 pgs.
Request for Inter Partes Reexamination dated Sep. 14, 2012 for U.S. Pat. No. 7,713,574, dated Jun. 5, 2012; TOC. pp. 3.
European Office Action dated Sep. 18, 2013 and Applicant Response filed Mar. 22, 2013 for Application No. EP 11182622.8, filed Feb. 22, 2006; 9 pages.
Alberts et al. 1994. Molecular Biology of the Cell, $3^{rd}$ ed., p. G19.
Amato et al. 1989. J. Thorac Cardiovasc Surg 97(6):929-934. Experience with the Polytetrafluoroethylene surgical membrane for pericardial closure in operations for congenital cardiac defects.
Answers. Com, "xenogenic." The American Heritage Stedman's Medical Dictionary. Houghton Mifflin Company, 2002. Answers. com Nov. 7, 2006 http:--www.answers.com-topic-xenogenic.
Brauker et al. 1995. J. Biomed Mater Res 29:1517-1524. Neovascularization of synthetic membranes directed by membrane microarchitecture.
Copeland et al. 2001. J. Heart and Lung Tranpl 20(6):654-656. Synthetic Membrane Neo-Pericardium Facilitates Total Artificial Heart Explanation.

Dobson et al. 1990. Cell 61(2):223-230, 1-Butyrul-glycerol: A novel angiogenesis factor secreted by differentiating adipocytes.
English et al. 2001. Cardiovasc Res 49(3):588-599. Platelet-released phospholipids link haemostasis and angiogenesis.
Gore Preclude® Pericardial Membrane Brochure, Jun. 2009. W.L. Gore & Associates, Inc., Flagstaff, AZ 86004.
Gore Preclude® Pericardial Membrane Brochure Nov. 2001, W.L. Gore & Associates, Inc., Flaptaff, AZ 86004.
Halvorsen et al. 1993. J. Clin Invest 92(6):2872-2876. Vasodilation of rat retinal microvessels induced by monobutyrin.
Harada et al. 1988. J. Thorac Cardiovasc Surg 96(5):811-815. Long-term Results fo the Clinical use of an Expanded Polytetrafluoroethylene Surgical Membrane as a Pericardial Substitute.
Heydorn et al. 1987. J. Thorac Cardiovasc Surg 94(2):291-296. A New Look at Pericardial Substitutes.
Kidd et al. 2001. J Biomed Mater Research 59(2):366-377. Angiogenesis and neovascularization associated with extra cellular matrix modified porous implants.
Kugler et al. 1990. PACE 13:976-981. A new steroid-eluting epicardial lead: experience with atrial and ventricular implantation in the immature swine.
Ladd et al. 1996. Structure Determination by X-Ray Chrystal-lography, $3^{rd}$ Ed. Plenum, Chapter 1, pp. xx1-xxiv and 1-58.
LePrince et al. 2001. Eur. J. Cardiothoracic Surg 19:302-306. Expanded Polytetrafluoroethylene Membranes to Wrap Surfaces of Circulatory Support Devices in Patients Undergoing Bridge to Heart Transplantation.
Loebe et al. 1993. Texas Heart Institute Journal 20(3):213-217, Use of Polytetrafluoroethylene Surgical Membranes as a Pericardial Substitute, PTFE Membrane in Correction of Congenital Heart Defects.
Mathivanar et al. 1990. PACE 13()11):1883-1886. In vivo elution rate of drug eluting ceramic leads with a reduced dose of dexamethasone sodium phosphate.
Minale et al. 1988. J. Card Surg 3(3):193-201. Clinical Experience with Expanded Polytetrafluoroethylene Gore-Tex® Surgical Membrane for Pericardial Closer: A Study of 110 Cases.
Mond et al. 1992. PACE 15:95-107. The electrode-tissue interface: The revolutionary role of steroid elution.
Panetti 2002. Biochimca et Biophysica Acta 1582: 190-196. Differential effects of sphingosine 1-phosphate and lysophosphatidic acid on endothelial cells.
Radovsky et al. 1989. Am Heart JH. 117:1288-1297. Effects of dexamethasone elution on tissue reaction around stimulating electrodes of endocardial pacing leads in dogs.
Revuelta et al. 1985. J. Thorac Cardiovasc Surg 89(3):451-455. Expanded Polytetrafluoroethylene Surgical membrane for Pericardial Closure.
Sharkawy et al. 1997. J Biomed Mater Res 37:401-412. Engineering the tissue which encapsulates subcutaneous implants. I. Diffusion Properties.
Ward et al. 1999. ASAIO Journal 45:555-561. Assessment of chronically implanted subcutaneous glucose sensors in dogs: The effect of surrounding fluid masses.
Zhang et al. 1994. Analytical Chemistry 66(7):1183-1188. Elimination of the acetaminophen interference in an implantable glucose sensor.

\* cited by examiner

ANALYTE SENSOR

RELATED APPLICATIONS

This application is a continuation-in-part of U.S. application Ser. No. 11/077,715, filed Mar. 10, 2005 now U.S. Pat. No. 7,497,827, which claims the benefit of U.S. Provisional Application No. 60/587,787 filed Jul. 13, 2004; U.S. Provisional Application No. 60/587,800 filed Jul. 13, 2004; U.S. Provisional Application No. 60/614,683 filed Sep. 30, 2004; and U.S. Provisional Application No. 60/614,764 filed Sep. 30, 2004. This application also claims the benefit of U.S. Provisional Application No. 60/683,923 filed May 23, 2005. Each of the aforementioned applications is incorporated by reference herein in its entirety, and each is hereby expressly made a part of this specification.

FIELD OF THE INVENTION

The present invention relates generally to biointerface membranes utilized with implantable devices, such as devices for the detection of analyte concentrations in a biological sample. More particularly, the invention relates to novel biointerface membranes, to devices and implantable devices including these membranes, methods for forming the biointerface membranes on or around the implantable devices, and to methods for monitoring glucose levels in a biological fluid sample using an implantable analyte detection device.

BACKGROUND OF THE INVENTION

One of the most heavily investigated analyte sensing devices is the implantable glucose device for detecting glucose levels in hosts with diabetes. Despite the increasing number of individuals diagnosed with diabetes and recent advances in the field of implantable glucose monitoring devices, currently used devices are unable to provide data safely and reliably for certain periods of time. See Moatti-Sirat et al., *Diabetologia,* 35:224-30 (1992). There are two commonly used types of subcutaneously implantable glucose sensing devices. These types include those that are implanted transcutaneously and those that are wholly implanted.

SUMMARY OF THE INVENTION

Accordingly, in a first aspect, an analyte sensing device is provided adapted for short term insertion into a host's soft tissue, comprising a sensor having an architecture with at least one dimension less than about 1 mm, wherein the architecture is configured to create a fluid-filled pocket surrounding at least a portion of the sensor in vivo.

In an embodiment of the first aspect, the sensor is configured to measure a signal that is indicative of a concentration of the analyte within the fluid-filled pocket.

In an embodiment of the first aspect, the device further comprises electronics operatively coupled to the sensor and configured for detecting a signal from the sensor, wherein the signal is indicative of a concentration of an analyte within the host.

In an embodiment of the first aspect, the device further comprises a housing configured for placement adjacent to a host's skin, wherein at least a portion of the electronics are disposed in the housing.

In an embodiment of the first aspect, the sensor is a transcutaneous sensor.

In an embodiment of the first aspect, the device further comprises a spacer covering at least a portion of the sensor.

In an embodiment of the first aspect, the spacer covers a sensing mechanism of the sensor.

In an embodiment of the first aspect, the spacer comprises a biointerface.

In an embodiment of the first aspect, the spacer comprises a porous membrane configured to allow a body fluid to fill pores to thereby form a fluid-filled pocket.

In an embodiment of the first aspect, the device further comprises a bioactive agent incorporated into the sensor.

In an embodiment of the first aspect, the bioactive agent is selected from the group consisting of an anti-barrier cell agent, an anti-inflammatory agent, an anti-infective agent, a necrosing agent, an anesthetic, an inflammatory agent, a growth factor, an angiogenic factor, an adjuvant, an immunosuppressive agent, an antiplatelet agent, an anticoagulant, an ACE inhibitor, a cytotoxic agent, a vascularization compound, and an anti-sense molecule.

In a second aspect, an analyte sensor for measuring an analyte in a host is provided, the sensor comprising a sensor configured for transcutaneous insertion into a host's skin, wherein the sensor has an architecture with at least one dimension less than about 1 mm; and a biointerface covering at least a portion of the sensor.

In an embodiment of the second aspect, the biointerface is configured to allow fluid influx.

In an embodiment of the second aspect, the sensor is a transcutaneous sensor.

In an embodiment of the second aspect, the device further comprises electronics operatively coupled to the sensor and configured for detecting a signal from the sensor.

In an embodiment of the second aspect, the electronics are inductively coupled to the sensor.

In an embodiment of the second aspect, the device further comprises a housing configured for placement adjacent to the host's skin.

In an embodiment of the second aspect, the device further comprises a bioactive agent incorporated into the sensor.

In an embodiment of the second aspect, the bioactive agent is selected from the group consisting of an anti-barrier cell agent, an anti-inflammatory agent, an anti-infective agent, a necrosing agent, an anesthetic, an inflammatory agent, a growth factor, an angiogenic factor, an adjuvant, an immunosuppressive agent, an antiplatelet agent, an anticoagulant, an ACE inhibitor, a cytotoxic agent, a vascularization compound, and an anti-sense molecule.

In an embodiment of the second aspect, the biointerface is configured to provide a space for a body fluid to reside around the sensor in vivo.

In an embodiment of the second aspect, the biointerface is a porous membrane.

In an embodiment of the second aspect, the biointerface covers at least a sensing mechanism of the sensor.

In a third aspect, a method of detecting an analyte in a host is provided, comprising: a) inserting a sensor through a host's skin and into the host, wherein the sensor is a component of an analyte sensing device configured for transcutaneous insertion into the host, wherein the sensor has an architecture with at least one dimension less than about 1 mm, and wherein a biointerface covers at least a portion of the sensor, whereby fluid flows into the biointerface upon insertion of the sensor into the host; b) detecting from the sensor a signal indicative of a presence or a concentration of the analyte in the host; and c) removing the sensor from the host.

In an embodiment of the third aspect, the method further comprises repeating steps a) through c) after about 3 days or within about 3 days or less.

In an embodiment of the third aspect, the method further comprises repeating steps a) through c) after about 5 days or within about 5 days or less.

In an embodiment of the third aspect, the method further comprises repeating steps a) through c) after about 7 days or within about 7 days or less.

In an embodiment of the third aspect, the method further comprises repeating steps a) through c) after about 10 days or within about 10 days or less.

In an embodiment of the third aspect, the method further comprises coupling an electronics unit to the sensor.

In an embodiment of the third aspect, the sensor is a transcutaneous sensor.

In an embodiment of the third aspect, the method further comprises inductively coupling an electronics unit to the sensor.

In a fourth aspect, a wholly implantable sensing device is provided, the device comprising a sensor configured for implantation into a host and configured to detect an analyte in the host, wherein the sensor has an architecture with at least one dimension less than about 1 mm; a porous biointerface covering at least a portion of the sensor; and electronics operatively coupled to the sensor.

In an embodiment of the fourth aspect, the electronics are operatively connected to the sensor within a body of the sensor.

In an embodiment of the fourth aspect, the device further comprises a tether configured for operatively connecting the sensor to the electronics.

In an embodiment of the fourth aspect, the electronics are inductively coupled to the sensor.

In an embodiment of the fourth aspect, the device further comprises a mechanical spacer around the sensor or a protective framework around the sensor.

In an embodiment of the fourth aspect, the electronics are configured to detect a signal from the sensor and wherein the signal is indicative of at least one of a presence and a concentration of the analyte within the biointerface.

In an embodiment of the fourth aspect, the biointerface is an electrospun biointerface.

In an embodiment of the fourth aspect, the biointerface is formed directly on the sensor.

In an embodiment of the fourth aspect, the biointerface is preformed and subsequently applied to the sensor.

In an embodiment of the fourth aspect, the biointerface comprises a material selected from the group consisting of silicone, polytetrafluoroethylene, expanded polytetrafluoroethylene, polyethylene-co-tetrafluoroethylene, polyolefin, polyester, polycarbonate, biostable polytetrafluoroethylene, polyurethane homopolymer, polyurethane copolymer, polyurethane terpolymer, polypropylene, polyvinylchloride, polyvinylidene fluoride, polyvinyl alcohol, polybutylene terephthalate, polymethylmethacrylate, polyether ether ketone, polyamide, polyurethane, cellulosic polymer, poly(ethylene oxide), poly(propylene oxide), poly(propylene oxide) copolymer, polysulfone, polysulfone, block copolymers thereof, di-block copolymers thereof, tri-block copolymers thereof, alternating copolymers thereof, random copolymers thereof, graft copolymers thereof, mixtures thereof, and blends thereof.

In an embodiment of the fourth aspect, the biointerface is a fibrous biointerface.

In an embodiment of the fourth aspect, the biointerface comprises fibers less than about 6 microns in all but the longest dimension.

In an embodiment of the fourth aspect, passageways in the biointerface are configured to allow passage therein of invasive cells and to not allow extensive ingrowth of vascular tissue therein.

In an embodiment of the fourth aspect, the biointerface is an amorphous biointerface.

In an embodiment of the fourth aspect, a majority of pores of the biointerface are greater than about 0.6 microns in at least one dimension.

In an embodiment of the fourth aspect, the porous biointerface is configured to support tissue ingrowth.

In an embodiment of the fourth aspect, the biointerface is configured to resist barrier cell layer formation.

In an embodiment of the fourth aspect, the porous biointerface comprises interconnected pores.

In an embodiment of the fourth aspect, the biointerface further comprises a bioactive agent.

In an embodiment of the fourth aspect, the bioactive agent is selected from the group consisting of an anti-barrier cell agent, an anti-inflammatory agent, an anti-infective agent, a necrosing agent, an anesthetic, an inflammatory agent, a growth factor, an angiogenic factor, an adjuvant, an immunosuppressive agent, an antiplatelet agent, an anticoagulant, an ACE inhibitor, a cytotoxic agent, a vascularization compound, and an anti-sense molecule.

In an embodiment of the fourth aspect, the sensor comprises a working electrode embedded within the biointerface.

In an embodiment of the fourth aspect, the sensor further comprises at least one of a reference electrode embedded within the biointerface or deposited on a surface of the biointerface and a counter electrode embedded within the biointerface or deposited on a surface of the biointerface.

In a fifth aspect, a wholly implantable device for measuring an analyte in a host is provided, the device comprising a sensor configured for insertion into the host, wherein the sensor has an architecture with at least one dimension less than about 1 mm, a porous biointerface comprising a solid portion and a plurality of passageways extending from openings in an exterior surface of the biointerface into an interior portion of the biointerface, and electronics operatively coupled to the sensor.

In an embodiment of the fifth aspect, the passageways are interconnected.

In an embodiment of the fifth aspect, a cavity size of the passageways is greater than about 0.6 microns in at least one dimension.

In an embodiment of the fifth aspect, the biointerface is configured to resist barrier cell layer formation.

In an embodiment of the fifth aspect, the biointerface is configured to have a depth of greater than one passageway in three dimensions substantially throughout the entirety of a matrix comprising the biointerface.

In an embodiment of the fifth aspect, the solid portion comprises fibers.

In an embodiment of the fifth aspect, the solid portion comprises fibers less than about 6 microns in all but the longest dimension.

In an embodiment of the fifth aspect, the passageways are configured to allow passage of invasive cells therein and to not allow extensive ingrowth of vascular tissue therein.

In a sixth aspect, a method of detecting an analyte in a host is provided, comprising wholly implanting an analyte sensing device within a host, the device comprising a sensor for measuring the analyte in the host, wherein the sensor has an architecture with at least one dimension less than about 1 mm, a porous biointerface covering at least a portion of the sensor, and an electronics unit operatively coupled to the sensor; allowing tissue ingrowth within the biointerface; and detecting from the sensor a signal indicative of at least one of a presence and a concentration of the analyte in the host.

In an embodiment of the sixth aspect, the sensor is tethered to the electronics unit.

In an embodiment of the sixth aspect, the sensor is inductively coupled to the electronics unit.

In an embodiment of the sixth aspect, the signal is indicative of a presence of the analyte in the host or a concentration of analyte in the host.

In an embodiment of the sixth aspect, the biointerface is configured to prevent formation of a barrier-cell layer.

In an embodiment of the sixth aspect, the method further comprises removing the sensor from the host after at least about 1 month.

In a seventh aspect, a method for fabricating an analyte sensor configured for insertion into a host's soft tissue is provided, the method comprising forming a biointerface having a plurality of passageways and a solid portion on at least a sensing portion of a sensor, wherein the sensor is configured to measure an analyte in the host, and wherein the sensor has an architecture with at least one dimension less than about 1 mm.

In an embodiment of the seventh aspect, the step of forming a biointerface comprises a method selected from the group consisting of electrospinning, writing, lyophilizing, wrapping, weaving, and molding.

In an embodiment of the seventh aspect, the step of forming a biointerface comprises electrospinning the biointerface onto the sensor, writing the biointerface onto the sensor, lyophilizing the biointerface onto the sensor, wrapping the biointerface onto the sensor, weaving the biointerface onto the sensor, and molding the biointerface onto the sensor.

In an embodiment of the seventh aspect, the step of forming a biointerface comprises forming the biointerface directly on the sensor.

In an embodiment of the seventh aspect, the step of forming a biointerface comprises pre-forming the biointerface and then applying the preformed biointerface to the sensor.

In an embodiment of the seventh aspect, the step of forming a biointerface comprises pre-forming the biointerface and inserting the sensor into the preformed biointerface.

In an embodiment of the seventh aspect, the step of forming a biointerface comprises forming a selectively removable porogen on the sensor, wherein the porogen comprises particles formed onto the sensor and solidified to form a solidified mass of continuously interconnected particles; filling the porogen with a material; substantially solidifying the material; and removing the mass of continuously interconnected particles from contact with the sensor and solidified material to thereby form a solid portion that defines a plurality of passageways of the biointerface.

In an embodiment of the seventh aspect, the biointerface comprises a material selected from the group consisting of silicone, polytetrafluoroethylene, expanded polytetrafluoroethylene, polyethylene-co-tetrafluoroethylene, polyolefin, polyester, polycarbonate, biostable polytetrafluoroethylene, polyurethane homopolymer, polyurethane copolymer, polyurethane terpolymer, polypropylene, polyvinylchloride, polyvinylidene fluoride, polyvinyl alcohol, polybutylene terephthalate, polymethylmethacrylate, polyether ether ketone, polyamide, polyurethane, cellulosic polymer, poly(ethylene oxide), poly(propylene oxide), poly(propylene oxide) copolymer, polysulfone, polysulfone, block copolymers thereof, di-block copolymers thereof, tri-block copolymers thereof, alternating copolymers thereof, random copolymers thereof, graft copolymers thereof, mixtures thereof, and blends thereof.

In an embodiment of the seventh aspect, the step of forming a biointerface comprises forming an amorphous biointerface.

In an embodiment of the seventh aspect, the biointerface comprises pores of at least about 20 microns.

In an embodiment of the seventh aspect, the step of forming a biointerface comprises forming a fibrous biointerface.

In an embodiment of the seventh aspect, the biointerface comprises fibers less than about 6 microns in all but the longest dimension.

In an embodiment of the seventh aspect, the method further comprises a step of incorporating a bioactive agent into the biointerface.

In an embodiment of the seventh aspect, the bioactive agent is selected from the group consisting of an anti-barrier cell agent, an anti-inflammatory agent, an anti-infective agent, a necrosing agent, an anesthetic, an inflammatory agent, a growth factor, an angiogenic factor, an adjuvant, an immunosuppressive agent, an antiplatelet agent, an anticoagulant, an ACE inhibitor, a cytotoxic agent, a vascularization compound, and an anti-sense molecule.

In an embodiment of the seventh aspect, the step of forming a biointerface comprises writing a biointerface onto the sensor using a computer-aided machine.

In an eighth aspect, a method for fabricating an analyte sensor configured to be wholly implanted in a host's soft tissue is provided, the method comprising providing a sensor configured to measure an analyte in the host, wherein the sensor has an architecture with at least one dimension less than about 1 mm; and coating a biointerface onto the sensor, the biointerface comprising a plurality of cavities and a solid portion.

In an embodiment of the eighth aspect, the cavities are interconnected.

In an embodiment of the eighth aspect, the coating step comprises a method selected from the group consisting of electrospinning, writing, lyophilizing, wrapping, weaving, and molding.

In an embodiment of the eighth aspect, the method further comprises a step of curing the biointerface.

In an embodiment of the eighth aspect, the coating step comprises forming a selectively removable porogen onto the sensor, wherein the porogen comprises particles formed onto the sensor and solidified to form a solidified mass of continuously interconnected particles; filling the porogen with a material; substantially solidifying the material; and removing the mass of continuously interconnected particles from contact with the sensor and solidified material to thereby form a solid portion that defines a plurality of passageways of the biointerface.

In an embodiment of the eighth aspect, the biointerface comprises a material selected from the group consisting of silicone, polytetrafluoroethylene, expanded polytetrafluoroethylene, polyethylene-co-tetrafluoroethylene, polyolefin, polyester, polycarbonate, biostable polytetrafluoroethylene, polyurethane homopolymer, polyurethane copolymer, polyurethane terpolymer, polypropylene, polyvinylchloride, polyvinylidene fluoride, polyvinyl alcohol, polybutylene terephthalate, polymethylmethacrylate, polyether ether ketone, polyamide, polyurethane, cellulosic polymer, poly (ethylene oxide), poly(propylene oxide), poly(propylene oxide) copolymer, polysulfone, polysulfone, block copolymers thereof, di-block copolymers thereof, tri-block copolymers thereof, alternating copolymers thereof, random copolymers thereof, graft copolymers thereof, mixtures thereof, and blends thereof.

In an embodiment of the eighth aspect, the biointerface is an amorphous biointerface.

In an embodiment of the eighth aspect, the amorphous biointerface is molded onto the sensor.

In an embodiment of the eighth aspect, the coating step comprises forming a fibrous biointerface.

In an embodiment of the eighth aspect, the biointerface comprises fibers less than about 6 microns in all but the longest dimension.

In an embodiment of the eighth aspect, the method further comprises a step of incorporating a bioactive agent into the biointerface.

In an embodiment of the eighth aspect, the bioactive agent is selected from the group consisting of an anti-barrier cell agent, an anti-inflammatory agent, an anti-infective agent, a necrosing agent, an anesthetic, an inflammatory agent, a growth factor, an angiogenic factor, an adjuvant, a wound factor, an immunosuppressive agent, an antiplatelet agent, an anticoagulant, an ACE inhibitor, a cytotoxic agent, a vascularization compound, and an anti-sense molecule.

In an embodiment of the eighth aspect, the coating step comprises writing a biointerface onto the sensor using a computer-aided machine.

In an embodiment of the eighth aspect, the method further comprises a step of curing the biointerface.

In a ninth aspect, a method for making an analyte sensor configured for insertion into a host's soft tissue is provided, the method comprising providing a sensor configured to measure an analyte in a host, wherein the sensor has an architecture with at least one dimension less than about 1 mm; and directly writing a porous biointerface, wherein the porous biointerface is written based on a predefined pattern stored in a computer system.

In an embodiment of the ninth aspect, the method further comprises a step of curing the biointerface during direct writing step or after the direct writing step.

In an embodiment of the ninth aspect, the porous biointerface is directly written onto the sensor.

In an embodiment of the ninth aspect, the porous biointerface is directly written onto a substrate and then applied to the sensor.

DETAILED DESCRIPTION OF THE PREFERRED EMBODIMENT

Figure 1A:
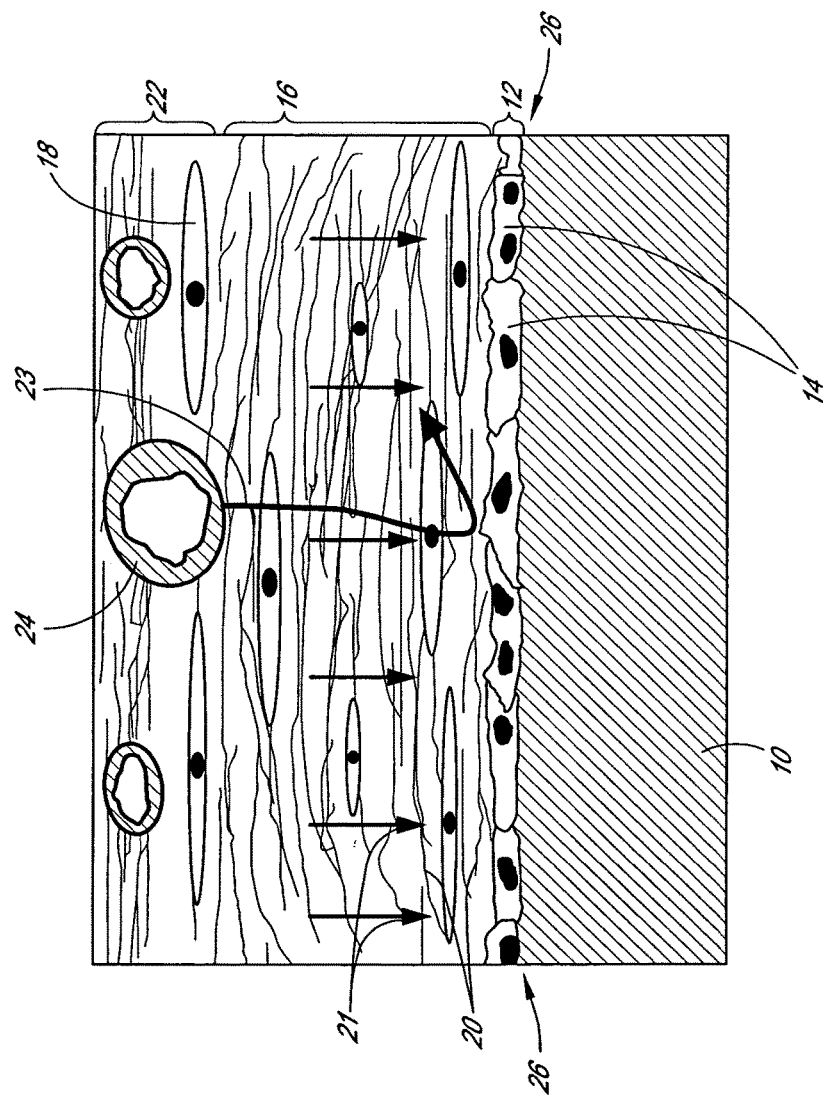
FIG. 1A is an illustration of classical three-layered foreign body response to a conventional synthetic membrane implanted under the skin.

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Definitions

In order to facilitate an understanding of the preferred embodiment, a number of terms are defined below.

The term "biointerface membrane" as used herein is a broad term, and is to be given its ordinary and customary meaning to a person of ordinary skill in the art (and is not to be limited to a special or customized meaning), and refers without limitation to a permeable membrane that functions as an interface between host tissue and an implantable device.

The term "barrier cell layer" as used herein is a broad term, and is to be given its ordinary and customary meaning to a person of ordinary skill in the art (and is not to be limited to a special or customized meaning), and refers without limitation to a part of a foreign body response that forms a cohesive monolayer of cells (for example, macrophages and foreign body giant cells) that substantially block the transport of molecules and other substances to the implantable device.

The term "cell processes" as used herein is a broad term, and is to be given its ordinary and customary meaning to a person of ordinary skill in the art (and is not to be limited to a special or customized meaning), and refers without limitation to pseudopodia of a cell.

The term "cellular attachment" as used herein is a broad term, and is to be given its ordinary and customary meaning to a person of ordinary skill in the art (and is not to be limited to a special or customized meaning), and refers without limitation to adhesion of cells and/or cell processes to a material at the molecular level, and/or attachment of cells and/or cell processes to microporous material surfaces or macroporous material surfaces. One example of a material used in the prior art that encourages cellular attachment to its porous surfaces is the BIOPORE™ cell culture support marketed by Millipore (Bedford, Mass.), and as described in Brauker et al., U.S. Pat. No. 5,741,330.

The term "solid portions" as used herein is a broad term, and is to be given its ordinary and customary meaning to a person of ordinary skill in the art (and is not to be limited to a special or customized meaning), and refers without limitation to portions of a membrane's material having a mechanical structure that demarcates cavities, voids, or other non-solid portions.

The term "co-continuous" as used herein is a broad term, and is to be given its ordinary and customary meaning to a person of ordinary skill in the art (and is not to be limited to a special or customized meaning), and refers without limitation to a solid portion or cavity wherein an unbroken curved line in three dimensions can be drawn between two sides of a membrane.

The term "biostable" as used herein is a broad term, and is to be given its ordinary and customary meaning to a person of ordinary skill in the art (and is not to be limited to a special or customized meaning), and refers without limitation to materials that are relatively resistant to degradation by processes that are encountered in vivo.

The terms "bioresorbable" or "bioabsorbable" as used herein are broad terms, and are to be given their ordinary and customary meaning to a person of ordinary skill in the art (and are not to be limited to a special or customized meaning), and refer without limitation to materials that can be absorbed, or lose substance, in a biological system.

The terms "nonbioresorbable" or "nonbioabsorbable" as used herein are broad terms, and are to be given their ordinary and customary meaning to a person of ordinary skill in the art (and are not to be limited to a special or customized meaning), and refer without limitation to materials that are not substantially absorbed, or do not substantially lose substance, in a biological system.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, *leptospira*, measles/mumps/rubella, *Mycobacterium leprae*, *Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), 5-hydroxyindoleacetic acid (FHIAA), and histamine.

The term "host" as used herein is a broad term, and is to be given its ordinary and customary meaning to a person of ordinary skill in the art (and is not to be limited to a special or customized meaning), and refers without limitation to mammals, preferably humans.

The phrase "continuous analyte sensing" as used herein is a broad term, and is to be given its ordinary and customary meaning to a person of ordinary skill in the art (and is not to be limited to a special or customized meaning), and refers without limitation to the period in which monitoring of analyte concentration is continuously, continually, and/or intermittently (but regularly) performed, for example, from about every 5 seconds or less to about 10 minutes or more, preferably from about 10, 15, 20, 25, 30, 35, 40, 45, 50, 55, or 60 second to about 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50 or 9.75 minutes.

The terms "analyte measuring device," "sensor," "sensing region," and "sensing mechanism" as used herein are broad terms, and are to be given their ordinary and customary meaning to a person of ordinary skill in the art (and are not to be limited to a special or customized meaning), and refer without limitation to the area of an analyte-monitoring device responsible for the detection of a particular analyte. For example, the sensing region can comprise a non-conductive body, a working electrode, a reference electrode, and a counter electrode (optional), forming an electrochemically reactive surface at one location on the body and an electronic connection at another location on the body, and a sensing membrane affixed to the body and covering the electrochemically reactive surface. During general operation of the device, a biological sample, for example, blood or interstitial fluid, or a component thereof contacts, either directly or after passage through one or more membranes, an enzyme, for example, glucose oxidase. The reaction of the biological sample or component thereof results in the formation of reaction products that permit a determination of the analyte level, for example, glucose, in the biological sample. In some embodiments, the sensing membrane further comprises an enzyme domain, for example, an enzyme layer, and an electrolyte phase, for example, a free-flowing liquid phase comprising an electrolyte-containing fluid described further below. The terms are broad enough to include the entire device, or only the sensing portion thereof (or something in between).

The term "electrochemically reactive surface" as used herein is a broad term, and is to be given its ordinary and customary meaning to a person of ordinary skill in the art (and is not to be limited to a special or customized meaning), and refers without limitation to the surface of an electrode where an electrochemical reaction takes place. In a working electrode, hydrogen peroxide produced by an enzyme-catalyzed reaction of an analyte being detected reacts can create a measurable electronic current. For example, in the detection of glucose, glucose oxidase produces $H_2O_2$ peroxide as a byproduct. The $H_2O_2$ reacts with the surface of the working electrode to produce two protons ($2H^+$), two electrons ($2e^-$) and one molecule of oxygen ($O_2$), which produces the electronic current being detected. In a counter electrode, a reducible species, for example, $O_2$ is reduced at the electrode surface so as to balance the current generated by the working electrode.

The term "sensing membrane" as used herein is a broad term, and is to be given its ordinary and customary meaning to a person of ordinary skill in the art (and is not to be limited to a special or customized meaning), and refers without limitation to a permeable or semi-permeable membrane that can comprise one or more domains and that is constructed of materials having a thickness of a few microns or more, and that are permeable to reactants and/or co-reactants employed in determining the analyte of interest. As an example, a sensing membrane can comprise an immobilized glucose oxidase enzyme, which catalyzes an electrochemical reaction with glucose and oxygen to permit measurement of a concentration of glucose.

The term "proximal" as used herein is a broad term, and is to be given its ordinary and customary meaning to a person of ordinary skill in the art (and is not to be limited to a special or customized meaning), and refers without limitation to a region near to a point of reference, such as an origin or a point of attachment.

The term "distal" as used herein is a broad term, and is to be given its ordinary and customary meaning to a person of ordinary skill in the art (and is not to be limited to a special or customized meaning), and refers without limitation to a region spaced relatively far from a point of reference, such as an origin or a point of attachment.

The terms "operably connected" and "operably linked" as used herein are broad terms, and are to be given their ordinary and customary meaning to a person of ordinary skill in the art (and are not to be limited to a special or customized meaning), and refer without limitation to one or more components linked to another component(s) in a manner that facilitates transmission of signals between the components. For example, one or more electrodes can be used to detect an analyte in a sample and convert that information into a signal; the signal can then be transmitted to an electronic circuit. In this example, the electrode is "operably linked" to the electronic circuit.

The term "adhere" and "attach" as used herein are broad terms, and are to be given their ordinary and customary meaning to a person of ordinary skill in the art (and are not be limited to a special or customized meaning), and refer without limitation to hold, bind, or stick, for example, by gluing, bonding, grasping, interpenetrating, or fusing.

The term "bioactive agent" as used herein is a broad term, and is to be given its ordinary and customary meaning to a person of ordinary skill in the art (and is not to be limited to a special or customized meaning), and refers without limitation to any substance that has an effect on or elicits a response from living tissue.

The term "bioerodible" or "biodegradable" as used herein are broad terms, and are to be given their ordinary and customary meaning to a person of ordinary skill in the art (and are not to be limited to a special or customized meaning), and refer without limitation to materials that are enzymatically degraded or chemically degraded in vivo into simpler components.

The terms "small diameter sensor," "small structured sensor," and "micro-sensor" as used herein are broad terms, and are to be given their ordinary and customary meaning to a person of ordinary skill in the art (and are not to be limited to a special or customized meaning), and refer without limitation to sensing mechanisms that are less than about 2 m in at least one dimension, and more preferably less than about 1 mm in at least one dimension. In some embodiments, the sensing mechanism (sensor) is less than about 0.95, 0.9, 0.85, 0.8, 0.75, 0.7, 0.65, 0.6, 0.5, 0.4, 0.3, 0.2, or 0.1 mm. In some embodiments, the sensing mechanism is a needle-type sensor, wherein the diameter is less than about 1 mm, see, for example, U.S. Pat. No. 6,613,379 to Ward et al. and co-pending U.S. patent application Ser. No. 11/077,715, filed on Mar. 10, 2005 and entitled, "TRANSCUTANEOUS ANALYTE SENSOR," both of which are incorporated herein by reference in their entirety. In some alternative embodiments, the sensing mechanism includes electrodes deposited on a planar substrate, wherein the thickness of the implantable portion is less than about 1 mm, see, for example U.S. Pat. No. 6,175,752 to Say et al. and U.S. Pat. No. 5,779,665 to Mastrototaro et. al., both of which are incorporated herein by reference in their entirety.

The term "electrospinning" as used herein is a broad term, and is to be given its ordinary and customary meaning to a person of ordinary skill in the art (and is not to be limited to a special or customized meaning), and refers without limitation to a process by which fibers are drawn out from a viscous polymer solution or melt by applying an electric field to a droplet of the solution (most often at a metallic needle tip). The electric field draws this droplet into a structure called a Taylor cone. If the viscosity and surface tension of the solution are appropriately tuned, varicose breakup (electrospray) is avoided and a stable jet is formed. A bending instability results in a whipping process which stretches and elongates this fiber until it has a diameter of micrometers (or nanometers).

The terms "interferants" and "interfering species" as used herein are broad terms, and are to be given their ordinary and customary meaning to a person of ordinary skill in the art (and are not to be limited to a special or customized meaning), and refer without limitation to effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured.

The term "drift" as used herein is a broad term, and is to be given its ordinary and customary meaning to a person of ordinary skill in the art (and is not to be limited to a special or customized meaning), and refers without limitation to a progressive increase or decrease in signal over time that is unrelated to changes in host systemic analyte concentrations, such as host postprandial glucose concentrations, for example. While not wishing to be bound by theory, it is believed that drift may be the result of a local decrease in glucose transport to the sensor, due to cellular invasion, which surrounds the sensor and forms a FBC, for example. It is also believed that an insufficient amount of interstitial fluid is surrounding the sensor, which results in reduced oxygen and/or glucose transport to the sensor, for example. An increase in local interstitial fluid may slow or reduce drift and thus improve sensor performance.

The term "sensing region" as used herein is a broad term, and is to be given its ordinary and customary meaning to a person of ordinary skill in the art (and is not to be limited to a special or customized meaning), and refers without limitation to the region of a monitoring device responsible for the detection of a particular analyte. The sensing region generally comprises a non-conductive body, a working electrode (anode), a reference electrode (optional), and/or a counter electrode (cathode) passing through and secured within the body forming electrochemically reactive surfaces on the body and an electronic connective means at another location on the body, and a multi-domain membrane affixed to the body and covering the electrochemically reactive surface.

The term "domain" as used herein is a broad term, and is to be given its ordinary and customary meaning to a person of ordinary skill in the art (and is not to be limited to a special or customized meaning), and refers without limitation to a region of the membrane system that can be a layer, a uniform or non-uniform gradient (for example, an anisotropic region of a membrane), or a portion of a membrane.

The term "membrane system" as used herein is a broad term, and is to be given its ordinary and customary meaning to a person of ordinary skill in the art (and is not to be limited to a special or customized meaning), and refers without limitation to a permeable or semi-permeable membrane that can be comprised of two or more domains and is typically constructed of materials of a few microns thickness or more, which is permeable to oxygen and is optionally permeable to, e.g., glucose or another analyte. In one example, the membrane system comprises an immobilized glucose oxidase enzyme, which enables a reaction to occur between glucose and oxygen whereby a concentration of glucose can be measured.

The terms "processor module" and "microprocessor" as used herein are broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer.

Overview

Devices and probes that are transcutaneously inserted or implanted into subcutaneous tissue conventionally elicit a foreign body response (FBR), which includes invasion of inflammatory cells that ultimately forms a foreign body capsule (FBC), as part of the body's response to the introduction of a foreign material. Specifically, insertion or implantation of a device, for example, a glucose sensing device, can result in an acute inflammatory reaction resolving to chronic inflammation with concurrent building of fibrotic tissue, such as described in detail above. Eventually, over a period of two to three weeks, a mature FBC, including primarily contractile fibrous tissue forms around the device. See Shanker and Greisler, Inflammation and Biomaterials in Greco RS, ed., "Implantation Biology: The Host Response and Biomedical Devices" pp 68-80, CRC Press (1994). The FBC surrounding conventional implanted devices has been shown to hinder or block the transport of analytes across the device-tissue interface. Thus, continuous extended life analyte transport (e.g., beyond the first few days) in vivo has been conventionally believed to be unreliable or impossible.

FIG. 1A is a schematic drawing that illustrates a classical FBR to a conventional cell-impermeable synthetic membrane 10 implanted under the skin. There are three main layers of a FBR. The innermost FBR layer 12, adjacent to the device, is composed generally of macrophages and foreign body giant cells 14 (herein referred to as the "barrier cell layer"). These cells form a monolayer of closely opposed cells over the entire surface of a microscopically smooth membrane, a macroscopically smooth (but microscopically rough) membrane, or a microporous (i.e., average pore size of less than about 1 μm) membrane. A membrane can be adhesive or non-adhesive to cells; however, its relatively smooth surface causes the downward tissue contracture 21 (discussed below) to translate directly to the cells at the device-tissue interface 26. The intermediate FBR layer 16 (herein referred to as the "fibrous zone"), lying distal to the first layer with respect to the device, is a wide zone (about 30 to 100 μm) composed primarily of fibroblasts 18, fibrous matrixes, and contractile fibrous tissue 20. The organization of the fibrous zone, and particularly the contractile fibrous tissue 20, contributes to the formation of the monolayer of closely opposed cells due to the contractile forces 21 around the surface of the foreign body (for example, membrane 10). The outermost FBR layer 22 is loose connective granular tissue containing new blood vessels 24 (herein referred to as the "vascular zone"). Over time, this FBR tissue becomes muscular in nature and contracts around the foreign body so that the foreign body remains tightly encapsulated. Accordingly, the downward forces 21 press against the tissue-device interface 26, and without any counteracting forces, aid in the formation of a barrier cell layer 14 that blocks and/or refracts the transport of analytes 23 (for example, glucose) across the tissue-device interface 26.

A consistent feature of the innermost layers 12, 16 is that they are devoid of blood vessels. This has led to widely supported speculation that poor transport of molecules across the device-tissue interface 26 is due to a lack of vascularization near the interface. See Scharp et al., World J. Surg., 8:221-229 (1984); and Colton et al., J. Biomech. Eng., 113:152-170 (1991). Previous efforts to overcome this problem have been aimed at increasing local vascularization at the device-tissue interface, but have achieved only limited success.

Although local vascularization can aid in sustenance of local tissue over time, the presence of a barrier cell layer 14 prevents the passage of molecules that cannot diffuse through the layer. For example, when applied to an implantable glucose-measuring device, it is unlikely that glucose would enter the cell via glucose transporters on one side of the cell and exit on the other side. Instead, it is likely that any glucose that enters the cell is phosporylated and remains within the cell. The only cells known to facilitate transport of glucose from one side of the cell to another are endothelial cells. Consequently, little glucose reaches the implant's membrane through the barrier cell layer. The known art purports to increase the local vascularization in order to increase solute availability. See Brauker et al., U.S. Pat. No. 5,741,330. However, it has been observed by the inventors that once the monolayer of cells (barrier cell layer) is established adjacent to a membrane, increasing angiogenesis is not sufficient to increase transport of molecules such as glucose and oxygen across the device-tissue interface 26. In fact, the barrier cell layer blocks and/or refracts the analytes 23 from transport across the device-tissue interface 26.

Referring now to short-term sensors, or the short-term function of long-term sensors, it is believed that certain aspects of the FBR in the first few days may play a role in noise. It has been observed that some sensors function more poorly during the first few hours after insertion than they do later. This is exemplified by noise and/or a suppression of the signal during the first few hours (e.g., about 2 to about 24 hours) after insertion. These anomalies often resolve spontaneously after which the sensors become less noisy, have improved sensitivity, and are more accurate than during the early period. It has been observed that some transcutaneous sensors and wholly implantable sensors are subject to noise for a period of time after application to the host (i.e., inserted transcutaneously or wholly implanted below the skin). "Noise," as used herein, is a broad term and is used in its ordinary sense, including, without limitation, a signal detected by the sensor that is unrelated to analyte concentration and can result in reduced sensor performance. One type of noise has been observed during the few hours (e.g., about 2 to about 24 hours) after sensor insertion. After the first 24 hours, the noise often disappears, but in some hosts, the noise may last for about three to four days When a sensor is first inserted or implanted into the subcutaneous tissue, it comes into contact with a wide variety of possible tissue conformations. Subcutaneous tissue in different hosts may be relatively fat free in cases of very athletic people, or may be mostly composed of fat in the majority of people. Fat comes in a wide array of textures from very white, puffy fat to very dense, fibrous fat. Some fat is very yellow and dense looking; some is very clear, puffy, and white looking, while in other cases it is more red or brown. The fat may be several inches thick or only 1 cm thick. It may be very vascular or relatively nonvascular. Many hosts with diabetes have some subcutaneous scar tissue due to years of insulin pump use or insulin injection. At times, during insertion, sensors may come to rest in such a scarred area. The subcutaneous tissue may even vary greatly from one location to another in the abdomen of a given host. Moreover, by chance, the sensor may come to rest near a more densely vascularized area or in a less vascularized area of a given host. While not wishing to be bound by theory, it is believed that creating a space between the sensor surface and the surrounding cells, including formation of a fluid pocket surrounding the sensor, may enhance sensor performance.

Figure 1B:
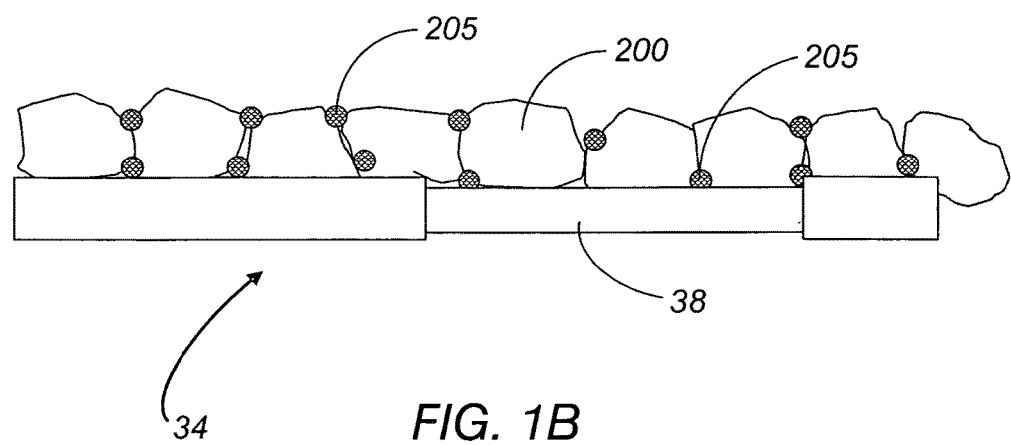
FIG. 1B is a side schematic view of adipose cell contact with an inserted transcutaneous sensor or an implanted sensor.

FIG. 1B is a side schematic view of adipose cell contact with an inserted transcutaneous sensor or an implanted sensor. In this case, the sensor is firmly inserted into a small space with adipose cells pressing up against the surface. Close association of the adipose cells with the sensor can also occur, for example wherein the surface of the sensor is hydrophobic. For example, the adipose cells 200 may physically block the surface of the sensor.

Typically adipose cells can be about 120 microns in diameter and are typically fed by tiny capillaries 205. When the sensor is pressed against the fat tissue, very few capillaries may actually come near the surface of the sensor. This may be analogous to covering the surface of the sensor with an impermeable material such as cellophane, for example. Even if there were a few small holes in the cellophane, the sensor's function would likely be compromised. Additionally, the surrounding tissue has a low metabolic rate and therefore does not require high amounts of glucose and oxygen. While not wishing to be bound by theory, it is believed that, during this early period, the sensor's signal can be noisy and the signal can be suppressed due to close association of the sensor surface with the adipose cells and decreased availability of oxygen and glucose both for physical-mechanical reasons and physiological reasons.

Referring now to long-term function of a sensor, after a few days to two or more weeks of implantation, these devices typically lose their function. In some applications, cellular attack or migration of cells to the sensor can cause reduced sensitivity and/or function of the device, particularly after the first day of implantation. See also, for example, U.S. Pat. No. 5,791,344 and Gross et al. and "Performance Evaluation of the MiniMed Continuous Monitoring System During Host home Use," Diabetes Technology and Therapeutics, (2000) 2(1):49-56, which have reported a glucose oxidase-based device, approved for use in humans by the Food and Drug Administration, that functions well for several days following implantation but loses function quickly after the several days (e.g., a few days up to about 14 days).

It is believed that this lack of device function is most likely due to cells, such as polymorphonuclear cells and monocytes that migrate to the sensor site during the first few days after implantation. These cells consume local glucose and oxygen. If there is an overabundance of such cells, they can deplete glucose and/or oxygen before it is able to reach the device enzyme layer, thereby reducing the sensitivity of the device or rendering it non-functional. Further inhibition of device function can be due to inflammatory cells, for example, macrophages, that associate, for example, align at the interface, with the implantable device, and physically block the transport of glucose into the device, for example, by formation of a barrier cell layer. Additionally, these inflammatory cells can biodegrade many artificial biomaterials (some of which were, until recently, considered non-biodegradable). When activated by a foreign body, tissue macrophages degranulate, releasing hypochlorite (bleach) and other oxidative species. Hypochlorite and other oxidative species are known to break down a variety of polymers.

Analyte sensors for in vivo use over various lengths of time have been developed. For example, sensors to be used for a short period of time, such as about 1 to about 14 days, have been produced. Herein, this sensor will be referred to as a short-term sensor (STS). STS may be a transcutaneous device, in that a portion of the device may be inserted through the host's skin and into the underlying soft tissue while a portion of the device remains on the surface of the host's skin. In one aspect, in order to overcome the problems associated with noise or other sensor function in the short-term (e.g., short term sensors or short term function of long term sensors), preferred embodiments employ materials that promote formation of a fluid pocket around the sensor, for example architectures such as porous biointerface membrane or matrices that create a space between the sensor and the surrounding tissue.

In some embodiments, a short-term sensor is provided with a spacer adapted to provide a fluid pocket between the sensor and the host's tissue. It is believed that this spacer, for example a biointerface material, matrix, structure, and the like as described in more detail elsewhere herein, provides for oxygen and/or glucose transport to the sensor.

Figure 1C:
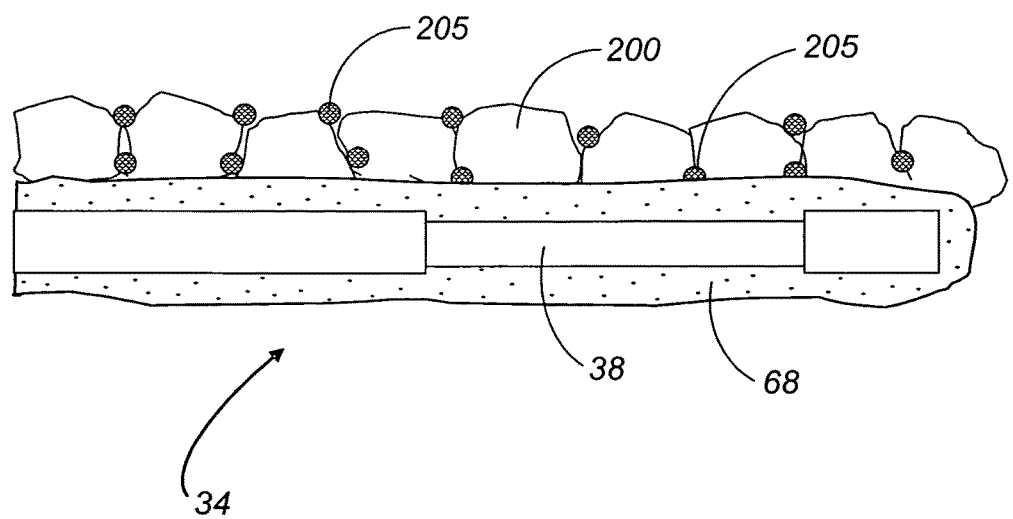
FIG. 1C is a side schematic view of a biointerface membrane preventing adipose cell contact with an inserted transcutaneous sensor or an implanted sensor.

FIG. 1C is a side schematic view of a biointerface membrane as the spacer preventing adipose cell contact with an inserted transcutaneous sensor or an implanted sensor in one exemplary embodiment. In this illustration, a porous biointerface membrane 34 surrounds the sensor 58, covering the sensing mechanism 34 and is configured to fill with fluid in vivo, thereby creating a fluid pocket surrounding the sensor. Accordingly, the adipose cells surrounding the sensor are held a distance away (such as the thickness of the porous biointerface membrane, for example) from the sensor surface. Accordingly, as the porous biointerface membrane fills with fluid (i.e., creates fluid pocket), oxygen and glucose are transported to the sensing mechanism in quantities sufficient to maintain accurate sensor function.

Accordingly, a short term sensor (or short term function of a long term sensor) including a biointerface, including but not limited to, for example, porous biointerface materials, mesh cages, and the like, all of which are described in more detail elsewhere herein, can be employed to improve sensor function in the short term (e.g., first few hours to days). It is noted that porous biointerface membranes need not necessarily include interconnected cavities for creating a fluid pocket in the short-term.

In some circumstances, for example in long-term sensors, it is believed that that foreign body response is the dominant event surrounding extended implantation of an implanted device, and can be managed or manipulated to support rather than hinder or block analyte transport. In another aspect, in order to extend the lifetime of the sensor, preferred embodiments employ materials that promote vascularized tissue ingrowth, for example within a porous biointerface membrane. For example tissue in-growth into a porous biointerface material surrounding a long-term sensor may promote sensor function over extended periods of time (e.g., weeks, months, or years). It has been observed that in-growth and formation of a tissue bed can take up to 3 weeks. Tissue ingrowth and tissue bed formation is believed to be part of the foreign body response. As will be discussed herein, the foreign body response can by manipulated by the use of porous biointerface materials that surround the sensor and promote ingrowth of tissue and microvasculature over time. Long term use sensors (LTS), for use over a period of weeks, months or even years, have also been produced. LTS may be wholly implantable, and placed within the host's soft tissue below the skin, for example.

Accordingly, a long term sensor including a biointerface, including but not limited to, for example, porous biointerface materials including a solid portion and interconnected cavities, all of which are described in more detail elsewhere herein, can be employed to improve sensor function in the long term (e.g., after tissue ingrowth).

Sensing Mechanism

In general, the analyte sensors of the preferred embodiments include a sensing mechanism 34 with a small structure (e.g., small structured-, micro- or small diameter sensor), for example, a needle-type sensor, in at least a portion thereof. As used herein a "small structure" preferably refers to an architecture with at least one dimension less than about 1 mm. The small structured sensing mechanism can be wire-based, substrate based, or any other architecture. In some alternative embodiments, the term "small structure" can also refer to slightly larger structures, such as those having their smallest dimension being greater than about 1 mm, however, the architecture (e.g., mass or size) is designed to minimize the foreign body response due to size and/or mass. In the preferred embodiments, a biointerface membrane is formed onto the sensing mechanism 34 as described in more detail below.

Figure 2A:
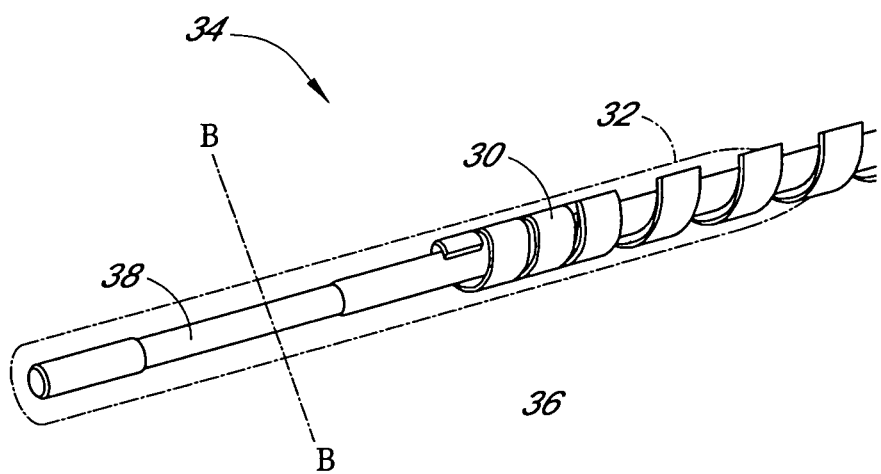
FIG. 2A is an expanded view of an exemplary embodiment of a continuous analyte sensor.

FIG. 2A is an expanded view of an exemplary embodiment of a continuous analyte sensor 34, also referred to as a transcutaneous analyte sensor, or needle-type sensor, particularly illustrating the sensing mechanism 36. Preferably, the sensing mechanism comprises a small structure as defined herein and is adapted for insertion under the host's skin, and the remaining body of the sensor (e.g., electronics, etc.) can reside ex vivo. In the illustrated embodiment, the analyte sensor 34, includes two electrodes, i.e., a working electrode 38 and at least one additional electrode 30, which may function as a counter and/or reference electrode, hereinafter referred to as the reference electrode 30.

In some exemplary embodiments, each electrode is formed from a fine wire with a diameter of from about 0.001 or less to about 0.010 inches or more, for example, and is formed from, e.g., a plated insulator, a plated wire, or bulk electrically conductive material. Although the illustrated electrode configuration and associated text describe one preferred method of forming a transcutaneous sensor, a variety of known transcutaneous sensor configurations can be employed with the transcutaneous analyte sensor system of the preferred embodiments, such as are described in U.S. Pat. No. 6,695,860 to Ward et al., U.S. Pat. No. 6,565,509 to Say et al., U.S. Pat. No. 6,248,067 to Causey III et al., and U.S. Pat. No. 6,514,718 to Heller et al.

In preferred embodiments, the working electrode comprises a wire formed from a conductive material, such as platinum, platinum-iridium, palladium, graphite, gold, carbon, conductive polymer, alloys, or the like. Although the electrodes can be formed by a variety of manufacturing techniques (bulk metal processing, deposition of metal onto a substrate, or the like), it can be advantageous to form the electrodes from plated wire (e.g., platinum on steel wire) or bulk metal (e.g., platinum wire). It is believed that electrodes formed from bulk metal wire provide superior performance (e.g., in contrast to deposited electrodes), including increased stability of assay, simplified manufacturability, resistance to contamination (e.g., which can be introduced in deposition processes), and improved surface reaction (e.g., due to purity of material) without peeling or delamination.

The working electrode 38 is configured to measure the concentration of an analyte. In an enzymatic electrochemical sensor for detecting glucose, for example, the working electrode measures the hydrogen peroxide produced by an enzyme catalyzed reaction of the analyte being detected and creates a measurable electronic current. For example, in the detection of glucose wherein glucose oxidase produces hydrogen peroxide as a byproduct, hydrogen peroxide reacts with the surface of the working electrode producing two protons ($2H^+$), two electrons ($2e^-$) and one molecule of oxygen ($O_2$), which produces the electronic current being detected.

The working electrode 38 is covered with an insulating material, for example, a non-conductive polymer. Dip-coating, spray-coating, vapor-deposition, or other coating or deposition techniques can be used to deposit the insulating material on the working electrode. In one embodiment, the insulating material comprises parylene, which can be an advantageous polymer coating for its strength, lubricity, and electrical insulation properties. Generally, parylene is produced by vapor deposition and polymerization of para-xylylene (or its substituted derivatives). However, any suitable insulating material can be used, for example, fluorinated polymers, polyethyleneterephthalate, polyurethane, polyimide, other nonconducting polymers, or the like. Glass or ceramic materials can also be employed. Other materials suitable for use include surface energy modified coating systems such as are marketed under the trade names AMC18, AMC148, AMC141, and AMC321 by Advanced Materials Components Express of Bellafonte, Pa. In some alternative embodiments, however, the working electrode may not require a coating of insulator.

Preferably, the reference electrode 30, which may function as a reference electrode alone, or as a dual reference and counter electrode, is formed from silver, silver/silver chloride, or the like. Preferably, the electrodes are juxtapositioned and/or twisted with or around each other; however other configurations are also possible. In one example, the reference electrode 30 is helically wound around the working electrode 38 as illustrated in FIG. 1B. The assembly of wires may then be optionally coated together with an insulating material, similar to that described above, in order to provide an insulating attachment (e.g., securing together of the working and reference electrodes).

In embodiments wherein an outer insulator is disposed, a portion of the coated assembly structure can be stripped or otherwise removed, for example, by hand, excimer lasing, chemical etching, laser ablation, grit-blasting (e.g., with sodium bicarbonate or other suitable grit), or the like, to expose the electroactive surfaces. Alternatively, a portion of the electrode can be masked prior to depositing the insulator in order to maintain an exposed electroactive surface area. In one exemplary embodiment, grit blasting is implemented to expose the electroactive surfaces, preferably utilizing a grit material that is sufficiently hard to ablate the polymer material, while being sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some preferred embodiments, sodium bicarbonate is an advantageous grit-material because it is sufficiently hard to ablate, e.g., a parylene coating without damaging, e.g., an underlying platinum conductor. One additional advantage of sodium bicarbonate blasting includes its polishing action on the metal as it strips the polymer layer, thereby eliminating a cleaning step that might otherwise be necessary.

In some embodiments, a radial window is formed through the insulating material to expose a circumferential electroactive surface of the working electrode. Additionally, sections of electroactive surface of the reference electrode are exposed. For example, the sections of electroactive surface can be masked during deposition of an outer insulating layer or etched after deposition of an outer insulating layer. In some applications, cellular attack or migration of cells to the sensor can cause reduced sensitivity and/or function of the device, particularly after the first day of implantation. However, when the exposed electroactive surface is distributed circumferentially about the sensor (e.g., as in a radial window), the available surface area for reaction can be sufficiently distributed so as to minimize the effect of local cellular invasion of the sensor on the sensor signal. Alternatively, a tangential exposed electroactive window can be formed, for example, by stripping only one side of the coated assembly structure. In other alternative embodiments, the window can be provided at the tip of the coated assembly structure such that the electroactive surfaces are exposed at the tip of the sensor. Other methods and configurations for exposing electroactive surfaces can also be employed.

Preferably, the above-exemplified sensor has an overall diameter of not more than about 0.020 inches (about 0.51 mm), more preferably not more than about 0.018 inches (about 0.46 mm), and most preferably not more than about 0.016 inches (0.41 mm). In some embodiments, the working electrode has a diameter of from about 0.001 inches or less to about 0.010 inches or more, preferably from about 0.002 inches to about 0.008 inches, and more preferably from about 0.004 inches to about 0.005 inches. The length of the window can be from about 0.1 mm (about 0.004 inches) or less to about 2 mm (about 0.078 inches) or more, and preferably from about 0.5 mm (about 0.02 inches) to about 0.75 mm (0.03 inches). In such embodiments, the exposed surface area of the working electrode is preferably from about 0.000013 in$^2$ (0.0000839 cm$^2$) or less to about 0.0025 in$^2$ (0.016129 cm$^2$) or more (assuming a diameter of from about 0.001 inches to about 0.010 inches and a length of from about 0.004 inches to about 0.078 inches). The preferred exposed surface area of the working electrode is selected to produce an analyte signal with a current in the picoAmp range, such as is described in more detail elsewhere herein. However, a current in the picoAmp range can be dependent upon a variety of factors, for example the electronic circuitry design (e.g., sample rate, current draw, A/D converter bit resolution, etc.), the membrane system (e.g., permeability of the analyte through the membrane system), and the exposed surface area of the working electrode. Accordingly, the exposed electroactive working electrode surface area can be selected to have a value greater than or less than the above-described ranges taking into consideration alterations in the membrane system and/or electronic circuitry. In preferred embodiments of a glucose sensor, it can be advantageous to minimize the surface area of the working electrode while maximizing the diffusivity of glucose in order to optimize the signal-to-noise ratio while maintaining sensor performance in both high and low glucose concentration ranges.

In some alternative embodiments, the exposed surface area of the working (and/or other) electrode can be increased by altering the cross-section of the electrode itself. For example, in some embodiments the cross-section of the working electrode can be defined by a cross, star, cloverleaf, ribbed, dimpled, ridged, irregular, or other non-circular configuration; thus, for any predetermined length of electrode, a specific increased surface area can be achieved (as compared to the area achieved by a circular cross-section). Increasing the surface area of the working electrode can be advantageous in providing an increased signal responsive to the analyte concentration, which in turn can be helpful in improving the signal-to-noise ratio, for example.

In some alternative embodiments, additional electrodes can be included within the assembly, for example, a three-electrode system (working, reference, and counter electrodes) and/or an additional working electrode (e.g., an electrode which can be used to generate oxygen, which is configured as a baseline subtracting electrode, or which is configured for measuring additional analytes). Co-pending U.S. patent application Ser. No. 11/007,635, filed Dec. 7, 2004 and entitled "SYSTEMS AND METHODS FOR IMPROVING ELECTROCHEMICAL ANALYTE SENSORS" and U.S. patent application Ser. No. 11/004,561, filed Dec. 3, 2004 and entitled "CALIBRATION TECHNIQUES FOR A CONTINUOUS ANALYTE SENSOR" describe some systems and methods for implementing and using additional working, counter, and/or reference electrodes. In one implementation wherein the sensor comprises two working electrodes, the two working electrodes are juxtapositioned (e.g., extend parallel to each other), around which the reference electrode is disposed (e.g., helically wound). In some embodiments wherein two or more working electrodes are provided, the working electrodes can be formed in a double-, triple-, quad-, etc. helix configuration along the length of the sensor (for example, surrounding a reference electrode, insulated rod, or other support structure). The resulting electrode system can be configured with an appropriate membrane system, wherein the first working electrode is configured to measure a first signal comprising glucose and baseline and the additional working electrode is configured to measure a baseline signal consisting of baseline only (e.g., configured to be substantially similar to the first working electrode without an enzyme disposed thereon). In this way, the baseline signal can be subtracted from the first signal to produce a glucose-only signal that is substantially not subject to fluctuations in the baseline and/or interfering species on the signal. Accordingly, the above-described dimensions can be altered as desired. Although the preferred embodiments illustrate one electrode configuration including one bulk metal wire helically wound around another bulk metal wire, other electrode configurations are also contemplated. In an alternative embodiment, the working electrode comprises a tube with a reference electrode disposed or coiled inside, including an insulator there between. Alternatively, the reference electrode comprises a tube with a working electrode disposed or coiled inside, including an insulator there between. In another alternative embodiment, a polymer (e.g., insulating) rod is provided, wherein the electrodes are deposited (e.g., electroplated) thereon. In yet another alternative embodiment, a metallic (e.g., steel) rod is provided, coated with an insulating material, onto which the working and reference electrodes are deposited. In yet another alternative embodiment, one or more working electrodes are helically wound around a reference electrode.

While the methods of preferred embodiments are especially well suited for use with small structured-, micro- or small diameter sensors, the methods can also be suitable for use with larger diameter sensors, e.g., sensors of 1 mm to about 2 mm or more in diameter.

In some alternative embodiments, the sensing mechanism includes electrodes deposited on a planar substrate, wherein the thickness of the implantable portion is less than about 1 mm, see, for example U.S. Pat. No. 6,175,752 to Say et al. and U.S. Pat. No. 5,779,665 to Mastrototaro et al., both of which are incorporated herein by reference in their entirety.

Sensing Membrane

Preferably, a sensing membrane 32 is disposed over the electroactive surfaces of the sensor 34 and includes one or more domains or layers. In general, the sensing membrane functions to control the flux of a biological fluid there through and/or to protect sensitive regions of the sensor from contamination by the biological fluid, for example. Some conventional electrochemical enzyme-based analyte sensors generally include a sensing membrane that controls the flux of the analyte being measured, protects the electrodes from contamination of the biological fluid, and/or provides an enzyme that catalyzes the reaction of the analyte with a co-factor, for example. See, e.g., co-pending U.S. patent application Ser. No. 10/838,912, filed May 3, 2004 entitled "IMPLANTABLE ANALYTE SENSOR" and U.S. patent application Ser. No. 11/077,715, filed Mar. 10, 2005 and entitled "TRANSCUTANEOUS ANALYTE SENSOR" which are incorporated herein by reference in their entirety.

The sensing membranes of the preferred embodiments can include any membrane configuration suitable for use with any analyte sensor (such as described in more detail above). In general, the sensing membranes of the preferred embodiments include one or more domains, all or some of which can be adhered to or deposited on the analyte sensor as is appreciated by one skilled in the art. In one embodiment, the sensing membrane generally provides one or more of the following functions: 1) protection of the exposed electrode surface from the biological environment, 2) diffusion resistance (limitation) of the analyte, 3) a catalyst for enabling an enzymatic reaction, 4) limitation or blocking of interfering species, and 5) hydrophilicity at the electrochemically reactive surfaces of the sensor interface, such as described in the above-referenced co-pending U.S. patent applications.

Electrode Domain

In some embodiments, the membrane system comprises an optional electrode domain. The electrode domain is provided to ensure that an electrochemical reaction occurs between the electroactive surfaces of the working electrode and the reference electrode, and thus the electrode domain is preferably situated more proximal to the electroactive surfaces than the enzyme domain. Preferably, the electrode domain includes a semipermeable coating that maintains a layer of water at the electrochemically reactive surfaces of the sensor, for example, a humectant in a binder material can be employed as an electrode domain; this allows for the full transport of ions in the aqueous environment. The electrode domain can also assist in stabilizing the operation of the sensor by overcoming electrode start-up and drifting problems caused by inadequate electrolyte. The material that forms the electrode domain can also protect against pH-mediated damage that can result from the formation of a large pH gradient due to the electrochemical activity of the electrodes.

In one embodiment, the electrode domain includes a flexible, water-swellable, hydrogel film having a "dry film" thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. "Dry film" thickness refers to the thickness of a cured film cast from a coating formulation by standard coating techniques.

In certain embodiments, the electrode domain is formed of a curable mixture of a urethane polymer and a hydrophilic polymer. Particularly preferred coatings are formed of a polyurethane polymer having carboxylate functional groups and non-ionic hydrophilic polyether segments, wherein the polyurethane polymer is crosslinked with a water soluble carbodiimide (e.g., 1-ethyl-3-(3-dimethylaminopropyl)carbodiimide (EDC))) in the presence of polyvinylpyrrolidone and cured at a moderate temperature of about 50° C.

Preferably, the electrode domain is deposited by spray or dip-coating the electroactive surfaces of the sensor. More preferably, the electrode domain is formed by dip-coating the electroactive surfaces in an electrode solution and curing the domain for a time of from about 15 to about 30 minutes at a temperature of from about 40 to about 55° C. (and can be accomplished under vacuum (e.g., 20 to 30 mmHg)). In embodiments wherein dip-coating is used to deposit the electrode domain, a preferred insertion rate of from about 1 to about 3 inches per minute, with a preferred dwell time of from about 0.5 to about 2 minutes, and a preferred withdrawal rate of from about 0.25 to about 2 inches per minute provide a functional coating. However, values outside of those set forth above can be acceptable or even desirable in certain embodiments, for example, dependent upon viscosity and surface tension as is appreciated by one skilled in the art. In one embodiment, the electroactive surfaces of the electrode system are dip-coated one time (one layer) and cured at 50° C. under vacuum for 20 minutes.

Although an independent electrode domain is described herein, in some embodiments, sufficient hydrophilicity can be provided in the interference domain and/or enzyme domain (the domain adjacent to the electroactive surfaces) so as to provide for the full transport of ions in the aqueous environment (e.g. without a distinct electrode domain).

Interference Domain

In some embodiments, an optional interference domain is provided, which generally includes a polymer domain that restricts the flow of one or more interferants. In some embodiments, the interference domain functions as a molecular sieve that allows analytes and other substances that are to be measured by the electrodes to pass through, while preventing passage of other substances, including interferants such as ascorbate and urea (see U.S. Pat. No. 6,001,067 to Shults). Some known interferants for a glucose-oxidase based electrochemical sensor include acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides, and uric acid.

Several polymer types that can be utilized as a base material for the interference domain include polyurethanes, polymers having pendant ionic groups, and polymers having controlled pore size, for example. In one embodiment, the interference domain includes a thin, hydrophobic membrane that is non-swellable and restricts diffusion of low molecular weight species. The interference domain is permeable to relatively low molecular weight substances, such as hydrogen peroxide, but restricts the passage of higher molecular weight substances, including glucose and ascorbic acid. Other systems and methods for reducing or eliminating interference species that can be applied to the membrane system of the preferred embodiments are described in co-pending U.S. patent application Ser. No. 10/896,312 filed Jul. 21, 2004 and entitled "ELECTRODE SYSTEMS FOR ELECTROCHEMICAL SENSORS," Ser. No. 10/991,353, filed Nov. 16, 2004 and entitled, "AFFINITY DOMAIN FOR AN ANALYTE SENSOR," Ser. No. 11/007,635, filed Dec. 7, 2004 and entitled "SYSTEMS AND METHODS FOR IMPROVING ELECTROCHEMICAL ANALYTE SENSORS" and Ser. No. 11/004,561, filed Dec. 3, 2004 and entitled, "CALIBRATION TECHNIQUES FOR A CONTINUOUS ANALYTE SENSOR." In some alternative embodiments, a distinct interference domain is not included.

In preferred embodiments, the interference domain is deposited onto the electrode domain (or directly onto the electroactive surfaces when a distinct electrode domain is not included) for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. Thicker membranes can also be useful, but thinner membranes are generally preferred because they have a lower impact on the rate of diffusion of hydrogen peroxide from the enzyme membrane to the electrodes. Unfortunately, the thin thickness of the interference domains conventionally used can introduce variability in the membrane system processing. For example, if too much or too little interference domain is incorporated within a membrane system, the performance of the membrane can be adversely affected.

Enzyme Domain

In preferred embodiments, the membrane system further includes an enzyme domain disposed more distally from the electroactive surfaces than the interference domain (or electrode domain when a distinct interference is not included). In some embodiments, the enzyme domain is directly deposited onto the electroactive surfaces (when neither an electrode or interference domain is included). In the preferred embodiments, the enzyme domain provides an enzyme to catalyze the reaction of the analyte and its co-reactant, as described in more detail below. Preferably, the enzyme domain includes glucose oxidase; however other oxidases, for example, galactose oxidase or uricase oxidase, can also be used.

For an enzyme-based electrochemical glucose sensor to perform well, the sensor's response is preferably limited by neither enzyme activity nor co-reactant concentration. Because enzymes, including glucose oxidase, are subject to deactivation as a function of time even in ambient conditions, this behavior is compensated for in forming the enzyme domain. Preferably, the enzyme domain is constructed of aqueous dispersions of colloidal polyurethane polymers including the enzyme. However, in alternative embodiments the enzyme domain is constructed from an oxygen enhancing material, for example, silicone, or fluorocarbon, in order to provide a supply of excess oxygen during transient ischemia. Preferably, the enzyme is immobilized within the domain. See U.S. patent application Ser. No. 10/896,639 filed on Jul. 21, 2004 and entitled "Oxygen Enhancing Membrane Systems for Implantable Device."

In preferred embodiments, the enzyme domain is deposited onto the interference domain for a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. However in some embodiments, the enzyme domain is deposited onto the electrode domain or directly onto the electroactive surfaces. Preferably, the enzyme domain is deposited by spray or dip coating. More preferably, the enzyme domain is formed by dip-coating the electrode domain into an enzyme domain solution and curing the domain for from about 15 to about 30 minutes at a temperature of from about 40 to about 55° C. (and can be accomplished under vacuum (e.g., 20 to 30 mmHg)). In embodiments wherein dip-coating is used to deposit the enzyme domain at room temperature, a preferred insertion rate of from about 1 inch per minute to about 3 inches per minute, with a preferred dwell time of from about 0.5 minutes to about 2 minutes, and a preferred withdrawal rate of from about 0.25 inch per minute to about 2 inches per minute provide a functional coating. However, values outside of those set forth above can be acceptable or even desirable in certain embodiments, for example, dependent upon viscosity and surface tension as is appreciated by one skilled in the art. In one embodiment, the enzyme domain is formed by dip coating two times (namely, forming two layers) in a coating solution and curing at 50° C. under vacuum for 20 minutes. However, in some embodiments, the enzyme domain can be formed by dip-coating and/or spray-coating one or more layers at a predetermined concentration of the coating solution, insertion rate, dwell time, withdrawal rate, and/or desired thickness.

Resistance Domain

In preferred embodiments, the membrane system includes a resistance domain disposed more distal from the electroactive surfaces than the enzyme domain. Although the following description is directed to a resistance domain for a glucose sensor, the resistance domain can be modified for other analytes and co-reactants as well.

There exists a molar excess of glucose relative to the amount of oxygen in blood; that is, for every free oxygen molecule in extracellular fluid, there are typically more than 100 glucose molecules present (see Updike et al., Diabetes Care 5:207-21(1982)). However, an immobilized enzyme-based glucose sensor employing oxygen as co-reactant is preferably supplied with oxygen in non-rate-limiting excess in order for the sensor to respond linearly to changes in glucose concentration, while not responding to changes in oxygen concentration. Specifically, when a glucose-monitoring reaction is oxygen limited, linearity is not achieved above minimal concentrations of glucose. Without a semipermeable membrane situated over the enzyme domain to control the flux of glucose and oxygen, a linear response to glucose levels can be obtained only for glucose concentrations of up to about 40 mg/dL. However, in a clinical setting, a linear response to glucose levels is desirable up to at least about 400 mg/dL.

The resistance domain includes a semi permeable membrane that controls the flux of oxygen and glucose to the underlying enzyme domain, preferably rendering oxygen in a non-rate-limiting excess. As a result, the upper limit of linearity of glucose measurement is extended to a much higher value than that which is achieved without the resistance domain. In one embodiment, the resistance domain exhibits an oxygen to glucose permeability ratio of from about 50:1 or less to about 400:1 or more, preferably about 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In alternative embodiments, a lower ratio of oxygen-to-glucose can be sufficient to provide excess oxygen by using a high oxygen solubility domain (for example, a silicone or fluorocarbon-based material or domain) to enhance the supply/transport of oxygen to the enzyme domain. If more oxygen is supplied to the enzyme, then more glucose can also be supplied to the enzyme without creating an oxygen rate-limiting excess. In alternative embodiments, the resistance domain is formed from a silicone composition, such as is described in co-pending U.S. application Ser. No. 10/695, 636 filed Oct. 28, 2003 and entitled, "SILICONE COMPOSITION FOR BIOCOMPATIBLE MEMBRANE."

In a preferred embodiment, the resistance domain includes a polyurethane membrane with both hydrophilic and hydrophobic regions to control the diffusion of glucose and oxygen to an analyte sensor, the membrane being fabricated easily and reproducibly from commercially available materials. A suitable hydrophobic polymer component is a polyurethane, or polyetherurethaneurea. Polyurethane is a polymer produced by the condensation reaction of a diisocyanate and a difunctional hydroxyl-containing material. A polyurethaneurea is a polymer produced by the condensation reaction of a diisocyanate and a difunctional amine-containing material. Preferred diisocyanates include aliphatic diisocyanates containing from about 4 to about 8 methylene units. Diisocyanates containing cycloaliphatic moieties can also be useful in the preparation of the polymer and copolymer components of the membranes of preferred embodiments. The material that forms the basis of the hydrophobic matrix of the resistance domain can be any of those known in the art as appropriate for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In a preferred embodiment, the hydrophilic polymer component is polyethylene oxide. For example, one useful hydrophobic-hydrophilic copolymer component is a polyurethane polymer that includes about 20% hydrophilic polyethylene oxide. The polyethylene oxide portions of the copolymer are thermodynamically driven to separate from the hydrophobic portions of the copolymer and the hydrophobic polymer component. The 20% polyethylene oxide-based soft segment portion of the copolymer used to form the final blend affects the water pick-up and subsequent glucose permeability of the membrane.

In preferred embodiments, the resistance domain is deposited onto the enzyme domain to yield a domain thickness of from about 0.05 micron or less to about 20 microns or more, more preferably from about 0.05, 0.1, 0.15, 0.2, 0.25, 0.3, 0.35, 0.4, 0.45, 0.5, 1, 1.5, 2, 2.5, 3, or 3.5 to about 4, 5, 6, 7, 8, 9, 10, 11, 12, 13, 14, 15, 16, 17, 18, 19, or 19.5 microns, and more preferably from about 2, 2.5 or 3 microns to about 3.5, 4, 4.5, or 5 microns. Preferably, the resistance domain is deposited onto the enzyme domain by spray coating or dip coating. In certain embodiments, spray coating is the preferred deposition technique. The spraying process atomizes and mists the solution, and therefore most or all of the solvent is evaporated prior to the coating material settling on the underlying domain, thereby minimizing contact of the solvent with the enzyme. One additional advantage of spray-coating the resistance domain as described in the preferred embodiments includes formation of a membrane system that substantially blocks or resists ascorbate (a known electrochemical interferant in hydrogen peroxide-measuring glucose sensors). While not wishing to be bound by theory, it is believed that during the process of depositing the resistance domain as described in the preferred embodiments, a structural morphology is formed, characterized in that ascorbate does not substantially permeate there through.

In preferred embodiments, the resistance domain is deposited on the enzyme domain by spray-coating a solution of from about 1 wt. % to about 5 wt. % polymer and from about 95 wt. % to about 99 wt. % solvent. In spraying a solution of resistance domain material, including a solvent, onto the enzyme domain, it is desirable to mitigate or substantially reduce any contact with enzyme of any solvent in the spray solution that can deactivate the underlying enzyme of the enzyme domain. Tetrahydrofuran (THF) is one solvent that minimally or negligibly affects the enzyme of the enzyme domain upon spraying. Other solvents can also be suitable for use, as is appreciated by one skilled in the art.

Although a variety of spraying or deposition techniques can be used, spraying the resistance domain material and rotating the sensor at least one time by 180° can provide adequate coverage by the resistance domain. Spraying the resistance domain material and rotating the sensor at least two times by 120 degrees provides even greater coverage (one layer of 360° coverage), thereby ensuring resistivity to glucose, such as is described in more detail above.

In preferred embodiments, the resistance domain is spray-coated and subsequently cured for a time of from about 15 to about 90 minutes at a temperature of from about 40 to about 60° C. (and can be accomplished under vacuum (e.g., 20 to 30 mmHg)). A cure time of up to about 90 minutes or more can be advantageous to ensure complete drying of the resistance domain. While not wishing to be bound by theory, it is believed that complete drying of the resistance domain aids in stabilizing the sensitivity of the glucose sensor signal. It reduces drifting of the signal sensitivity over time, and complete drying is believed to stabilize performance of the glucose sensor signal in lower oxygen environments.

In one embodiment, the resistance domain is formed by spray-coating at least six layers (namely, rotating the sensor seventeen times by 120° for at least six layers of 360° coverage) and curing at 50° C. under vacuum for 60 minutes. However, the resistance domain can be formed by dip-coating or spray-coating any layer or plurality of layers, depending upon the concentration of the solution, insertion rate, dwell time, withdrawal rate, and/or the desired thickness of the resulting film.

Advantageously, sensors with the membrane system of the preferred embodiments, including an electrode domain and/or interference domain, an enzyme domain, and a resistance domain, provide stable signal response to increasing glucose levels of from about 40 to about 400 mg/dL, and sustained function (at least 90% signal strength) even at low oxygen levels (for example, at about 0.6 mg/L $O_2$). While not wishing to be bound by theory, it is believed that the resistance domain provides sufficient resistivity, or the enzyme domain provides sufficient enzyme, such that oxygen limitations are seen at a much lower concentration of oxygen as compared to prior art sensors.

In preferred embodiments, a sensor signal with a current in the picoAmp range is preferred, which is described in more detail elsewhere herein. However, the ability to produce a signal with a current in the picoAmp range can be dependent upon a combination of factors, including the electronic circuitry design (e.g., A/D converter, bit resolution, and the like), the membrane system (e.g., permeability of the analyte through the resistance domain, enzyme concentration, and/or electrolyte availability to the electrochemical reaction at the electrodes), and the exposed surface area of the working electrode. For example, the resistance domain can be designed to be more or less restrictive to the analyte depending upon to the design of the electronic circuitry, membrane system, and/or exposed electroactive surface area of the working electrode.

Accordingly, in preferred embodiments, the membrane system is designed with a sensitivity of from about 1 pA/mg/dL to about 100 pA/mg/dL, preferably from about 5 pA/mg/dL to 25 pA/mg/dL, and more preferably from about 4 to about 7 pA/mg/dL. While not wishing to be bound by any particular theory, it is believed that membrane systems designed with a sensitivity in the preferred ranges permit measurement of the analyte signal in low analyte and/or low oxygen situations. Namely, conventional analyte sensors have shown reduced measurement accuracy in low analyte ranges due to lower availability of the analyte to the sensor and/or have shown increased signal noise in high analyte ranges due to insufficient oxygen necessary to react with the amount of analyte being measured. While not wishing to be bound by theory, it is believed that the membrane systems of the preferred embodiments, in combination with the electronic circuitry design and exposed electrochemical reactive surface area design, support measurement of the analyte in the picoAmp range, which enables an improved level of resolution and accuracy in both low and high analyte ranges not seen in the prior art.

Although sensors of some embodiments described herein include an optional interference domain in order to block or reduce one or more interferants, sensors with the membrane system of the preferred embodiments, including an electrode domain, an enzyme domain, and a resistance domain, have been shown to inhibit ascorbate without an additional interference domain. Namely, the membrane system of the preferred embodiments, including an electrode domain, an enzyme domain, and a resistance domain, has been shown to be substantially non-responsive to ascorbate in physiologically acceptable ranges. While not wishing to be bound by theory, it is believed that the process of depositing the resistance domain by spray coating, as described herein, results in a structural morphology that is substantially resistance resistant to ascorbate.

Interference-Free Membrane Systems

In general, it is believed that appropriate solvents and/or deposition methods can be chosen for one or more of the domains of the membrane system that form one or more transitional domains such that interferants do not substantially permeate there through. Thus, sensors can be built without distinct or deposited interference domains, which are non-responsive to interferants. While not wishing to be bound by theory, it is believed that a simplified multilayer membrane system, more robust multilayer manufacturing process, and reduced variability caused by the thickness and associated oxygen and glucose sensitivity of the deposited micron-thin interference domain can be provided. Additionally, the optional polymer-based interference domain, which usually inhibits hydrogen peroxide diffusion, is eliminated, thereby enhancing the amount of hydrogen peroxide that passes through the membrane system.

Oxygen Conduit

As described above, certain sensors depend upon an enzyme within the membrane system through which the host's bodily fluid passes and in which the analyte (for example, glucose) within the bodily fluid reacts in the presence of a co-reactant (for example, oxygen) to generate a product. The product is then measured using electrochemical methods, and thus the output of an electrode system functions as a measure of the analyte. For example, when the sensor is a glucose oxidase based glucose sensor, the species measured at the working electrode is $H_2O_2$. An enzyme, glucose oxidase, catalyzes the conversion of oxygen and glucose to hydrogen peroxide and gluconate according to the following reaction:

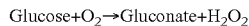

Glucose+$O_2$→Gluconate+$H_2O_2$

Because for each glucose molecule reacted there is a proportional change in the product, $H_2O_2$, one can monitor the change in $H_2O_2$ to determine glucose concentration. Oxidation of $H_2O_2$ by the working electrode is balanced by reduction of ambient oxygen, enzyme generated $H_2O_2$ and other reducible species at a counter electrode, for example. See Fraser, D. M., "An Introduction to In Vivo Biosensing: Progress and Problems." In "Biosensors and the Body," D. M. Fraser, ed., 1997, pp. 1-56 John Wiley and Sons, New York))

In vivo, glucose concentration is generally about one hundred times or more that of the oxygen concentration. Consequently, oxygen is a limiting reactant in the electrochemical reaction, and when insufficient oxygen is provided to the sensor, the sensor is unable to accurately measure glucose concentration. Thus, depressed sensor function or inaccuracy is believed to be a result of problems in availability of oxygen to the enzyme and/or electroactive surface(s).

Accordingly, in an alternative embodiment, an oxygen conduit (for example, a high oxygen solubility domain formed from silicone or fluorochemicals) is provided that extends from the ex vivo portion of the sensor to the in vivo portion of the sensor to increase oxygen availability to the enzyme. The oxygen conduit can be formed as a part of the coating (insulating) material or can be a separate conduit associated with the assembly of wires that forms the sensor.

Figure 2B:
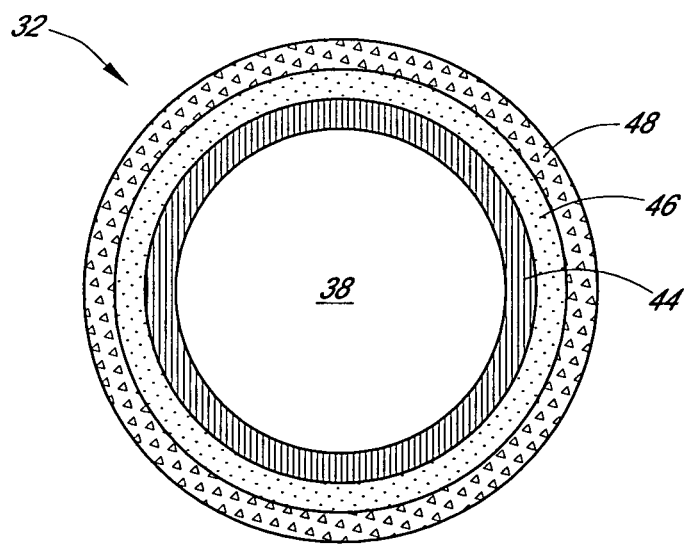
FIG. 2B is a cross-sectional view through the sensor of FIG. 2A on line B-B.

FIG. 2B is a cross-sectional view through the sensor of FIG. 2A on line B-B, showing an exposed electroactive surface of at least a working electrode 38 surrounded by a sensing membrane. In general, the sensing membranes of the preferred embodiments include a plurality of domains or layers, for example, an interference domain 44, an enzyme domain 46, and a resistance domain 48, and may include additional domains, such as an electrode domain, a cell impermeable domain, and/or an oxygen domain (not shown), such as described in more detail in the above-cited co-pending U.S. patent applications. However, it is understood that a sensing membrane modified for other sensors, for example, by including fewer or additional domains is within the scope of the preferred embodiments. In some embodiments, one or more domains of the sensing membranes are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, poly(ethylene oxide), poly(propylene oxide) and copolymers and blends thereof, polysulfones and block copolymers thereof including, for example, di-block, tri-block, alternating, random and graft copolymers. Co-pending U.S. patent application Ser. No. 10/838,912, which is incorporated herein by reference in its entirety, describes biointerface and sensing membrane configurations and materials that may be applied to the preferred embodiments.

The sensing membrane can be deposited on the electroactive surfaces of the electrode material using known thin or thick film techniques (for example, spraying, electro-depositing, dipping, or the like). It is noted that the sensing membrane that surrounds the working electrode does not have to be the same structure as the sensing membrane that surrounds a reference electrode, etc. For example, the enzyme domain deposited over the working electrode does not necessarily need to be deposited over the reference and/or counter electrodes.

In the illustrated embodiment, the sensor is an enzyme-based electrochemical sensor, wherein the working electrode 38 measures the hydrogen peroxide produced by the enzyme catalyzed reaction of glucose being detected and creates a measurable electronic current (for example, detection of glucose utilizing glucose oxidase produces hydrogen peroxide as a by-product, $H_2O_2$ reacts with the surface of the working electrode producing two protons ($2H^+$), two electrons ($2e^-$) and one molecule of oxygen ($O_2$) which produces the electronic current being detected), such as described in more detail above and as is appreciated by one skilled in the art. Preferably, one or more potentiostat is employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrode. The output signal is typically a raw data stream that is used to provide a useful value of the measured analyte concentration in a host to the host or doctor, for example.

Some alternative analyte sensors that can benefit from the systems and methods of the preferred embodiments include U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,512,939 to Colvin et al., U.S. Pat. No. 6,424,847 to Mastrototaro et al., U.S. Pat. No. 6,424,847 to Mastrototaro et al., for example. All of the above patents are incorporated in their entirety herein by reference and are not inclusive of all applicable analyte sensors; in general, it should be understood that the disclosed embodiments are applicable to a variety of analyte sensor configurations.

Exemplary Sensor Configurations

Figure 3A:
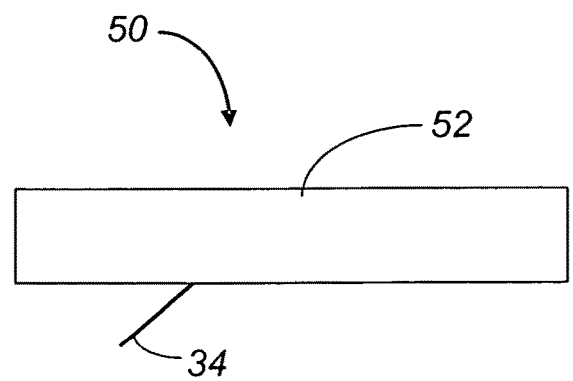
FIG. 3A is a side schematic view of a transcutaneous analyte sensor in one embodiment.

FIG. 3A is a side schematic view of a transcutaneous analyte sensor 50 in one embodiment. The sensor 50 includes a mounting unit 52 adapted for mounting on the skin of a host, a small diameter sensor 34 (as defined herein) adapted for transdermal insertion through the skin of a host, and an electrical connection configured to provide secure electrical contact between the sensor and the electronics preferably housed within the mounting unit 52. In general, the mounting unit 52 is designed to maintain the integrity of the sensor in the host so as to reduce or eliminate translation of motion between the mounting unit, the host, and/or the sensor. See co-pending U.S. patent application Ser. No. 11/077,715 filed on Mar. 10, 2005 and entitled, "TRANSCUTANEOUS ANALYTE SENSOR," which is incorporated herein by reference in its entirety. Preferably, a biointerface membrane is formed onto the sensing mechanism 34 as described in more detail below.

Figure 3B:
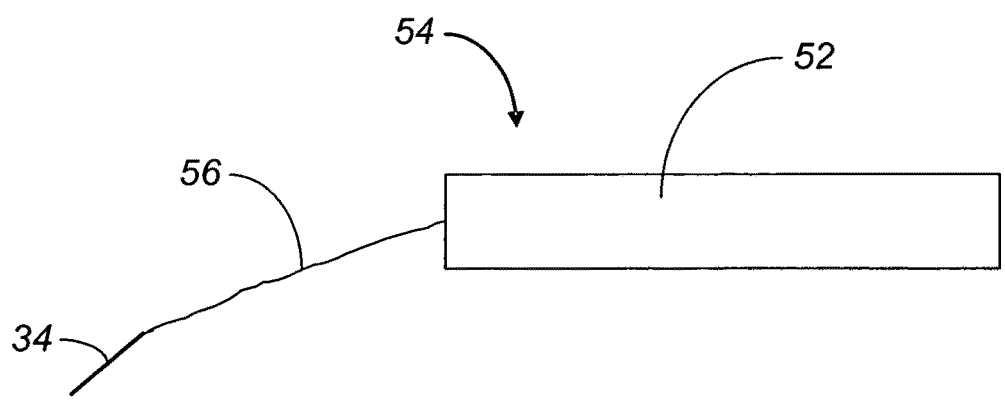
FIG. 3B is a side schematic view of a transcutaneous analyte sensor in an alternative embodiment.

FIG. 3B is a side schematic view of a transcutaneous analyte sensor 54 in an alternative embodiment. The sensor 54 includes a mounting unit 52 wherein the sensing mechanism 34 comprises a small structure as defined herein and is tethered to the mounting unit 52 via a cable 56 (alternatively, a wireless connection can be utilized). The mounting unit is adapted for mounting on the skin of a host and is operably connected via a tether, or the like, to a small structured sensor 34 adapted for transdermal insertion through the skin of a host and measurement of the analyte therein; see, for example, U.S. Pat. No. 6,558,330 to Causey III et al., which is incorporated herein by reference in its entirety. In the preferred embodiments, a biointerface membrane is formed onto the sensing mechanism 34 as described in more detail below.

The short-term sensor of the preferred embodiments may be inserted into a variety of locations on the host's body, such as the abdomen, the thigh, the upper arm, and the neck or behind the ear. Although the preferred embodiments illustrate insertion through the abdominal region, the systems and methods described herein are limited neither to the abdominal nor to the subcutaneous insertions. One skilled in the art appreciates that these systems and methods may be implemented and/or modified for other insertion sites and may be dependent upon the type, configuration, and dimensions of the analyte sensor.

In one embodiment, an analyte-sensing device adapted for transcutaneous short-term insertion into the host is provided. For example, the device includes a sensor, for measuring the analyte in the host, a porous, biocompatible matrix covering at least a portion of the sensor, and an applicator, for inserting the sensor through the host's skin. In some embodiments, the sensor has architecture with at least one dimension less than about 1 mm. Examples of such a structure are shown in FIGS. 3A and 3B, as described elsewhere herein. However, one skilled in the art will recognize that alternative configurations are possible and may be desirable, depending upon factors such as intended location of insertion, for example. The sensor is inserted through the host's skin and into the underlying tissue, such as soft tissue or fatty tissue.

After insertion, fluid moves into the spacer, e.g., a biocompatible matrix or membrane, creating a fluid-filled pocket therein. This process may occur immediately or may take place over a period of time, such as several minutes or hours post insertion. A signal from the sensor is then detected, such as by the sensor electronics unit located in the mounting unit on the surface of the host's skin. In general, the sensor may be used continuously for a short period of days, such as 1 to 14 days. After use, the sensor is simply removed from the host's skin. In preferred embodiments, the host may repeat the insertion and detection steps as many times as desired. In some implementations, the sensor may be removed after about 3 days, and then another sensor inserted, and so on. Similarly in other implementations, the sensor is removed after about 3, 5, 7, 10 or 14 days, followed by insertion of a new sensor, and so on.

Some examples of transcutaneous analyte sensors are described in co-pending U.S. patent application Ser. No. 11/360,250 and entitled "ANALYTE SENSOR," which is incorporated herein by reference in its entirety. In general, transcutaneous analyte sensors comprise the sensor and a mounting unit with electronics associated therewith.

In general, the mounting unit includes a base adapted for mounting on the skin of a host, a sensor adapted for transdermal insertion through the skin of a host, and one or more contacts configured to provide secure electrical contact between the sensor and the sensor electronics. The mounting unit is designed to maintain the integrity of the sensor in the host so as to reduce or eliminate translation of motion between the mounting unit, the host, and/or the sensor. The base can be formed from a variety of hard or soft materials, and preferably comprises a low profile for minimizing protrusion of the device from the host during use. In some embodiments, the base is formed at least partially from a flexible material, which is believed to provide numerous advantages over conventional transcutaneous sensors, which, unfortunately, can suffer from motion-related artifacts associated with the host's movement when the host is using the device. For example, when a transcutaneous analyte sensor is inserted into the host, various movements of the sensor (for example, relative movement between the in vivo portion and the ex vivo portion, movement of the skin, and/or movement within the host (dermis or subcutaneous)) create stresses on the device and can produce noise in the sensor signal. It is believed that even small movements of the skin can translate to discomfort and/or motion-related artifact, which can be reduced or obviated by a flexible or articulated base. Thus, by providing flexibility and/or articulation of the device against the host's skin, better conformity of the sensor system to the regular use and movements of the host can be achieved. Flexibility or articulation is believed to increase adhesion (with the use of an adhesive pad) of the mounting unit onto the skin, thereby decreasing motion-related artifact that can otherwise translate from the host's movements and reduced sensor performance.

In certain embodiments, the mounting unit is provided with an adhesive pad, preferably disposed on the mounting unit's back surface and preferably including a releasable backing layer. Thus, removing the backing layer and pressing the base portion of the mounting unit onto the host's skin adheres the mounting unit to the host's skin. Additionally or alternatively, an adhesive pad can be placed over some or all of the sensor system after sensor insertion is complete to ensure adhesion, and optionally to ensure an airtight seal or watertight seal around the wound exit-site (or sensor insertion site). Appropriate adhesive pads can be chosen and designed to stretch, elongate, conform to, and/or aerate the region (e.g., host's skin).

In preferred embodiments, the adhesive pad is formed from spun-laced, open- or closed-cell foam, and/or non-woven fibers, and includes an adhesive disposed thereon, however a variety of adhesive pads appropriate for adhesion to the host's skin can be used, as is appreciated by one skilled in the art of medical adhesive pads. In some embodiments, a double-sided adhesive pad is used to adhere the mounting unit to the host's skin. In other embodiments, the adhesive pad includes a foam layer, for example, a layer wherein the foam is disposed between the adhesive pad's side edges and acts as a shock absorber.

In some embodiments, the surface area of the adhesive pad is greater than the surface area of the mounting unit's back surface. Alternatively, the adhesive pad can be sized with substantially the same surface area as the back surface of the base portion. Preferably, the adhesive pad has a surface area on the side to be mounted on the host's skin that is greater than about 1, 1.25, 1.5, 1.75, 2, 2.25, or 2.5, times the surface area of the back surface of the mounting unit base. Such a greater surface area can increase adhesion between the mounting unit and the host's skin, minimize movement between the mounting unit and the host's skin, and/or protect the wound exit-site (sensor insertion site) from environmental and/or biological contamination. In some alternative embodiments, however, the adhesive pad can be smaller in surface area than the back surface assuming a sufficient adhesion can be accomplished.

In some embodiments, the adhesive pad is substantially the same shape as the back surface of the base, although other shapes can also be advantageously employed, for example, butterfly-shaped, round, square, or rectangular. The adhesive pad backing can be designed for two-step release, for example, a primary release wherein only a portion of the adhesive pad is initially exposed to allow adjustable positioning of the device, and a secondary release wherein the remaining adhesive pad is later exposed to firmly and securely adhere the device to the host's skin once appropriately positioned. The adhesive pad is preferably waterproof. Preferably, a stretch-release adhesive pad is provided on the back surface of the base portion to enable easy release from the host's skin at the end of the useable life of the sensor.

In some circumstances, it has been found that a conventional bond between the adhesive pad and the mounting unit may not be sufficient, for example, due to humidity that can cause release of the adhesive pad from the mounting unit. Accordingly, in some embodiments, the adhesive pad can be bonded using a bonding agent activated by or accelerated by an ultraviolet, acoustic, radio frequency, or humidity cure. In some embodiments, a eutectic bond of first and second composite materials can form a strong adhesion. In some embodiments, the surface of the mounting unit can be pretreated utilizing ozone, plasma, chemicals, or the like, in order to enhance the bondability of the surface.

A bioactive agent is preferably applied locally at the insertion site prior to or during sensor insertion. Suitable bioactive agents include those which are known to discourage or prevent bacterial growth and infection, for example, anti-inflammatory agents, antimicrobials, antibiotics, or the like. It is believed that the diffusion or presence of a bioactive agent can aid in prevention or elimination of bacteria adjacent to the exit-site. Additionally or alternatively, the bioactive agent can be integral with or coated on the adhesive pad, or no bioactive agent at all is employed.

In some embodiments, an applicator is provided for inserting the sensor through the host's skin at the appropriate insertion angle with the aid of a needle, and for subsequent removal of the needle using a continuous push-pull action. Preferably, the applicator comprises an applicator body that guides the applicator and includes an applicator body base configured to mate with the mounting unit during insertion of the sensor into the host. The mate between the applicator body base and the mounting unit can use any known mating configuration, for example, a snap-fit, a press-fit, an interference-fit, or the like, to discourage separation during use. One or more release latches enable release of the applicator body base, for example, when the applicator body base is snap fit into the mounting unit.

The sensor electronics includes hardware, firmware, and/or software that enable measurement of levels of the analyte via the sensor. For example, the sensor electronics can comprise a potentiostat, a power source for providing power to the sensor, other components useful for signal processing, and preferably an RF module for transmitting data from the sensor electronics to a receiver. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, or a processor. Preferably, sensor electronics comprise systems and methods for processing sensor analyte data. Examples of systems and methods for processing sensor analyte data are described in more detail below and in co-pending U.S. application Ser. No. 10/633,367 filed Aug. 1, 2003, and entitled, "SYSTEM AND METHODS FOR PROCESSING ANALYTE SENSOR DATA."

In this embodiment, after insertion of the sensor using the applicator, and subsequent release of the applicator from the mounting unit, the sensor electronics are configured to releasably mate with the mounting unit. In one embodiment, the electronics are configured with programming, for example initialization, calibration reset, failure testing, or the like, each time it is initially inserted into the mounting unit and/or each time it initially communicates with the sensor.

Sensor Electronics

The following description of electronics associated with the sensor is applicable to a variety of continuous analyte sensors, such as non-invasive, minimally invasive, and/or invasive (e.g., transcutaneous and wholly implantable) sensors. For example, the sensor electronics and data processing as well as the receiver electronics and data processing described below can be incorporated into the wholly implantable glucose sensor disclosed in co-pending U.S. patent application Ser. No. 10/838,912, filed May 3, 2004 and entitled "IMPLANTABLE ANALYTE SENSOR" and U.S. patent application Ser. No. 10/885,476 filed Jul. 6, 2004 and entitled, "SYSTEMS AND METHODS FOR MANU-

FACTURE OF AN ANALYTE-MEASURING DEVICE INCLUDING A MEMBRANE SYSTEM".

In one embodiment, a potentiostat, which is operably connected to an electrode system (such as described above) provides a voltage to the electrodes, which biases the sensor to enable measurement of an current signal indicative of the analyte concentration in the host (also referred to as the analog portion). In some embodiments, the potentiostat includes a resistor that translates the current into voltage. In some alternative embodiments, a current to frequency converter is provided that is configured to continuously integrate the measured current, for example, using a charge counting device. An A/D converter digitizes the analog signal into a digital signal, also referred to as "counts" for processing. Accordingly, the resulting raw data stream in counts, also referred to as raw sensor data, is directly related to the current measured by the potentiostat.

A processor module includes the central control unit that controls the processing of the sensor electronics. In some embodiments, the processor module includes a microprocessor, however a computer system other than a microprocessor can be used to process data as described herein, for example an ASIC can be used for some or all of the sensor's central processing. The processor typically provides semi-permanent storage of data, for example, storing data such as sensor identifier (ID) and programming to process data streams (for example, programming for data smoothing and/or replacement of signal artifacts such as is described in co-pending U.S. patent application Ser. No. 10/648,849, filed Aug. 22, 2003, and entitled, "SYSTEMS AND METHODS FOR REPLACING SIGNAL ARTIFACTS IN A GLUCOSE SENSOR DATA STREAM"). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, or the like.

In some embodiments, the processor module comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, wherein the potentiostat is configured to measure the analyte at discrete time intervals, these time intervals determine the sample rate of the digital filter. In some alternative embodiments, wherein the potentiostat is configured to continuously measure the analyte, for example, using a current-to-frequency converter as described above, the processor module can be programmed to request a digital value from the A/D converter at a predetermined time interval, also referred to as the acquisition time. In these alternative embodiments, the values obtained by the processor are advantageously averaged over the acquisition time due the continuity of the current measurement. Accordingly, the acquisition time determines the sample rate of the digital filter. In preferred embodiments, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is preferred; however any acquisition time can be programmed into the processor module. A programmable acquisition time is advantageous in optimizing noise filtration, time lag, and processing/battery power.

Preferably, the processor module is configured to build the data packet for transmission to an outside source, for example, an RF transmission to a receiver as described in more detail below. Generally, the data packet comprises a plurality of bits that can include a sensor ID code, raw data, filtered data, and/or error detection or correction. The processor module can be configured to transmit any combination of raw and/or filtered data.

In some embodiments, the processor module further comprises a transmitter portion that determines the transmission interval of the sensor data to a receiver, or the like. In some embodiments, the transmitter portion, which determines the interval of transmission, is configured to be programmable. In one such embodiment, a coefficient can be chosen (e.g., a number of from about 1 to about 100, or more), wherein the coefficient is multiplied by the acquisition time (or sampling rate), such as described above, to define the transmission interval of the data packet. Thus, in some embodiments, the transmission interval is programmable between about 2 seconds and about 850 minutes, more preferably between about 30 second and 5 minutes; however, any transmission interval can be programmable or programmed into the processor module. However, a variety of alternative systems and methods for providing a programmable transmission interval can also be employed. By providing a programmable transmission interval, data transmission can be customized to meet a variety of design criteria (e.g., reduced battery consumption, timeliness of reporting sensor values, etc.)

Conventional glucose sensors measure current in the nanoAmp range. In contrast to conventional glucose sensors, the preferred embodiments are configured to measure the current flow in the picoAmp range, and in some embodiments, femtoAmps. Namely, for every unit (mg/dL) of glucose measured, at least one picoAmp of current is measured. Preferably, the analog portion of the A/D converter is configured to continuously measure the current flowing at the working electrode and to convert the current measurement to digital values representative of the current. In one embodiment, the current flow is measured by a charge counting device (e.g., a capacitor). Thus, a signal is provided, whereby a high sensitivity maximizes the signal received by a minimal amount of measured hydrogen peroxide (e.g., minimal glucose requirements without sacrificing accuracy even in low glucose ranges), reducing the sensitivity to oxygen limitations in vivo (e.g., in oxygen-dependent glucose sensors).

A battery is operably connected to the sensor electronics and provides the power for the sensor. In one embodiment, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-zinc, and/or hermetically-sealed). In some embodiments, the battery is rechargeable, and/or a plurality of batteries can be used to power the system. The sensor can be transcutaneously powered via an inductive coupling, for example. In some embodiments, a quartz crystal is operably connected to the processor and maintains system time for the computer system as a whole, for example for the programmable acquisition time within the processor module.

Optional temperature probe can be provided, wherein the temperature probe is located on the electronics assembly or the glucose sensor itself. The temperature probe can be used to measure ambient temperature in the vicinity of the glucose sensor. This temperature measurement can be used to add temperature compensation to the calculated glucose value.

An RF module is operably connected to the processor and transmits the sensor data from the sensor to a receiver within a wireless transmission via antenna. In some embodiments, a second quartz crystal provides the time base for the RF carrier frequency used for data transmissions from the RF transceiver. In some alternative embodiments, however, other mechanisms, such as optical, infrared radiation (IR), ultrasonic, or the like, can be used to transmit and/or receive data.

In the RF telemetry module of the preferred embodiments, the hardware and software are designed for low power requirements to increase the longevity of the device (for example, to enable a life of from about 3 to about 24 months, or more) with maximum RF transmittance from the in vivo environment to the ex vivo environment for wholly implantable sensors (for example, a distance of from about one to ten meters or more). Preferably, a high frequency carrier signal of from about 402 MHz to about 433 MHz is employed in order to maintain lower power requirements. Additionally, in wholly implantable devices, the carrier frequency is adapted for physiological attenuation levels, which is accomplished by tuning the RF module in a simulated in vivo environment to ensure RF functionality after implantation; accordingly, the preferred glucose sensor can sustain sensor function for 3 months, 6 months, 12 months, or 24 months or more.

In some embodiments, output signal (from the sensor electronics) is sent to a receiver (e.g., a computer or other communication station). The output signal is typically a raw data stream that is used to provide a useful value of the measured analyte concentration to a patient or a doctor, for example. In some embodiments, the raw data stream can be continuously or periodically algorithmically smoothed or otherwise modified to diminish outlying points that do not accurately represent the analyte concentration, for example due to signal noise or other signal artifacts, such as described in co-pending U.S. patent application Ser. No. 10/632,537 entitled, "SYSTEMS AND METHODS FOR REPLACING SIGNAL ARTIFACTS IN A GLUCOSE SENSOR DATA STREAM," filed Aug. 22, 2003, which is incorporated herein by reference in its entirety.

When a sensor is first implanted into host tissue, the sensor and receiver are initialized. This can be referred to as start-up mode, and involves optionally resetting the sensor data and calibrating the sensor. In selected embodiments, mating the electronics unit to the mounting unit triggers a start-up mode. In other embodiments, the start-up mode is triggered by the receiver.

Receiver

In some embodiments, the sensor electronics are wirelessly connected to a receiver via one- or two-way RF transmissions or the like. However, a wired connection is also contemplated. The receiver provides much of the processing and display of the sensor data, and can be selectively worn and/or removed at the host's convenience. Thus, the sensor system can be discreetly worn, and the receiver, which provides much of the processing and display of the sensor data, can be selectively worn and/or removed at the host's convenience. Particularly, the receiver includes programming for retrospectively and/or prospectively initiating a calibration, converting sensor data, updating the calibration, evaluating received reference and sensor data, and evaluating the calibration for the analyte sensor, such as described in more detail with reference to co-pending U.S. patent application Ser. No. 10/633,367, filed Aug. 1, 2003 and entitled, "SYSTEM AND METHODS FOR PROCESSING ANALYTE SENSOR DATA."

Figure 3C:
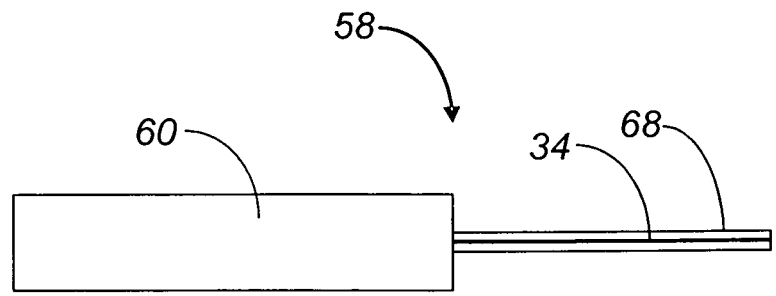
FIG. 3C is a side schematic view of a wholly implantable analyte sensor in one embodiment.

FIG. 3C is a side schematic view of a wholly implantable analyte sensor 58 in one embodiment. The sensor includes a sensor body 60 suitable for subcutaneous implantation and includes a small structured sensor 34 as defined herein. Published U.S. Patent Application No. 2004/0199059 to Brauker et al. describes systems and methods suitable for the sensor body 60, and is incorporated herein by reference in its entirety. In the preferred embodiments, a biointerface membrane 68 is formed onto the sensing mechanism 34 as described in more detail elsewhere herein. The sensor body 60 includes sensor electronics and preferably communicates with a receiver as described in more detail, above.

Figure 3D:
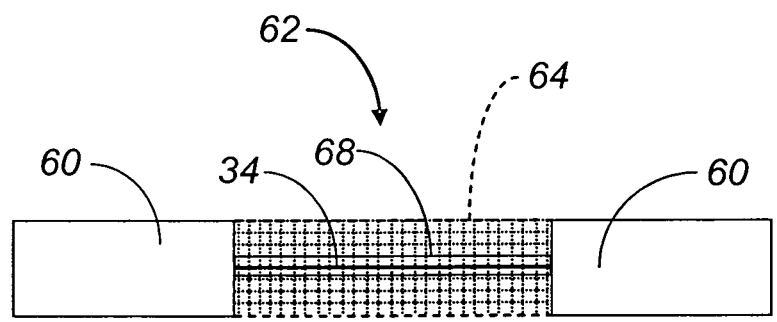
FIG. 3D is a side schematic view of a wholly implantable analyte sensor in an alternative embodiment.

FIG. 3D is a side schematic view of a wholly implantable analyte sensor 62 in an alternative embodiment. The sensor 62 includes a sensor body 60 and a small structured sensor 34 as defined herein. The sensor body 60 includes sensor electronics and preferably communicates with a receiver as described in more detail, above.

In preferred embodiments, a biointerface membrane 68 is formed onto the sensing mechanism 34 as described in more detail elsewhere herein. Preferably, a matrix or framework 64 surrounds the sensing mechanism 34 for protecting the sensor from some foreign body processes, for example, by causing tissue to compress against or around the framework 64 rather than the sensing mechanism 34.

In general, the optional protective framework 64 is formed from a two-dimensional or three-dimensional flexible, semi-rigid, or rigid matrix (e.g., mesh), and which includes spaces or pores through which the analyte can pass. In some embodiments, the framework is incorporated as a part of the biointerface membrane, however a separate framework can be provided. While not wishing to be bound by theory, it is believed that the framework 64 protects the small structured sensing mechanism from mechanical forces created in vivo.

Figure 3E:
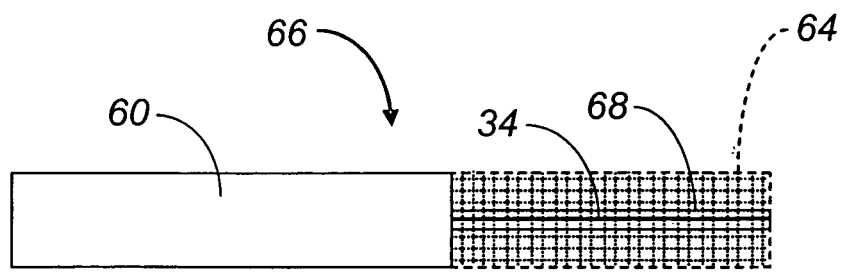
FIG. 3E is a side schematic view of a wholly implantable analyte sensor in another alternative embodiment.

FIG. 3E is a side schematic view of a wholly implantable analyte sensor 66 in another alternative embodiment. The sensor 66 includes a sensor body 60 and a small structured sensor 34, as defined herein, with a biointerface membrane 68 such as described in more detail elsewhere herein. Preferably, a framework 64 protects the sensing mechanism 34 such as described in more detail above. The sensor body 60 includes sensor electronics and preferably communicates with a receiver as described in more detail, above.

In certain embodiments, the sensing device, which is adapted to be wholly implanted into the host, such as in the soft tissue beneath the skin, is implanted subcutaneously, such as in the abdomen of the host, for example. One skilled in the art appreciates a variety of suitable implantation sites available due to the sensor's small size. In some embodiments, the sensor architecture is less than about 0.5 mm in at least one dimension, for example a wire-based sensor with a diameter of less than about 0.5 mm. In another exemplary embodiment, for example, the sensor may be 0.5 mm thick, 3 mm in length and 2 cm in width, such as possibly a narrow substrate, needle, wire, rod, sheet, or pocket. In another exemplary embodiment, a plurality of about 1 mm wide wires about 5 mm in length could be connected at their first ends, producing a forked sensor structure. In still another embodiment, a 1 mm wide sensor could be coiled, to produce a planar, spiraled sensor structure. Although a few examples are cited above, numerous other useful embodiments are contemplated by the present invention, as is appreciated by one skilled in the art.

Post implantation, a period of time is allowed for tissue ingrowth within the biointerface. The length of time required for tissue ingrowth varies from host to host, such as about a week to about 3 weeks, although other time periods are also possible. Once a mature bed of vascularized tissue has grown into the biointerface, a signal can be detected from the sensor, as described elsewhere herein and in U.S. patent application Ser. No. 10/838,912 to Brauker et al., entitled IMPLANTABLE ANALYTE SENSOR, incorporated herein in its entirety. Long term sensors can remain implanted and produce glucose signal information from months to years, as described in the above-cited patent application.

In certain embodiments, the device is configured such that the sensing unit is separated from the electronics unit by a tether or cable, or a similar structure, similar to that illustrated in FIG. 3B. One skilled in the art will recognize that a variety of known and useful means may be used to tether the sensor to the electronics. While not wishing to be bound by theory, it is believed that the FBR to the electronics unit alone may be greater than the FBR to the sensing unit alone, due to the electronics unit's greater mass, for example. Accordingly, separation of the sensing and electronics units effectively reduces the FBR to the sensing unit and results in improved device function. As described elsewhere herein, the architecture and/or composition of the sensing unit (e.g., inclusion of a biointerface with certain bioactive agents) can be implemented to further reduce the foreign body response to the tethered sensing unit.

Figure 3F:
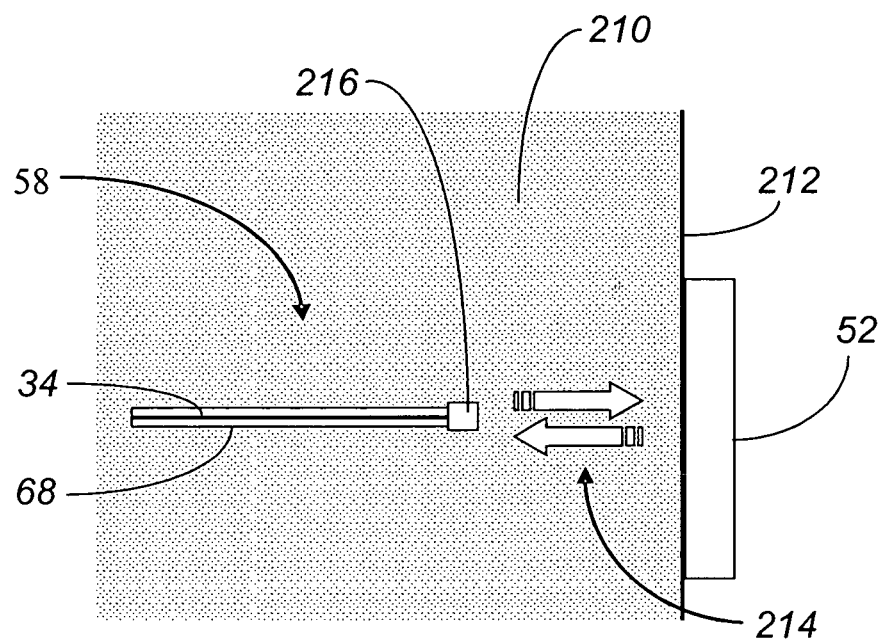
FIG. 3F is a side view of one embodiment of an implanted sensor inductively coupled to an electronics unit within a functionally useful distance on the host's skin.
Figure 3G:
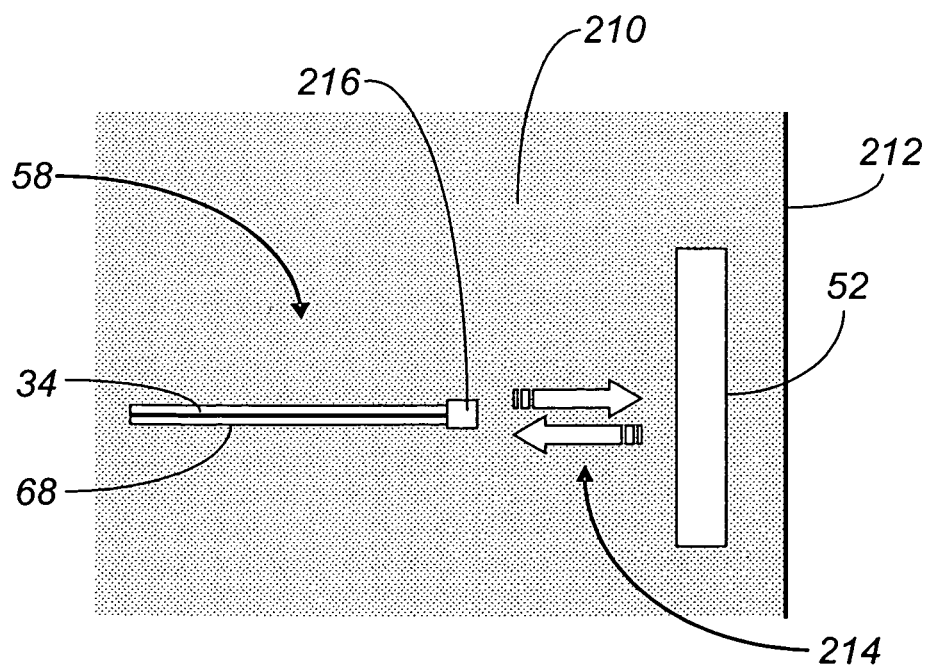
FIG. 3G is a side view of one embodiment of an implanted sensor inductively coupled to an electronics unit implanted in the host's tissue at a functionally useful distance.

In another embodiment, an analyte sensor is designed with separate electronics and sensing units, wherein the sensing unit is inductively coupled to the electronics unit. In this embodiment, the electronics unit provides power to the sensing unit and/or enables communication of data therebetween. FIGS. 3F and 3G illustrate exemplary systems that employ inductive coupling between an electronics unit 52 and a sensing unit 58.

FIG. 3F is a side view of one embodiment of an implanted sensor inductively coupled to an electronics unit within a functionally useful distance on the host's skin. FIG. 3F illustrates a sensing unit 58, including a sensing mechanism 34, biointerface 68 and small electronics chip 216 implanted below the host's skin 212, within the host's tissue 210. In this example, the majority of the electronics associated with the sensor are housed in an electronics unit 52 (also referred to as a mounting unit) located within suitably close proximity on the host's skin. The electronics unit 52 is inductively coupled to the small electronics chip 216 on the sensing unit 58 and thereby transmits power to the sensor and/or collects data, for example. The small electronics chip 216 coupled to the sensing unit 58 provides the necessary electronics to provide a bias potential to the sensor, measure the signal output, and/or other necessary requirements to allow the sensing mechanism 58 to function (e.g., chip 216 can include an ASIC (application specific integrated circuit), antenna, and other necessary components appreciated by one skilled in the art).

In yet another embodiment, the implanted sensor additionally includes a capacitor to provide necessary power for device function. A portable scanner (e.g., wand-like device) is used to collect data stored on the circuit and/or to recharge the device.

In general, inductive coupling, as described herein, enables power to be transmitted to the sensor for continuous power, recharging, and the like. Additionally, inductive coupling utilizes appropriately spaced and oriented antennas (e.g., coils) on the sensing unit and the electronics unit so as to efficiently transmit/receive power (e.g., current) and/or data communication therebetween. One or more coils in each of the sensing and electronics unit can provide the necessary power induction and/or data transmission.

In this embodiment, the sensing mechanism can be, for example, a wire-based sensor as described in more detail with reference to FIGS. 2A and 2B and as described in published U.S. Patent Application US2006-0020187, or a planar substrate-based sensor such as described in U.S. Pat. No. 6,175,752 to Say et al. and U.S. Pat. No. 5,779,665 to Mastrototaro et al., all of which are incorporated herein by reference in their entirety. The biointerface 68 can be any suitable biointerface as described in more detail elsewhere herein, for example, a layer of porous biointerface membrane material, a mesh cage, and the like. In one exemplary embodiment, the biointerface 68 is a single- or multi-layer sheet (e.g., pocket) of porous membrane material, such as ePTFE, in which the sensing mechanism 34 is incorporated.

FIG. 3G is a side view of on embodiment of an implanted sensor inductively coupled to an electronics unit implanted in the host's tissue at a functionally useful distance. FIG. 3G illustrates a sensor unit 58 and an electronics unit 52 similar to that described with reference to FIG. 3F, above, however both are implanted beneath the host's skin in a suitably close proximity.

In general, it is believed that when the electronics unit 52, which carries the majority of the mass of the implantable device, is separate from the sensing unit 58, a lesser foreign body response will occur surrounding the sensing unit (e.g., as compared to a device of greater mass, for example, a device including certain electronics and/or power supply). Thus, the configuration of the sensing unit, including a biointerface, can be optimized to minimize and/or modify the host's tissue response, for example with minimal mass as described in more detail elsewhere.

Biointerface

In preferred embodiments, the sensor includes a porous material disposed over some portion thereof, which modifies the host's tissue response to the sensor. In some embodiments, the porous material surrounding the sensor advantageously enhances and extends sensor performance and lifetime in the short term by slowing or reducing cellular migration to the sensor and associated degradation that would otherwise be caused by cellular invasion if the sensor were directly exposed to the in vivo environment. Alternatively, the porous material can provide stabilization of the sensor via tissue ingrowth into the porous material in the long term. Suitable porous materials include silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, poly(ethylene oxide), poly (propylene oxide) and copolymers and blends thereof, polysulfones and block copolymers thereof including, for example, di-block, tri-block, alternating, random and graft copolymers, as well as metals, ceramics, cellulose, hydrogel polymers, poly(2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(l-lysine), poly(L-lactic acid), hydroxyethylmetharcrylate, hydroxyapeptite, alumina, zirconia, carbon fiber, aluminum, calcium phosphate, titanium, titanium alloy, nintinol, stainless steel, and CoCr alloy, or the like, such as are described in co-pending U.S. patent application Ser. No. 10/842,716, filed May 10, 2004 and entitled, "BIOINTERFACE MEMBRANES INCORPORATING BIOACTIVE AGENTS" and U.S. patent application Ser. No. 10/647,065 filed Aug. 22, 2003 and entitled "POROUS MEMBRANES FOR USE WITH IMPLANTABLE DEVICES."

In some embodiments, the porous material surrounding the sensor provides unique advantages in the short term (e.g., one to 14 days) that can be used to enhance and extend sensor performance and lifetime. However, such materials can also provide advantages in the long term too (e.g., greater than 14 days). Particularly, the in vivo portion of the sensor (the portion of the sensor that is implanted into the host's tissue) is encased (partially or fully) in a porous material. The porous material can be wrapped around the sensor (for example, by wrapping the porous material around the sensor or by inserting the sensor into a section of porous material sized to receive the sensor). Alternately, the porous material can be deposited on the sensor (for example, by electrospinning of a polymer directly thereon). In yet other alternative embodiments, the sensor is inserted into a selected section of porous biomaterial. Other methods for surrounding the in vivo portion of the sensor with a porous material can also be used as is appreciated by one skilled in the art.

The porous material surrounding the sensor advantageously slows or reduces cellular migration to the sensor and associated degradation that would otherwise be caused by cellular invasion if the sensor were directly exposed to the in vivo environment. Namely, the porous material provides a barrier that makes the migration of cells towards the sensor more tortuous and therefore slower (providing short term advantages). It is believed that this reduces or slows the sensitivity loss normally observed in a short-term sensor over time.

In an embodiment wherein the porous material is a high oxygen solubility material, such as porous silicone, the high oxygen solubility porous material surrounds some of or the entire in vivo portion of the sensor. In some embodiments, a lower ratio of oxygen-to-glucose can be sufficient to provide excess oxygen by using a high oxygen soluble domain (for example, a silicone- or fluorocarbon-based material) to enhance the supply/transport of oxygen to the enzyme membrane and/or electroactive surfaces. It is believed that some signal noise normally seen by a conventional sensor can be attributed to an oxygen deficit. Silicone has high oxygen permeability, thus promoting oxygen transport to the enzyme layer. By enhancing the oxygen supply through the use of a silicone composition, for example, glucose concentration can be less of a limiting factor. In other words, if more oxygen is supplied to the enzyme and/or electroactive surfaces, then more glucose can also be supplied to the enzyme without creating an oxygen rate-limiting excess. While not being bound by any particular theory, it is believed that silicone materials provide enhanced bio-stability when compared to other polymeric materials such as polyurethane.

In certain aspects, modifying a small structured sensor with a biointerface structure, material, matrix, and/or membrane that creates a space appropriate for filling with fluid in vivo can enhance sensor performance. In some embodiments, the small structured sensor includes a porous biointerface material, which allows fluid from the surrounding tissues to form a fluid-filled pocket around at least a portion of the sensor. It is believed that the fluid-filled pocket provides a sufficient source of analyte-containing fluid for accurate sensor measurement in the short term. Additionally or alternatively, inclusion of bioactive agents can modify the host's tissue response, for example to reduce or eliminate tissue ingrowth or other cellular responses into the biointerface.

In some aspects, modifying a small structured sensor with a structure, material, and/or membrane/matrix that allows tissue ingrowth without barrier cell formation can enhance sensor performance. For example, a vascularized bed of tissue for long-term analyte sensor measurement. In some embodiments, a porous biointerface membrane, including a plurality of interconnected cavities and a solid portion, covering at least the sensing portion of a small structured sensor allows vascularized tissue ingrowth therein. Vascularized tissue ingrowth provides a sufficient source of analyte-containing tissue in the long term. Additionally or alternatively, inclusion of bioactive agents can modify the host's tissue response, for example to reduce or eliminate barrier cell layer formation within the membrane.

When used herein, the terms "membrane" and "matrix" are meant to be interchangeable. In these embodiments first domain is provided that includes an architecture, including cavity size, configuration, and/or overall thickness, that modifies the host's tissue response, for example, by creating a fluid pocket, encouraging vascularized tissue ingrowth, disrupting downward tissue contracture, resisting fibrous tissue growth adjacent to the device, and/or discouraging barrier cell formation. The biointerface preferably covers at least the sensing mechanism of the sensor and can be of any shape or size, including uniform, asymmetrically, or axi-symmetrically covering or surrounding a sensing mechanism or sensor.

A second domain is optionally provided that is impermeable to cells and/or cell processes. A bioactive agent is optionally provided that is incorporated into the at least one of the first domain, the second domain, the sensing membrane, or other part of the implantable device, wherein the bioactive agent is configured to modify a host tissue response.

Figure 4A:
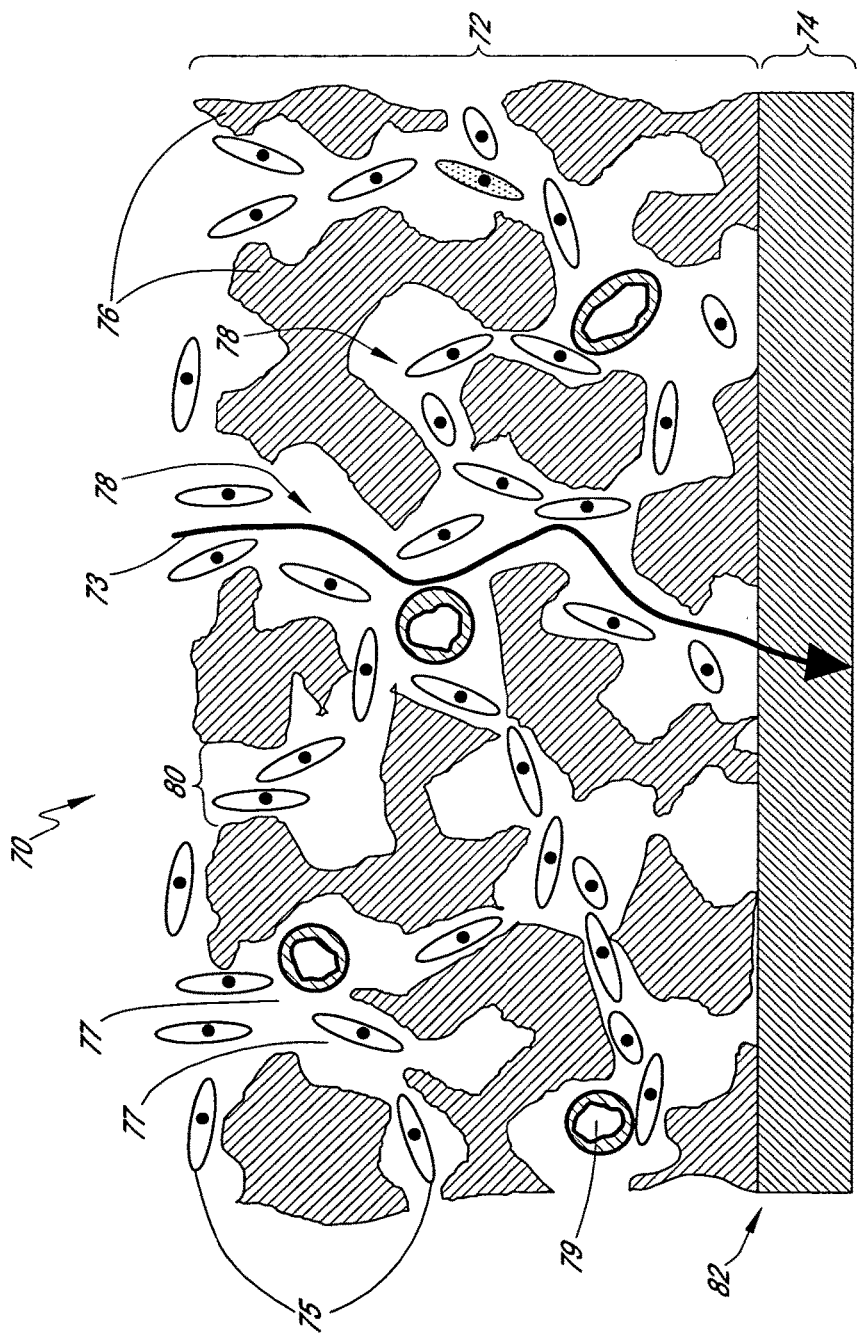
FIG. 4A is a cross-sectional schematic view of a membrane of a preferred embodiment that facilitates vascularization of the first domain without barrier cell layer formation.

FIG. 4A is a cross-sectional schematic view of a biointerface membrane 70 in vivo in one exemplary embodiment, wherein the membrane comprises a first domain 72 and an optional second domain 74. In the short term, the architecture of the biointerface membrane provides a space between the sensor and the host's tissue that allows a fluid filled pocket to form for transport of fluid therein. In the long term, the architecture of the membrane provides a robust, implantable membrane that facilitates the transport of analytes through vascularized tissue ingrowth without the formation of a barrier cell layer.

The first domain 72 comprises a solid portion 76 and a plurality of interconnected three-dimensional cavities 78 formed therein. In this embodiment, the cavities 78 have sufficient size and structure to allow invasive cells, such as fibroblasts 75, a fibrous matrix 77, and blood vessels 79 to enter into the apertures 80 that define the entryway into each cavity 78, and to pass through the interconnected cavities toward the interface 82 between the first and second domains. The cavities comprise an architecture that encourages the ingrowth of vascular tissue in vivo, as indicated by the blood vessels 79 formed throughout the cavities. Because of the vascularization within the cavities, solutes 73 (for example, oxygen, glucose and other analytes) pass through the first domain with relative ease, and/or the diffusion distance (namely, distance that the glucose diffuses) is reduced.

Architecture of the First Domain

In some embodiments, the first domain of the biointerface membrane includes an architecture that supports tissue ingrowth, disrupts contractile forces typically found in a foreign body response, encourages vascularity within the membrane, and disrupts the formation of a barrier cell layer. In some alternative embodiments, the first domain of the biointerface membrane includes an architecture that creates a fluid-filled space surrounding an implanted device, which allows the passage of the analyte, but protects sensitive portions of the device from substantial fibrous tissue ingrowth and associated forces.

In general, the first domain, also referred to as the cell disruptive domain, comprises an open-celled configuration comprising interconnected cavities and solid portions. The distribution of the solid portion and cavities of the first domain preferably includes a substantially co-continuous solid domain and includes more than one cavity in three dimensions substantially throughout the entirety of the first domain. However, some short-term embodiments may not require co-continuity of the cavities. Generally, cells can enter into the cavities; however, they cannot travel through or wholly exist within the solid portions. The cavities permit most substances to pass through, including, for example, cells and molecules. One example of a suitable material is expanded polytetrafluoraethylene (ePTFE).

Figure 4B:
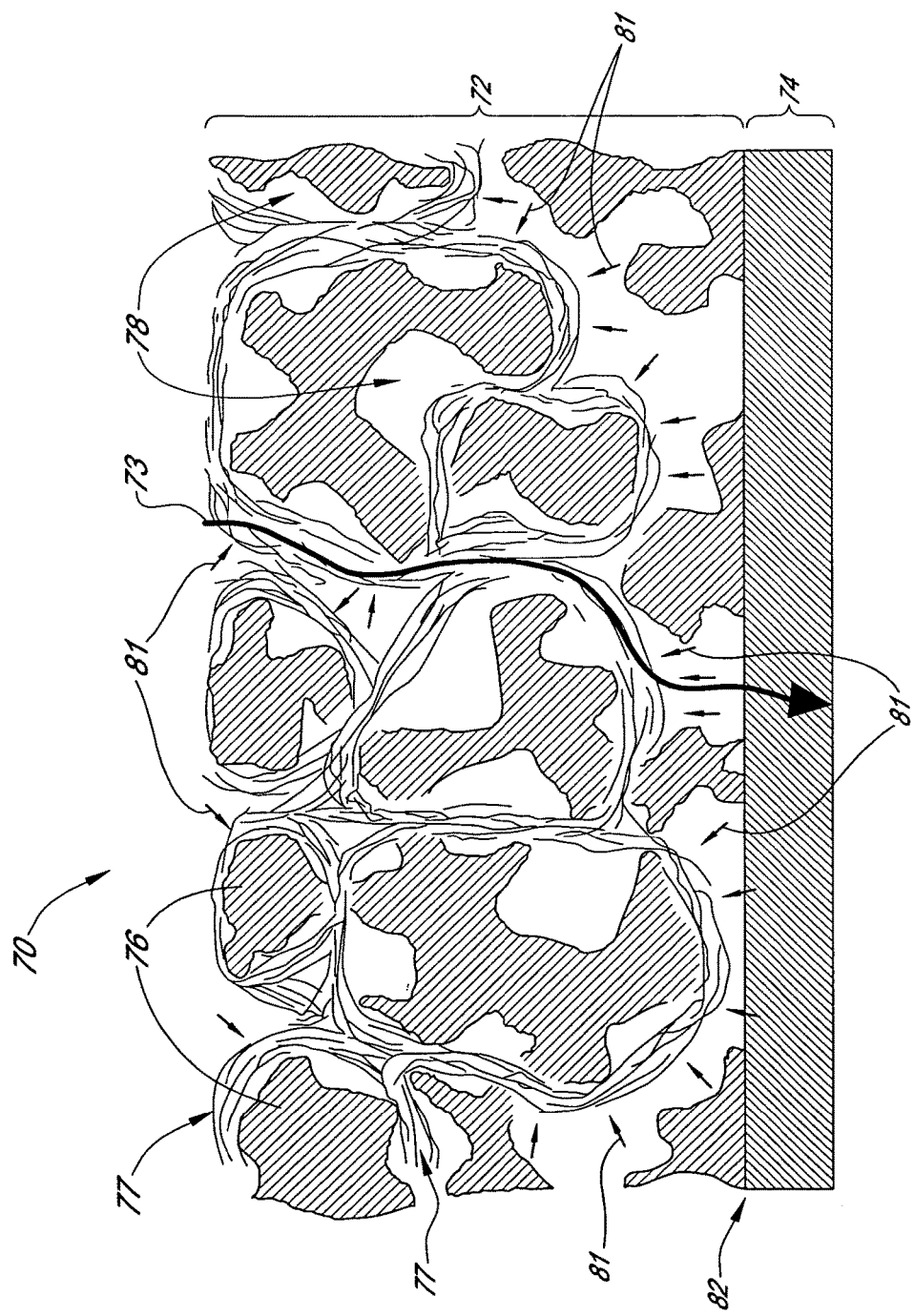
FIG. 4B is a cross-sectional schematic view of the membrane of FIG. 2A showing contractile forces caused by the fibrous tissue of the FBR.

Reference is now made to FIG. 4B, which is an illustration of the membrane of FIG. 4A, showing contractile forces caused by the fibrous tissue in the long term (e.g., after about 3 weeks), for example, from the fibroblasts and fibrous matrix, of the FBR. Specifically, the architecture of the first domain, including the cavity interconnectivity and multiple-cavity depth, (namely, two or more cavities in three dimensions throughout a substantial portion of the first domain) can affect the tissue contracture that typically occurs around a foreign body.

The architecture of the first domain of the biointerface membrane, including the interconnected cavities and solid portion, is advantageous because the contractile forces caused by the downward tissue contracture that can otherwise cause cells to flatten against the device and occlude the transport of analytes, is instead translated to, disrupted by, and/or counteracted by the forces 81 that contract around the solid portions 76 (for example, throughout the interconnected cavities 78) away from the device. That is, the architecture of the solid portions 76 and cavities 78 of the first domain cause contractile forces 81 to disperse away from the interface between the first domain 72 and second domain 74. Without the organized contracture of fibrous tissue toward the tissue-device interface 82 typically found in a FBC (FIG. 1), macrophages and foreign body giant cells do not form a substantial monolayer of cohesive cells (namely, a barrier cell layer) and therefore the transport of molecules across the second domain and/or membrane is not blocked, as indicated by free transport of analyte 73 through the first and second domains in FIGS. 2A and 2B.

Various methods are suitable for use in manufacturing the first domain in order to create an architecture with preferred dimensions and overall structure. The first domain can be manufactured by forming particles, for example, sugar granules, salt granules, and other natural or synthetic uniform or non-uniform particles, in a mold, wherein the particles have shapes and sizes substantially corresponding to the desired cavity dimensions, such as described in more detail below. In some methods, the particles are made to coalesce to provide the desired interconnectivity between the cavities. The desired material for the solid portion can be introduced into the mold using methods common in the art of polymer processing, for example, injecting, pressing, vacuuming, vapor depositing, pouring, and the like. After the solid portion material is cured or solidified, the coalesced particles are then dissolved, melted, etched, or otherwise removed, leaving interconnecting cavities within the solid portion. In such embodiments, sieving can be used to determine the dimensions of the particles, which substantially correspond to the dimensions of resulting cavities. In sieving, also referred to as screening, the particles are added to the sieve and then shaken to produce overs and unders. The overs are the particles that remain on the screen and the unders are the particles that pass through the screen. Other methods and apparatus known in the art are also suitable for use in determining particle size, for example, air classifiers, which apply opposing air flows and centrifugal forces to separate particles having sizes down to 2 µm, can be used to determine particle size when particles are smaller than 100 µm.

In one embodiment, the cavity size of the cavities 78 of the first domain is substantially defined by the particle size(s) used in creating the cavities. In some embodiments, the particles used to form the cavities can be substantially spherical, thus the dimensions below describe a diameter of the particle and/or a diameter of the cavity. In some alternative embodiments, the particles used to form the cavities can be non-spherical (for example, rectangular, square, diamond, or other geometric or non-geometric shapes), thus the dimensions below describe one dimension (for example, shortest, average, or longest) of the particle and/or cavity.

In some embodiments, a variety of different particle sizes can be used in the manufacture of the first domain. In some embodiments, the dimensions of the particles can be somewhat smaller or larger than the dimensions of the resulting cavities, due to dissolution or other precipitation that can occur during the manufacturing process.

Although one method of manufacturing porous domains is described above, a variety of methods known to one of ordinary skill in the art can be employed to create the structures of preferred embodiments, see section entitled, "Formation of the Biointerface onto the Sensor," below. For example, molds can be used in the place of the particles described above, such as coral, self-assembly beads, etched or broken silicon pieces, glass frit pieces, and the like. The dimensions of the mold can define the cavity sizes, which can be determined by measuring the cavities of a model final product, and/or by other measuring techniques known in the art, for example, by a bubble point test. In U.S. Pat. No. 3,929,971, Roy discloses a method of making a synthetic membrane having a porous microstructure by converting calcium carbonate coral materials to hydroxyapatite while at the same time retaining the unique microstructure of the coral material.

Other methods of forming a three-dimensional first domain can be used, for example holographic lithography, stereolithography, and the like, wherein cavity sizes are defined and precisely formed by the lithographic or other such process to form a lattice of unit cells, as described in co-pending U.S. patent application Ser. No. 11/055,779, entitled "Macro-Micro Architecture for Biointerface Membrane," which is incorporated herein by reference in its entirety and as described by Pekkarinen et al. in U.S. Pat. No. 6,520,997, which discloses a photolithographic process for creating a porous membrane.

The first domain 72 can be defined using alternative methods. In an alternative preferred embodiment, fibrous non-woven or woven materials, or other such materials, such as electrospun, felted, velvet, scattered, or aggregate materials, are manufactured by forming the solid portions without particularly defining the cavities therebetween. Accordingly, in these alternative embodiments, structural elements that provide the three-dimensional conformation can include fibers, strands, globules, cones, and/or rods of amorphous or uniform geometry. These elements are hereinafter referred to as "strands." The solid portion of the first domain can include a plurality of strands, which generally define apertures formed by a frame of the interconnected strands. The apertures of the material form a framework of interconnected cavities. Formed in this manner, the first domain is defined by a cavity size of about 0.6 to about 1 mm in at least one dimension.

Referring to the dimensions and architecture of the first domain 72, the porous biointerface membranes can be loosely categorized into at least two groups: those having a micro-architecture and those having a macro-architecture.

FIGS. 4A and 4B illustrate one preferred embodiment wherein the biointerface membrane includes a macro-architecture as defined herein. In general, the cavity size of a macro-architecture provides a configuration and overall thickness that encourages vascular tissue ingrowth and disrupts tissue contracture that is believed to cause barrier cell formation in the long term in vivo (as indicated by the blood vessels 79 formed throughout the cavities), while providing a long-term, robust structure. Referring to the macro-architecture, a substantial number of the cavities 78, defined using any of the methods described above, are greater than or equal to about 20 μm in one dimension. In some other embodiments, a substantial number of the cavities are greater than or equal to about 30, 40, 50, 60, 70, 80, 90, 100, 120, 180, 160, 180, 200, 280, 280, 320, 360, 400, 500, 600, 700 μm, and preferably less than about 1 mm in one dimension.

The biointerface membrane can also be formed with a micro-architecture as defined herein. Generally, at least some of the cavities of a micro-architecture have a sufficient size and structure to allow inflammatory cells to partially or completely enter into the cavities. However, in contrast to the macro-architecture, the micro-architecture does not allow extensive ingrowth of vascular and connective tissues within the cavities. Therefore, in some embodiments, the micro-architecture of preferred embodiments is defined by the actual size of the cavity, wherein the cavities are formed from a mold, for example, such as described in more detail above. However, in the context of the micro-architecture it is preferable that the majority of the mold dimensions, whether particles, beads, crystals, coral, self-assembly beads, etched or broken silicon pieces, glass frit pieces, or other mold elements that form cavities, are less than about 20 μm in at least one dimension.

In some alternative embodiments, wherein the biointerface membrane is formed from a substantially fibrous material, the micro-architecture is defined by a strand size of less than about 6 μm in all but the longest dimension, and a sufficient number of cavities are provided of a size and structure to allow inflammatory cells, for example, macrophages, to completely enter through the apertures that define the cavities, without extensive ingrowth of vascular and connective tissues.

In certain embodiments, the micro-architecture is characterized, or defined, by standard pore size tests, such as the bubble point test. The micro-architecture is selected with a nominal pore size of from about 0.6 μm to about 20 μm. In some embodiments, the nominal pore size from about 1, 2, 3, 4, 5, 6, 7, 8, or 9 μm to about 10, 11, 12, 13, 14, 15, 16, 17, 18, or 19 μm. It has been found that a porous polymer membrane having an average nominal pore size of about 0.6 to about 20 μm functions satisfactorily in creating a vascular bed within the micro-architecture at the device-tissue interface. The term "nominal pore size" in the context of the micro-architecture in certain embodiments is derived from methods of analysis common to membrane, such as the ability of the membrane to filter particles of a particular size, or the resistance of the membrane to the flow of fluids. Because of the amorphous, random, and irregular nature of most of these commercially available membranes, the "nominal pore size" designation may not actually indicate the size or shape of the apertures and cavities, which in reality have a high degree of variability. Accordingly, as used herein with reference to the micro-architecture, the term "nominal pore size" is a manufacturer's convention used to identify a particular membrane of a particular commercial source which has a certain bubble point; as used herein, the term "pore" does not describe the size of the cavities of the material in the preferred embodiments. The bubble point measurement is described in Pharmaceutical Technology, May 1983, pp. 76 to 82.

The optimum dimensions, architecture (for example, micro-architecture or macro-architecture), and overall structural integrity of the membrane can be adjusted according to the parameters of the device that it supports. For example, if the membrane is employed with a glucose-measuring device, the mechanical requirements of the membrane can be greater for devices having greater overall weight and surface area when compared to those that are relatively smaller.

In some embodiments, improved vascular tissue ingrowth in the long term is observed when the first domain has a thickness that accommodates a depth of at least two cavities throughout a substantial portion of the thickness. Improved vascularization results at least in part from multi-layered interconnectivity of the cavities, such as in the preferred embodiments, as compared to a surface topography such as seen in the prior art, for example, wherein the first domain has a depth of only one cavity throughout a substantial portion thereof. The multi-layered interconnectivity of the cavities enables vascularized tissue to grow into various layers of cavities in a manner that provides mechanical anchoring of the device with the surrounding tissue. Such anchoring resists movement that can occur in vivo, which results in reduced sheer stress and scar tissue formation. The optimum depth or number of cavities can vary depending upon the parameters of the device that it supports. For example, if the membrane is employed with a glucose-measuring device, the anchoring that is required of the membrane is greater for devices having greater overall weight and surface area as compared to those that are relatively smaller.

The thickness of the first domain can be optimized for decreased time-to-vascularize in vivo, that is, vascular tissue ingrowth can occur somewhat faster with a membrane that has a thin first domain as compared to a membrane that has a relatively thicker first domain. Decreased time-to-vascularize results in faster stabilization and functionality of the biointerface in vivo. For example, in a subcutaneous implantable glucose device, consistent and increasing functionality of the device is at least in part a function of consistent and stable glucose transport across the biointerface membrane, which is at least in part a function of the vascularization thereof. Thus, quicker start-up time and/or shortened time lag (as when, for example, the diffusion path of the glucose through the membrane is reduced) can be achieved by decreasing the thickness of the first domain.

The thickness of the first domain is typically from about 20 μm to about 2000 μm, preferably from about 50, 60, 70, 80, 90, or 100 μm to about 800, 900, 1000, 1100, 1200, 1300, 1400, 1500, 1600, 1700, 1800, or 1900 μm, and most preferably from about 150, 200, 250, 300, 350, or 400 μm to about 450, 500, 550, 600, 650, 700, or 750 μm. However, in some alternative embodiments a thinner or thicker cell disruptive domain (first domain) can be desired.

The solid portion preferably includes one or more materials such as silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, polysulfones and block copolymers thereof including, for example, diblock, tri-block, alternating, random and graft copolymers. In some embodiments, the material selected for the first domain is an elastomeric material, for example, silicone, which is able to absorb stresses that can occur in vivo, such that sheer and other environmental forces are significantly minimized at the second domain. The solid portion can comprises a silicone composition with a hydrophile such as Polyethylene Glycol (PEG) covalently incorporated or grafted therein, such as described in co-pending U.S. patent application Ser. No. 10/695,676, filed Oct. 28, 2003, and entitled, "SILICONE COMPOSITION FOR BIOCOMPATIBLE MEMBRANE," which is incorporated herein by reference in its entirety.

One preferred material that can be used to form the solid portion of the biointerface matrix is a material that allows the passage of the analyte (e.g., glucose) there through. For example, the biointerface matrix may be formed from a silicone polymer/hydrophobic-hydrophilic polymer blend. In one embodiment, The hydrophobic-hydrophilic polymer for use in the blend may be any suitable hydrophobic-hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044, which are incorporated herein by reference). In one embodiment, the hydrophobic-hydrophilic polymer is a copolymer of poly (ethylene oxide) (PEO) and poly(propylene oxide) (PPO). Suitable such polymers include, but are not limited to, PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof. In some embodiments, the copolymers may be optionally substituted with hydroxy substituents. Commercially available examples of PEO and PPO copolymers include the PLURONIC® brand of polymers available from BASF®. In one embodiment, PLURONIC® F-127 is used. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The silicone polymer for use in the silicone/hydrophobic-hydrophilic polymer blend may be any suitable silicone polymer. In some embodiments, the silicone polymer is a liquid silicone rubber that may be vulcanized using a metal- (e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers may be used. For example, commercially available silicone polymer precursor compositions may be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components may be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

Silicone polymer/hydrophobic-hydrophilic polymer blends are described in more detail in U.S. patent application Ser. No. 11/404,417, entitled "SILICONE BASED MEMBRANES FOR USE IN IMPLANTABLE GLUCOSE SENSORS," filed on Apr. 14, 2006.

Additionally, elastomeric materials with a memory of the original configuration can withstand greater stresses without affecting the configuration, and thus the function, of the device.

In some embodiments, the first domain can include a macro-architecture and a micro-architecture located within at least a portion of the macro-architecture, such as is described in co-pending U.S. patent application Ser. No. 11/055,779, entitled, "BIOINTERFACE WITH MACRO- AND MICRO-ARCHITECTURE." For example, the macro-architecture includes a porous structure with interconnected cavities such as described with reference to the solid portion of the first domain, wherein at least some portion of the cavities of the first domain are filled with the micro-architecture that includes a fibrous or other fine structured material that aids in preventing formation of a barrier cell layer, for example in pockets in the bottom of the cavities of the macro-architecture adjacent to the implantable device.

In certain embodiments, other non-resorbable implant materials can be used in forming the first domain, including but not limited to, metals, ceramics, cellulose, hydrogel polymers, poly(2-hydroxyethyl methacrylate, pHEMA), hydroxyethyl methacrylate, (HEMA), polyacrylonitrile-polyvinyl chloride (PAN-PVC), high density polyethylene, acrylic copolymers, nylon, polyvinyl difluoride, polyanhydrides, poly(l-lysine), poly(L-lactic acid), hydroxyethylmetharcrylate, hydoxyapaptite, alumina, zirconia, carbon fiber, aluminum, calcium phosphate (and its chemical variants), titanium, titanium alloy, nintinol, stainless steel, and CoCr alloy.

Architecture of the Second Domain

FIGS. 4A and 4B, illustrate the optional second domain of the membrane. The second domain is impermeable to cells or cell processes, and is composed of a biostable material. In one exemplary embodiment, the second domain is comprised of polyurethane and a hydrophilic polymer, such as is described in U.S. Pat. No. 6,862,465 to Shults et al., which is incorporated herein by reference in its entirety. Alternatively, the outermost layer of the sensing membrane 32 can function as a cell impermeable domain and therefore a second domain may not be a discrete component of the biointerface membrane.

In general, the materials preferred for the second domain prevent or hinder cell entry or contact with device elements underlying the membrane and prevent or hinder the adherence of cells, thereby further discouraging formation of a barrier cell layer. Additionally, because of the resistance of the materials to barrier cell layer formation, membranes prepared therefrom are robust long-term in vivo.

The thickness of the cell impermeable biomaterial of the second domain (also referred to as a cell impermeable domain) is typically about 1 µm or more, preferably from about 1, 5, 10, 15, 20, 25, 30, 35, 40, 45, or 50, 55, 60, 65, 70, 75, 80, 85, 90, 95, 100, 110, 120, 130, 140, 150, 160, 170, 180, 190, or 200 µm to about 500, 600, 700, 800, 900, or 1000 µm. In some embodiments, thicker or thinner cell impermeable domains can be desired. Alternatively, the function of the cell impermeable domain is accomplished by the implantable device, or a portion of the implantable device, which may or may not include a distinct domain or layer.

The characteristics of the cell impermeable membrane prevent or hinder cells from entering the membrane, but permit or facilitate transport of the analyte of interest or a substance indicative of the concentration or presence of the analyte. Additionally the second domain, similar to the first domain, is preferably constructed of a biodurable material (for example, a material durable for a period of several years in vivo) that is impermeable to host cells, for example, macrophages, such as described above.

In embodiments wherein the biointerface membrane is employed in an implantable glucose-measuring device, the biointerface membrane is permeable to oxygen and glucose or a substance indicative of the concentration of glucose. In embodiments wherein the membrane is employed in a drug delivery device or other device for delivering a substance to the body, the cell impermeable membrane is permeable to the drug or other substance dispensed from the device. In embodiments wherein the membrane is employed for cell transplantation, the membrane is semi-permeable, for example, impermeable to immune cells and soluble factors responsible for rejecting transplanted tissue, but permeable to the ingress of glucose and oxygen for the purpose of sustaining the transplanted tissue; additionally, the second domain is permeable to the egress of the gene product of interest (for example, insulin).

The cell disruptive (first) domain and the cell impermeable (second) domain can be secured to each other by any suitable method as is known in the art. For example, the cell impermeable domain can simply be layered or cast upon the porous cell disruptive domain so as to form a mechanical attachment. Alternatively, chemical and/or mechanical attachment methods can be suitable for use. Chemical attachment methods can include adhesives, glues, lamination, and/or wherein a thermal bond is formed through the application of heat and pressure, and the like. Suitable adhesives are those capable of forming a bond between the materials that make up both the barrier cell disruptive domain and the cell impermeable domain, and include liquid and/or film applied adhesives. An appropriate material can be designed that can be used for preparing both domains such that the composite is prepared in one step, thereby forming a unitary structure. For example, when the cell disruptive domain and the cell impermeable domain comprise silicone, the materials can be designed so that they can be covalently cured to one another. However, in some embodiments wherein the second domain comprises a part of the implantable device, it can be attached to or simply lie adjacent to the first domain.

In some embodiments wherein an adhesive is employed, the adhesive can comprise a biocompatible material. However, in some embodiments adhesives not generally considered to have a high degree of biocompatibility can also be employed. Adhesives with varying degrees of biocompatibility suitable for use include acrylates, for example, cyanoacrylates, epoxies, methacrylates, polyurethanes, and other polymers, resins, RTV silicone, and crosslinking agents as are known in the art. In some embodiments, a layer of woven or non-woven material (such as ePTFE) is cured to the first domain after which the material is bonded to the second domain, which allows a good adhesive interface between the first and second domains using a biomaterial known to respond well at the tissue-device interface, for example.

Bioactive Agents

In some alternative embodiment, the biointerface membranes include a bioactive agent, which is incorporated into at least one of the first and second domains 72, 74 of the biointerface membrane, or which is incorporated into the device (e.g., sensing membrane 32) and adapted to diffuse through the first and/or second domains, in order to modify the tissue response of the host to the membrane. The architectures of the first and second domains have been shown to create a fluid pocket, support vascularized tissue ingrowth, to interfere with and resist barrier cell layer formation, and to facilitate the transport of analytes across the membrane. However, the bioactive agent can further enhance formation of a fluid pocket, alter or enhance vascularized tissue ingrowth, resistance to barrier cell layer formation, and thereby facilitate the passage of analytes 73 across the device-tissue interface 82.

In embodiments wherein the biointerface includes a bioactive agent, the bioactive agent is incorporated into at least one of the first and second domains of the biointerface membrane, or into the device and adapted to diffuse through the first and/or second domains, in order to modify the tissue response of the host to the membrane. In general, the architectures of the first and second domains support vascularized tissue growth in or around the biointerface membrane, interfere with and resist barrier cell layer formation, and/or allow the transport of analytes across the membrane. However, certain outside influences, for example, faulty surgical techniques, acute or chronic movement of the implant, or other surgery-, host-, and/or implantation site-related conditions, can create acute and/or chronic inflammation at the implant site. When this occurs, the biointerface membrane architecture alone may not be sufficient to overcome the acute and/or chronic inflammation. Alternatively, the membrane architecture can benefit from additional mechanisms that aid in reducing this acute and/or chronic inflammation that can produce a barrier cell layer and/or a fibrotic capsule surrounding the implant, resulting in compromised solute transport through the membrane.

In general, the inflammatory response to biomaterial implants can be divided into two phases. The first phase consists of mobilization of mast cells and then infiltration of predominantly polymorphonuclear (PMN) cells. This phase is termed the acute inflammatory phase. Over the course of days to weeks, chronic cell types that comprise the second phase of inflammation replace the PMNs. Macrophage and lymphocyte cells predominate during this phase. While not wishing to be bound by any particular theory, it is believed that short-term stimulation of vascularization, or short-term inhibition of scar formation or barrier cell layer formation, provides protection from scar tissue formation, thereby providing a stable platform for sustained maintenance of the altered foreign body response, for example.

Accordingly, bioactive intervention can modify the foreign body response in the early weeks of foreign body capsule formation and alter the long-term behavior of the foreign body capsule. Additionally, it is believed that in some circumstances the biointerface membranes of the preferred embodiments can benefit from bioactive intervention to overcome sensitivity of the membrane to implant procedure, motion of the implant, or other factors, which are known to otherwise cause inflammation, scar formation, and hinder device function in vivo.

In general, bioactive agents that are believed to modify tissue response include anti-inflammatory agents, anti-infective agents, anesthetics, inflammatory agents, growth factors, angiogenic (growth) factors, adjuvants, immunosuppressive agents, antiplatelet agents, anticoagulants, ACE inhibitors, cytotoxic agents, anti-barrier cell compounds, vascularization compounds, anti-sense molecules, and the like. In some embodiments, preferred bioactive agents include S1P (Sphingosine-1-phosphate), Monobutyrin, Cyclosporin A, Anti-thrombospondin-2, Rapamycin (and its derivatives), and Dexamethasone. However, other bioactive agents, biological materials (for example, proteins), or even non-bioactive substances can incorporated into the membranes of preferred embodiments.

Bioactive agents suitable for use in the preferred embodiments are loosely organized into two groups: anti-barrier cell agents and vascularization agents. These designations reflect functions that are believed to provide short-term solute transport through the biointerface membrane, and additionally extend the life of a healthy vascular bed and hence solute transport through the biointerface membrane long term in vivo. However, not all bioactive agents can be clearly categorized into one or other of the above groups; rather, bioactive agents generally comprise one or more varying mechanisms for modifying tissue response and can be generally categorized into one or both of the above-cited categories.

Anti-Barrier Cell Agents

Generally, anti-barrier cell agents include compounds exhibiting affects on macrophages and foreign body giant cells (FBGCs). It is believed that anti-barrier cell agents prevent closure of the barrier to solute transport presented by macrophages and FBGCs at the device-tissue interface during FBC maturation.

Anti-barrier cell agents generally include mechanisms that inhibit foreign body giant cells and/or occlusive cell layers. For example, Super Oxide Dismutase (SOD) Mimetic, which utilizes a manganese catalytic center within a porphyrin like molecule to mimic native SOD and effectively remove superoxide for long periods, thereby inhibiting FBGC formation at the surfaces of biomaterials in vivo, is incorporated into a biointerface membrane of a preferred embodiment.

Anti-barrier cell agents can include anti-inflammatory and/or immunosuppressive mechanisms that affect early FBC formation. Cyclosporine, which stimulates very high levels of neovascularization around biomaterials, can be incorporated into a biointerface membrane of a preferred embodiment (see U.S. Pat. No. 5,569,462 to Martinson et al.). Alternatively, Dexamethasone, which abates the intensity of the FBC response at the tissue-device interface, can be incorporated into a biointerface membrane of a preferred embodiment. Alternatively, Rapamycin, which is a potent specific inhibitor of some macrophage inflammatory functions, can be incorporated into a biointerface membrane of a preferred embodiment.

Other suitable medicaments, pharmaceutical compositions, therapeutic agents, or other desirable substances can be incorporated into the membranes of preferred embodiments, including, but not limited to, anti-inflammatory agents, anti-infective agents, necrosing agents, and anesthetics.

Generally, anti-inflammatory agents reduce acute and/or chronic inflammation adjacent to the implant, in order to decrease the formation of a FBC capsule to reduce or prevent barrier cell layer formation. Suitable anti-inflammatory agents include but are not limited to, for example, nonsteroidal anti-inflammatory drugs (NSAIDs) such as acetometaphen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), Interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, and dexamethasone.

Generally, immunosuppressive and/or immunomodulatory agents interfere directly with several key mechanisms necessary for involvement of different cellular elements in the inflammatory response. Suitable immunosuppressive and/or immunomodulatory agents include anti-proliferative, cell-cycle inhibitors, (for example, paclitaxol (e.g., Sirolimus), cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), *E. coli* heat-labile enterotoxin, and advanced coatings.

Generally, anti-infective agents are substances capable of acting against infection by inhibiting the spread of an infectious agent or by killing the infectious agent outright, which can serve to reduce immuno-response without inflammatory response at the implant site. Anti-infective agents include, but are not limited to, anthelmintics (mebendazole), antibiotics including aminoclycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

Generally, necrosing agents are any drug that causes tissue necrosis or cell death. Necrosing agents include cisplatin, BCNU, taxol or taxol derivatives, and the like.

Vascularization Agents

Generally, vascularization agents include substances with direct or indirect angiogenic properties. In some cases, vascularization agents may additionally affect formation of barrier cells in vivo. By indirect angiogenesis, it is meant that the angiogenesis can be mediated through inflammatory or immune stimulatory pathways. It is not fully known how agents that induce local vascularization indirectly inhibit barrier-cell formation; however it is believed that some barrier-cell effects can result indirectly from the effects of vascularization agents.

Vascularization agents include mechanisms that promote neovascularization around the membrane and/or minimize periods of ischemia by increasing vascularization close to the tissue-device interface. Sphingosine-1-Phosphate (S1P), which is a phospholipid possessing potent angiogenic activity, is incorporated into a biointerface membrane of a preferred embodiment. Monobutyrin, which is a potent vasodilator and angiogenic lipid product of adipocytes, is incorporated into a biointerface membrane of a preferred embodiment. In another embodiment, an anti-sense molecule (for example, thrombospondin-2 anti-sense), which increases vascularization, is incorporated into a biointerface membrane.

Vascularization agents can include mechanisms that promote inflammation, which is believed to cause accelerated neovascularization in vivo. In one embodiment, a xenogenic carrier, for example, bovine collagen, which by its foreign nature invokes an immune response, stimulates neovascularization, and is incorporated into a biointerface membrane of the preferred embodiments. In another embodiment, Lipopolysaccharide, which is a potent immunostimulant, is incorporated into a biointerface membrane. In another embodiment, a protein, for example, a bone morphogenetic protein (BMP), which is known to modulate bone healing in tissue, is incorporated into a biointerface membrane of a preferred embodiment.

Generally, angiogenic agents are substances capable of stimulating neovascularization, which can accelerate and sustain the development of a vascularized tissue bed at the tissue-device interface. Angiogenic agents include, but are not limited to, copper ions, iron ions, tridodecylmethylammonium chloride, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Copper Sulphate, Estradiol, prostaglandins, cox inhibitors, endothelial cell binding agents (for example, decorin or vimentin), glenipin, hydrogen peroxide, nicotine, and Growth Hormone.

Generally, pro-inflammatory agents are substances capable of stimulating an immune response in host tissue, which can accelerate or sustain formation of a mature vascularized tissue bed. For example, pro-inflammatory agents are generally irritants or other substances that induce chronic inflammation and chronic granular response at the implantation-site. While not wishing to be bound by theory, it is believed that formation of high tissue granulation induces blood vessels, which supply an adequate or rich supply of analytes to the device-tissue interface. Pro-inflammatory agents include, but are not limited to, xenogenic carriers, Lipopolysaccharides, *S. aureus* peptidoglycan, and proteins.

Other substances that can be incorporated into membranes of preferred embodiments include various pharmacological agents, excipients, and other substances well known in the art of pharmaceutical formulations.

U.S. Publication No. 2005/0031689 A1 to Shults et al. discloses a variety of systems and methods by which the bioactive agent can be incorporated into the biointerface membranes and/or implantable device. Although the bioactive agent is preferably incorporated into the biointerface membrane and/or implantable device, in some embodiments the bioactive agent can be administered concurrently with, prior to, or after implantation of the device systemically, for example, by oral administration, or locally, for example, by subcutaneous injection near the implantation site. A combination of bioactive agent incorporated in the biointerface membrane and bioactive agent administration locally and/or systemically can be preferred in certain embodiments.

Generally, numerous variables can affect the pharmacokinetics of bioactive agent release. The bioactive agents of the preferred embodiments can be optimized for short- and/or long-term release. In some embodiments, the bioactive agents of the preferred embodiments are designed to aid or overcome factors associated with short-term effects (for example, acute inflammation) of the foreign body response, which can begin as early as the time of implantation and extend up to about one month after implantation. In some embodiments, the bioactive agents of the preferred embodiments are designed to aid or overcome factors associated with long-term effects, for example, chronic inflammation, barrier cell layer formation, or build-up of fibrotic tissue of the foreign body response, which can begin as early as about one week after implantation and extend for the life of the implant, for example, months to years. In some embodiments, the bioactive agents of the preferred embodiments combine short- and long-term release to exploit the benefits of both. Published U.S. Publication No. 2005/0031689 A1 to Shults et al. discloses a variety of systems and methods for release of the bioactive agents.

The amount of loading of the bioactive agent into the biointerface membrane can depend upon several factors. For example, the bioactive agent dosage and duration can vary with the intended use of the biointerface membrane, for example, cell transplantation, analyte measuring-device, and the like; differences among hosts in the effective dose of bioactive agent; location and methods of loading the bioactive agent; and release rates associated with bioactive agents and optionally their carrier matrix. Therefore, one skilled in the art will appreciate the variability in the levels of loading the bioactive agent, for the reasons described above. U.S. Publication No. 2005/0031689 A1 to Shults et al. discloses a variety of systems and methods for loading of the bioactive agents.

Biointerface Membrane Formation onto the Sensor

Due to the small dimension(s) of the sensor (sensing mechanism) of the preferred embodiments, some conventional methods of porous membrane formation and/or porous membrane adhesion are inappropriate for the formation of the biointerface membrane onto the sensor as described herein. Accordingly, the following embodiments exemplify systems and methods for forming and/or adhering a biointerface membrane onto a small structured sensor as defined herein. For example, the biointerface membrane of the preferred embodiments can be formed onto the sensor using techniques such as electrospinning, molding, weaving, direct-writing, lyophilizing, wrapping, and the like.

Although FIGS. 5 to 9 describe systems and methods for the formation of porous biointerface membranes, including interconnected cavities and solid portion(s). In some embodiments, a cell impermeable (second domain) can additionally be formed using known thin film techniques, such as dip coating, spray coating, spin coating, tampo printing, and the like, prior to formation of the interconnected cavities and solid portion(s). Alternatively, the porous biointerface membrane (e.g., first domain) can be formed directly onto the sensing membrane.

Figure 5:
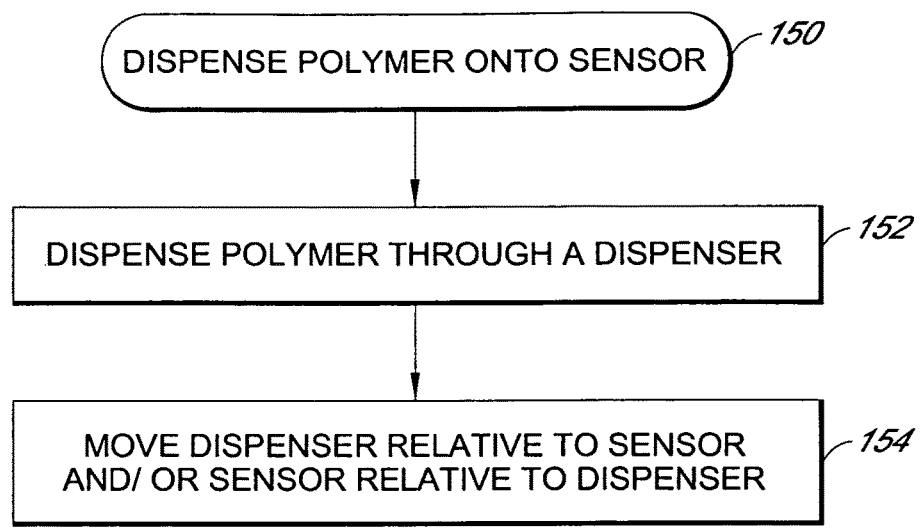
FIG. 5 is a flow chart that illustrates the process of forming a biointerface-coated small structured sensor in one embodiment.

FIG. 5 is a flow chart that illustrates the process 150 of forming a biointerface-coated small structured sensor in one embodiment. In this embodiment, the biointerface membrane includes woven or non-woven fibers formed directly onto the sensor. Generally, fibers can be deposited onto the sensor using methods suitable for formation of woven- or non-woven fibrous materials. In some embodiments, the biointerface membrane is electrospun directly onto the sensor; electrospinning advantageously allows the biointerface membranes to be made with small consistent fiber diameters that are fused at the nodes and are without aggregation.

In some embodiments, the biointerface membrane is directly written onto the sensor; direct-writing can advantageously allow uniform deposition of stored patterns (e.g., in a computer system) for providing consistent and reproducible architectures. In these embodiments, a curing step is included either during or after the writing step to solidify the material being written (e.g., heat, UV curing, radiation, etc.). Direct-writing is described in more detail, below.

At block 152, one or more dispensers dispense a polymeric material used to form the fibers. A variety of polymeric materials are contemplated for use with the preferred embodiments, including one or more of silicone, polytetrafluoroethylene, expanded polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polyvinyl alcohol (PVA), polybutylene terephthalate (PBT), polymethylmethacrylate (PMMA), polyether ether ketone (PEEK), polyamides, polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

The coating process can be performed in a vacuum or in a gaseous medium, which environment may affect the architecture of the biointerface membrane as is appreciated by one skilled in the art.

In embodiments wherein the biointerface is electrospun onto the sensor, the dispenser dispenses a charged liquefied polymer within an electric field, to thereby form a jet of polymer fibers, for example, such as described in PCT International Publication No. WO 2005/032400 A1.

In embodiments wherein the biointerface is directly-written onto the sensor, a dispenser dispenses a polymer solution using a nozzle with a valve, or the like, for example as described in U.S. Publication No. 2004/0253365 A1. In general, a variety of nozzles and/or dispensers can be used to dispense a polymeric material to form the woven or non-woven fibers of the biointerface membrane.

In general, a direct-write patterning system is suitable for either fine-pattern micro-dispensing and/or fine-focused laser-beam writing over flat or conformal surfaces to create exact replicas of a preferred biointerface structure. In certain embodiments, the biointerface materials described herein may be deposited using these integrated tool technologies for the direct-write deposition and laser micromachining of a wide variety of biointerface architectures described herein. Additionally, the direct-write patterning system can provide the capability for concurrent detection and imaging methods during additive and subtractive processes.

In another aspect, alternative embodiments of the direct-writing deposition technique utilize a tool in which constituent materials may be dispensed through multiple, discrete dispensing heads. In yet another alternative embodiment, the biointerface structure is directly-written onto a removable substrate, after which the substrate is removed and the biointerface applied to the sensor (e.g., wrapped around the sensor or the sensor is inserted into the biointerface).

At block 154, the dispenser(s) is moved relative to the sensor and/or the sensor is moved relative to the dispenser(s) so as to coat the sensor with the fibers. In embodiments wherein the biointerface membrane is electrospun onto the sensor, the dispenser(s) can change the direction and/or magnitude of the electric field during motion in order to effect the orientation of the polymer fibers on the sensor. Additionally, the path of the dispenser is preferably selected so as to coat the portions of or the entire object. In one exemplary embodiment, wherein it is desirable for the biointerface membrane to substantially circumscribe the sensor (e.g., a substantially cylindrical shape), such as illustrated in FIG. 2A, the dispenser can be moved along a helix path, a circular path, a zigzag path, or the like. Additionally, the dispenser can move rotationally and/or translationally relative to the sensor. The number of sweeps is preferably selected according to the desired architecture of the biointerface membrane. Additionally, the density of the fibers and/or the type of liquefied polymer can be changed from one sweep to the other to thereby control the architecture of the membrane.

In embodiments wherein the biointerface membrane is directly written onto the sensor, the dispenser is programmed to write a pattern that creates the desired membrane architecture, including the interconnected cavities and solid portion(s). Namely, the dispenser is programmed to move in the x, y, and optionally z direction in order to create the desired membrane architecture. See, for example, U.S. Publication No. 2004/0253365 A1 cited above.

Although the preferred embodiments described moving the dispenser(s) relative to the sensor, alternatively, the dispenser can remain stationary and the sensor moved, as is appreciated by one skilled in the art.

In some embodiments, the sensor is moved in a rotational or translational motion, which can be performed in combination with, or instead of, movement of the dispenser. In this step, the sensor is moved so as to ensure coating throughout the entirety of the biointerface region (or a portion thereof). In one exemplary embodiment, wherein a substantially circumscribing biointerface membrane is desired (e.g., for a substantially cylindrically shaped sensing sensor) such as illustrated in FIG. 2A, the sensor can be rotated so to aid in coating the entire circumference of the sensor. In another exemplary embodiment, wherein a substantially planar biointerface membrane is desired (e.g., for a substantially planar sensor), the sensor can be translated so as to aid in coating the desired planar surface area.

Figure 6:
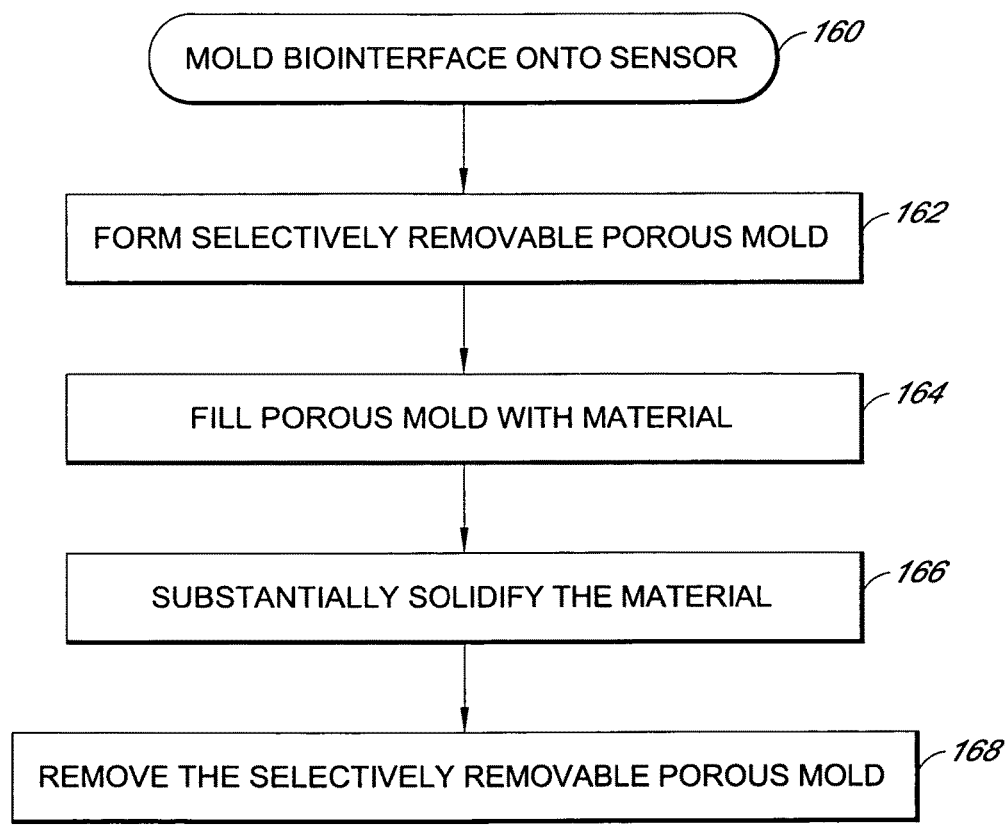
FIG. 6 is a flow chart that illustrates the process of forming a biointerface-coated sensor in an alternative embodiment.

FIG. 6 is a flow chart that illustrates the process 160 of forming a biointerface-coated sensor in an alternative embodiment. In this embodiment, the interconnected cavities and solid portion(s) of the biointerface membrane are amorphous in configuration, such as illustrated in FIGS. 4A and 4B, for example.

At block 162, a selectively removable porogen (e.g., porous mold) is formed by spraying, coating, rolling, or otherwise forming selectively removable particles, for example, sugar crystals, onto the surface of the sensor. Additional examples of materials suitable as selectively removable mold material include thermoplastic polymers such as waxes, paraffin, polyethylene, nylon, polycarbonate, or polystyrene in naturally available particles or processed into specific sizes, shapes, molded forms, spheres or fibers, salt or other particles which cannot be made to inherently stick together coated with sugar, and certain drug crystals such as gentamycin, tetracycline, or cephalosporins. In general, any dissolvable, burnable, meltable, or otherwise removable particle which can be made to stick together could be used. Preferably, the particles have shapes and sizes substantially corresponding to the desired cavity dimensions, such as described in more detail above. In some embodiments, the particles are made to adhere to the sensor by environmental conditions, for example, humidity can be used to cause sugar to adhere to the sensor.

In some embodiments, the particles are made to coalesce to provide the desired interconnectivity between the cavities. In an exemplary porous silicone embodiment, sugar crystals are exposed to a humid environment sufficient to cause coalescence of the sugar crystals. In some alternative embodiments, other molds may be used in the place of the particles described above, for example, coral, self-assembly beads, etched and broken silicon pieces, glass frit pieces, and the like.

At block 164, a material (e.g., a moldable or conformable material) is filled or coated into the interconnected cavities of the mold using methods common in the art of polymer processing, for example, injecting, pressing, vacuuming, vapor depositing, extruding, pouring, and the like. Examples of materials suitable for the resulting porous device include polymers, metals, metal alloys, ceramics, biological derivatives, and combinations thereof, in solid or fiber form. In an exemplary porous silicone embodiment, silicone is pressed into the interconnected cavities of the mold.

At block 166, the material is substantially cured or solidified to form the solid portion(s) of the biointerface membrane. Solidification of the material can be accelerated by supplying dry air (which may be heated) to the material, for example. Additionally, freezing, freeze drying or vacuum desiccation, with or without added heat, may also be utilized to cause the material to solidify. In some circumstances, a skin or any excess material can be removed (e.g., shaved, etched, or the like) after curing. In the exemplary porous silicone embodiment, an outer skin of silicone is removed to expose the interconnected cavities at an outer surface.

At block 168, the selectively removable porogen (e.g., porous mold) is dissolved, melted, etched, or otherwise removed, leaving interconnecting cavities within the solid portion. Preferably, the selectively removable porogen is readily removable without significantly altering the final product (or product material). This removal may be by dissolution by some solvent that does not significantly dissolve the final product material. Alternatively, the mold material may be melted (or burned) out of the final product material if the melting point (or burning point) of the mold material is below that of the final product material. In the exemplary porous silicone embodiment, water is used to dissolve the sugar crystals.

Figure 7:
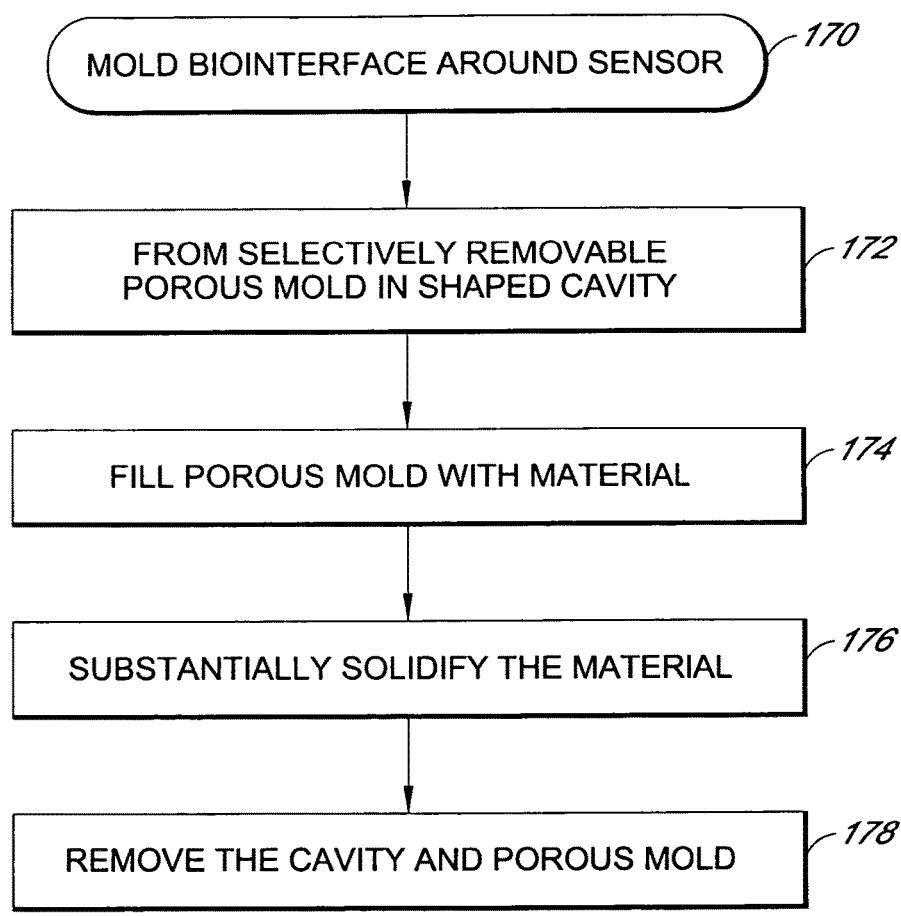
FIG. 7 is a flow chart that illustrates the process of forming a biointerface-coated sensor in another alternative embodiment.

FIG. 7 is a flow chart that illustrates the process 170 of forming a biointerface-coated small structured sensor in another alternative embodiment. In this embodiment, the interconnected cavities and solid portion(s) of the biointerface membrane are amorphous in configuration, such as illustrated in FIGS. 4A and 4B, for example, and the solid portion is molded around the sensor.

At block 172, a selectively removable porogen is formed by filling a shaped cavity with selectively removable particles, for example, sugar crystals, wherein the sensor is located within the shaped cavity, and wherein the selectively removable particles substantially surround the sensor. Additional examples of materials suitable as selectively removable mold material are described with reference to block 162, above. In some embodiments, the shaped cavity mold is formed from a selectively removable material (e.g., sacrificial cavity mold) similar the selectively removable particles described above. One such example includes a tube formed from a dissolvable polymer. Alternatively, the shaped cavity can be a non-selectively removable material, and instead, a sacrificial layer of selectively removable material is formed directly onto the cavity walls, enabling the removal of the biointerface membrane after dissolution of the sacrificial layer.

Preferably the shape of the cavity mold substantially corresponds to the desired final shape of the biointerface membrane. In one exemplary embodiment, the cavity mold is substantially cylindrical, for example using a syringe or cannula as the cavity mold.

In some embodiments, the particles are made to coalesce to provide the desired interconnectivity between the cavities. In an exemplary porous silicone embodiment, sugar crystals are exposed to humidity or spray of water sufficient to cause coalescence of the sugar crystals. In some alternative embodiments, other molds may be used in the place of the particles described above, for example, coral, self-assembly beads, etched and broken silicon pieces, glass frit pieces, and the like.

At block 174, a material (e.g., a moldable or conformable material) is filled into the interconnected cavities of the mold using methods common in the art of polymer processing, for example, injecting, pressing, vacuuming, vapor depositing, pouring, and the like. Examples of materials suitable for the resulting porous device are described in more detail with reference to block 164, above. In an exemplary porous silicone embodiment, silicone is pressed into the interconnected cavities of the mold.

At block 176, the material is substantially cured or solidified to form the solid portion(s) of the biointerface membrane. Solidification of the material can be accelerated as described in more detail with reference to block 166, above.

At block 178, the selectively removable porogen is dissolved, melted, etched, or otherwise removed, leaving interconnecting cavities within the solid portion surrounding the sensor. In some embodiments, wherein a sacrificial layer is formed as described above, the sacrificial layer can be removed before, during, or after the removal of the selectively removable porogen. In some embodiments, the final product is removed from the cavity mold before, during, or after the removal of the selectively removable porogen.

Preferably, the selectively removable porogen is readily removable without significantly altering the final product (or product material). This removal may be by dissolution by some solvent that does not significantly dissolve the final product material. Alternatively, the mold material may be melted (or burned) out of the final product material if the melting point (or burning point) of the mold material is below that of the final product material. In one exemplary embodiment, a sacrificial tube forms the mold cavity; wherein the sacrificial tube is removed prior to, during, or after dissolution of the selectively removable porogen. One skilled in the art can appreciate a variety of modifications or combinations of the above described removal step without departing from the spirit of the invention.

Figure 8:
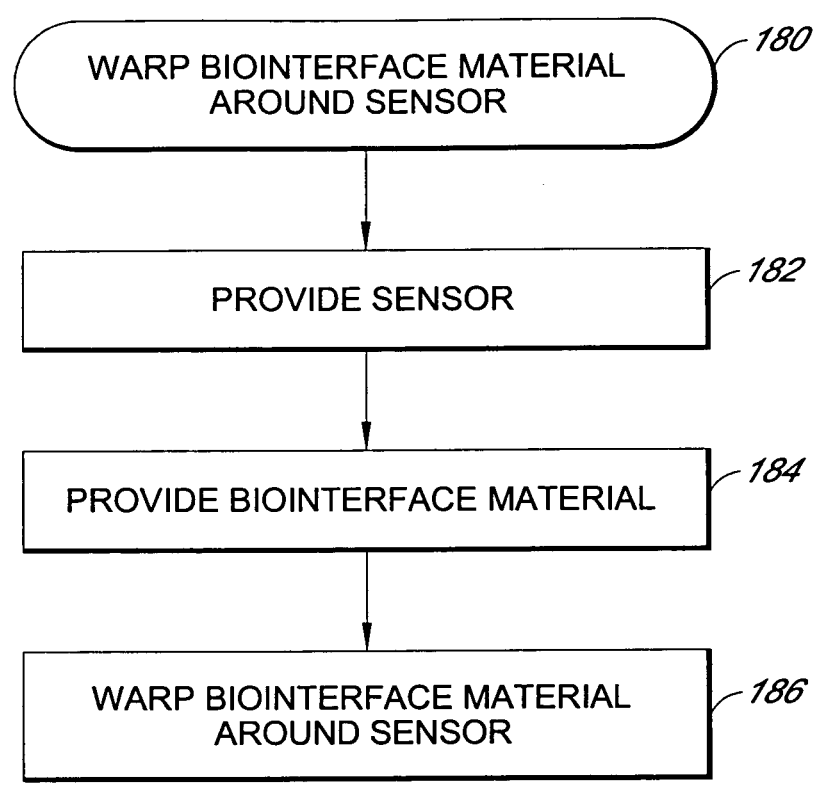
FIG. 8 is a flow chart that illustrates the process of forming a biointerface-wrapped sensor in one embodiment.

FIG. 8 is a flow chart that illustrates the process 180 of forming a biointerface-wrapped sensor in one embodiment. In this embodiment, the interconnected cavities and solid portion(s) of the biointerface membrane can be fibrous or amorphous in configuration. In fact, substantially any biointerface membrane with an architecture as described in more detail above, which is formed in substantially any manner, can be used with this embodiment.

At block 182, a sensor is manufactured and provided, wherein the sensor is formed with a small structure as defined herein.

At block 184, a biointerface membrane with an architecture as described herein is manufactured in substantially any desired manner, wherein the biointerface membrane is formed substantially as a sheet or tube of membrane. Biointerface membranes suitable for wrapping around the sensor and providing the desired host interface are described in more detail above (see section entitled, "Architecture of the First Domain.")

At block 186, the biointerface membrane is wrapped around the sensor manually, or using an automated device, as can be appreciated by one skilled in the art. Namely, the biointerface membrane is wrapped such that it substantially surrounds the sensor, or the sensing mechanism of the sensor (e.g., the electroactive surfaces or sensing membrane). The number of wraps can be from less than 1 to about 100, preferably 1, 1½, 2, 2½, 3, 3½, 4, 5, 6, 7, 8, 9, 10, or more. The number of wraps depends on the architecture of the sheet of biointerface membrane, and the desired architecture of the biointerface surrounding the sensor.

In some embodiments, the circumference (or a portion thereof (e.g., an edge)) of the biointerface membrane with an architecture as described herein can be adhered or otherwise attached or sealed to form a substantially consistent outer surface (of the biointerface membrane). In an aspect of this embodiment, the biointerface membrane is wrapped around the sensor one time, wherein the "wrap" includes a tubular biointerface membrane configured to slide over the sensor (or sensing mechanism), for example, be stretching the tubular biointerface membrane and inserting the sensor therein.

Figure 9:
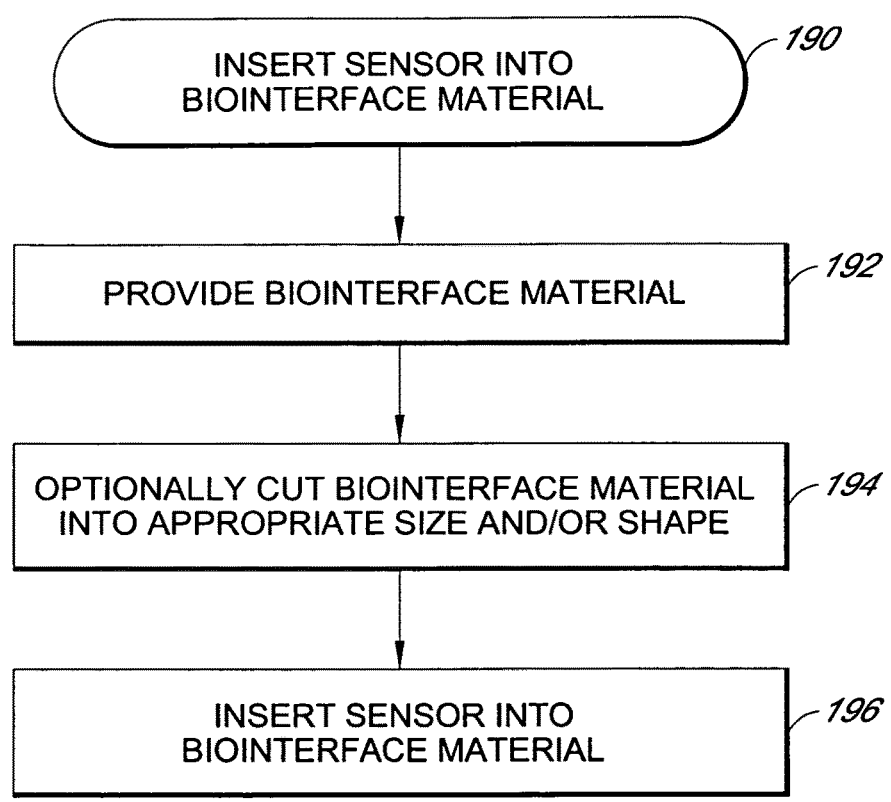
FIG. 9 is a flow chart that illustrates the process of forming a sensing biointerface in one embodiment.

FIG. 9 is a flow chart that illustrates the process 190 of forming a sensing biointerface in one embodiment. In this embodiment, the sensor is inserted into the biointerface membrane so that it is encompassed therein.

At block 192, a biointerface membrane is manufactured in substantially any desired manner. Biointerface membranes suitable for the sensing biointerface are described in more detail above (see for example, section entitled, "Architecture of the First Domain"). In some embodiments, the biointerface membrane is molded into the desired final shape to surround the sensor and implant into a host. Alternatively, the biointerface membrane can be provided as a sheet of bulk material.

At block 194, a particularly shaped or sized biointerface membrane can be (optionally) cut. Namely, in embodiments wherein the biointerface membrane is provided in bulk, e.g., as a sheet of material, the desire shape or size can be cut there from. In these embodiments, bulk biointerface membrane sheet is preferably of the appropriate thickness for the desired final product. In one exemplary embodiment, the biointerface membrane (bulk sheet) is compressed, for example between two substantially rigid structures, and the final size/shape biointerface membrane cut there from, after which the biointerface membrane is released. While not wishing to be bound by theory, it is believed that by compressing the biointerface membrane during cutting, a more precise shape can be achieved. It is noted that biointerface membranes can have sufficient elasticity, such that the thickness is returned after release from compression, as is appreciated by one skilled in the art.

At block 196, a sensor is inserted into the biointerface membrane. Preferably, the sensor is inserted into the membrane such that the sensing mechanism contacts at least one or more of the interconnected cavities so that the host analyte can be measured. Alternatively, the biointerface can be formed from a material that allows the flux of the analyte there through. In some embodiments, the sensor is inserted with the aid of a needle. Alternatively, the sensor is formed with appropriate sharpness and rigidity to enable insertion through the biointerface membrane.

In some embodiments, an anchoring mechanism, such as a barb, is provided on the sensor, in order to anchor the sensor within the biointerface membrane (and/or host tissue). A variety of additional or alternative aspects can be provided to implement the biointerface membrane surrounded sensors of the preferred embodiments.

A porous membrane material applied to the sensor can act as a spacer between the sensor and the surrounding tissue at the site of sensor insertion, in either the short-term or long-term sensors. For example, a spacer from 60-300 microns thick can be created of porous silicone having pore sizes of 0.6 microns and greater (e.g., up to about 1,000 microns or more). When inserted into the tissues, the adipose cells come to rest against the outermost aspects of the porous membrane, rather than against the surface of the sensor (FIG. 1C), allowing open space for transport of water-soluble molecules such as oxygen and glucose.

Porous membrane material can be manufactured and applied to a sensor using any advantageous method known to one skilled in the art. As discussed elsewhere, porous membranes can be manufactured from a variety of useful materials known in the art, depending upon the desired membrane parameters.

Figure 10A:
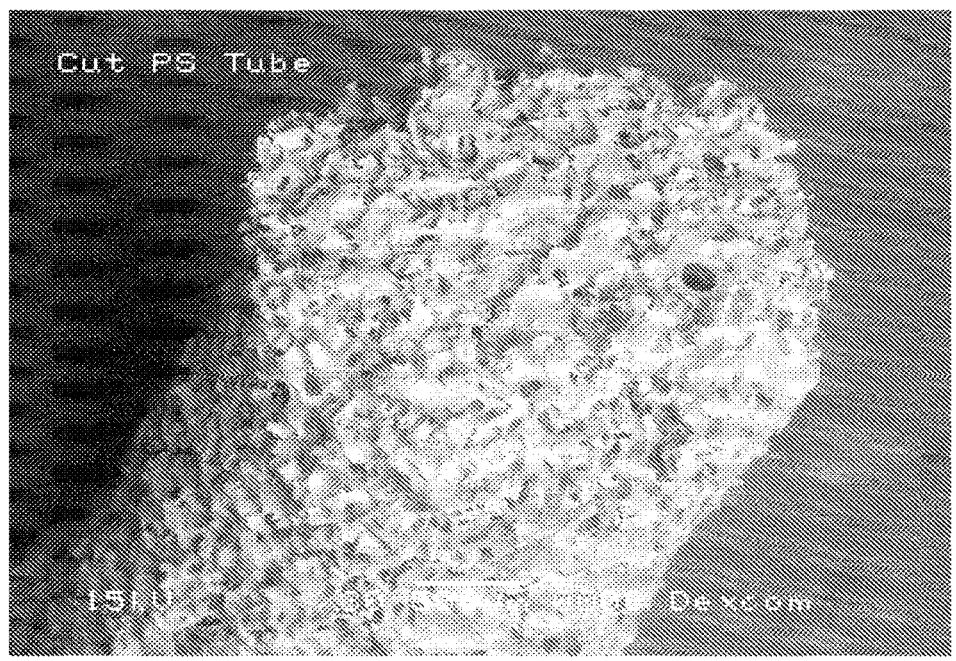
FIG. 10A is a scanning electron micrograph showing a cross-sectional view of a cut porous silicone tube. The scale line equals 500 μm.

FIG. 10A is a scanning electron micrograph showing a cross-section of an exemplary porous silicone tube that does not contain a sensor. Note the open porous structure of cavities and channels within the solidified silicone. Porous silicone can be manufactured and applied to the sensor by a variety of means. The material in FIG. 10A, for example, was formed by sieving sugar to give crystals having a size and shape approximate to that of the desired pore size. The sugar was humidified and then compressed into a mold. The mold was then baked, to harden the sugar within the mold. Silicone was forced into the mold and then cured. After the silicone was cured, the mold was removed and the sugar dissolved away. A sensor could subsequently be inserted into the porous silicone tube.

Figure 10B:
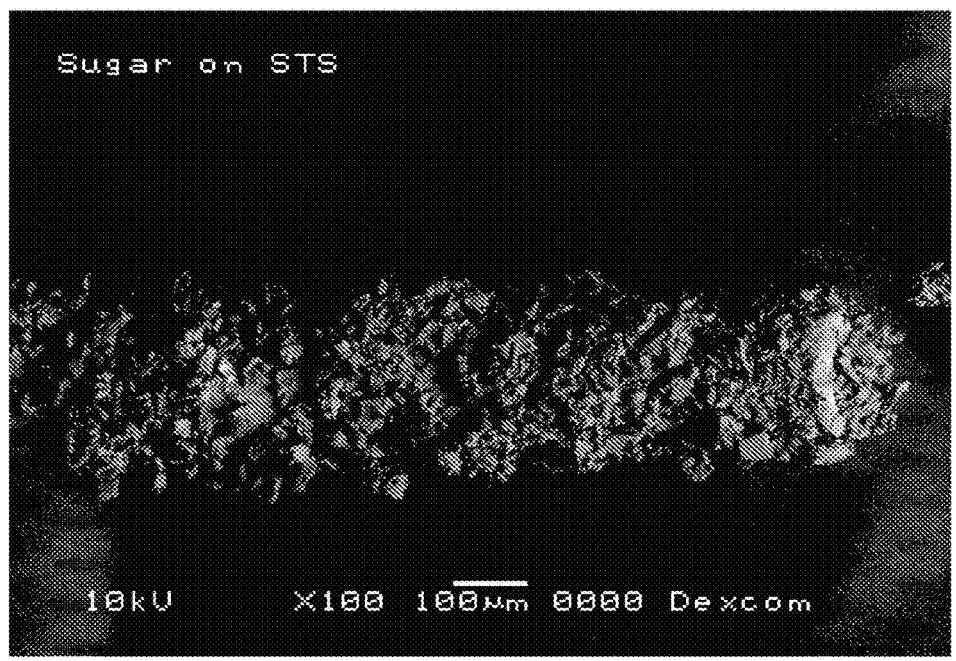
FIG. 10B is a scanning electron micrograph of a sugar mold formed on a sensor, prior to silicone application. The scale line equals 100 μm.

FIG. 10B is a scanning electron micrograph of sugar molded onto a sensor. In this example, a sugar mold was formed directly on the sensor. Note the clumps of sugar crystals attached to the surface of the sensor. In this example, the sensor was placed into the mold, which was then filled with humidified sugar crystals. The mold containing the sensor and sugar was baked to solidify the sugar on the surface of the sensor. The sensor, with sugar crystals attached, was removed from the mold, in order to prepare the electron micrograph. In some embodiments, the sensor can be rolled in the humidified sugar, to attach a layer of sugar to the sensor surface, and then baked to solidify the sugar. In some embodiments, the sugarcoated sensor may be rolled in humidified sugar additional times to form a thicker sugar mold (e.g., two or more layers) around the sensor. In some embodiments, silicone is pumped or injected into the solidified sugar and cured. After curing, the sugar is removed, such as by washing, to give a porous silicone covered sensor.

In an alternative embodiment, porous silicone is pre-formed as a sheet or plug and then applied to the sensor. For example, a sugar mold lacking a sensor therein is formed using the usual means. As previously described, silicone is injected into the mold and then cured. After the mold material is removed from the cured silicone, the sensor is inserted into the plug, thereby creating a sensor having a porous silicone biointerface membrane.

Alternatively, a thin sheet of porous silicone is manufactured and then wrapped around the sensor. For example, a thin porous silicone sheet is manufactured by pressing a thin layer of sieved, humidified sugar into a Petri dish. The sugar is baked. Silicone is applied to the sugar mold by injection, pressing, or the like, and then cured. The sugar is removed from the porous silicone sheet, such as by washing. The manufactured porous silicone is then wrapped around the sensor to form a biointerface membrane of a desired thickness.

In still another embodiment, other materials can be used to manufacture the biointerface membrane. For example, the sensor can be wrapped in a layer of ePTFE having a pore size of about 0.6 microns and above, to create a layer about 12-100 microns thick. See U.S. patent application Ser. No. 09/916,858 to Shults et al., entitled "DEVICE AND METHOD FOR DETERMINING ANALYTE LEVELS." In yet another embodiment, the spacer can be either a smooth or porous hydrogel.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

What is claimed is:

1. An analyte sensing device adapted for insertion into a host's soft tissue, comprising:
    a transcutaneous sensor comprising an in vivo portion and an ex vivo portion, wherein the sensor is configured to detect an analyte in the host, wherein the sensor comprises:
    a first electrode comprising an electroactive portion;
    a second electrode;
    a sensing membrane deposited on the electroactive portion, the sensing membrane comprising:
        a first domain comprising an enzyme configured to catalyze a reaction with the analyte; and
        a second domain comprising a carrier matrix storing a bioactive agent, wherein the second domain is configured to provide an interface with an in vivo environment, wherein the bioactive agent is configured to be released from the carrier matrix through a first release and through a second release to modify tissue response of the host, wherein the first release is configured to begin at a time associated with sensor insertion and end prior to end of sensor life, wherein the second release continues until end of sensor life, wherein the bioactive agent comprises dexamethasone; and
    a housing that houses sensor electronics configured for operable connection to sensor, wherein the sensor electronics is configured to process sensor data, and wherein the housing further comprises an adhesive pad for adhering the housing to the skin of the host.

2. The device of claim 1, wherein the second domain comprises a biointerface configured to retain body fluid in vivo.

3. The device of claim 2, wherein a concentration of an analyte in the body fluid is indicative of a concentration of the analyte in the host.

4. The device of claim 2, wherein the sensor is embedded within the biointerface.

5. The device of claim 2, wherein the biointerface comprises a plurality of pores dimensioned for fluid influx.

6. The device of claim 2, wherein the biointerface comprises a silicone polymer/hydrophilic-hydrophobic polymer blend.

7. The device of claim 2, wherein the biointerface comprises at least one of a fibrous material, a non-woven material, or a woven material.

8. The device of claim 2, wherein the biointerface comprises a mesh.

9. The device of claim 2, wherein the biointerface comprises a mechanical spacer configured to provide a protective framework around the sensor.

10. The device of claim 1, wherein the sensor is configured to measure a signal that is indicative of a concentration of the analyte within the fluid-filled pocket.

11. The device of claim 1, wherein the electronics are inductively coupled to the sensor.

12. The device of claim 1, wherein the sensor is configured to generate a signal in a picoAmp range.

13. The device of claim 1, wherein the analyte is glucose.

* * * * *

UNITED STATES PATENT AND TRADEMARK OFFICE
CERTIFICATE OF CORRECTION

PATENT NO. : 10,022,078 B2
APPLICATION NO. : 11/439630
DATED : July 17, 2018
INVENTOR(S) : James H. Brauker Page 1 of 3

It is certified that error appears in the above-identified patent and that said Letters Patent is hereby corrected as shown below:

In the Specification

Column 10 Line 5, Change "andrenostenedione;" to --androstenedione;--.

Column 10 Line 9, Change "hydroxy-cholic" to --hydroxycholic--.

Column 10 Line 21, Change "diptheria" to --diphtheria--.

Column 10 Line 28, Change "perioxidase;" to --peroxidase;--.

Column 10 Line 37, Change "sissomicin;" to --sisomicin;--.

Column 10 Line 41, Change "duodenalisa," to --duodenalis,--.

Column 10 Line 49, Change "Trepenoma pallidium," to --Treponema pallidum,--.

Column 10 Line 50, Change "stomatis" to --stomatitis--.

Column 11 Line 3-4, Change "(barbituates," to --(barbiturates,--.

Column 12 Line 55, After "not" insert --to--.

Column 13 Line 10-11, Change "2m" to --2mm--.

Column 13 Line 27, Change "et." to --et--.

Column 14 Line 59, After "as" insert --is--.

Column 15 Line 54, Change "phosporylated" to --phosphorylated--.

Signed and Sealed this
Ninth Day of October, 2018

Andrei Iancu
*Director of the United States Patent and Trademark Office*

CERTIFICATE OF CORRECTION (continued)
U.S. Pat. No. 10,022,078 B2

Column 16 Line 22, Change "days" to --days.--.

Column 18 Line 16, Change "that that" to --that--.

Column 18 Line 30, Change "can by" to --can be--.

Column 19 Line 25, Change "can by" to --can be--.

Column 19 Line 65, Change "Bellafonte," to --Bellefonte,--.

Column 23 Line 44, Change "(EDC)))" to --(EDC))--.

Column 29 Line 54, Change "York))" to --York)).--.

Column 40 Line 65-66, Change "hydroxyethylmetharcrylate, hydoxyapaptite," to --hydroxyethylmethacrylate, hydroxyapatite,--.

Column 41 Line 1, Change "nintinol," to --nitinol,--.

Column 43 Line 27, Change "polytetrafluoraethylene" to --polytetrafluoroethylene--.

Column 47 Line 41, Change "The" to --the--.

Column 48 Line 58-59, Change "hydroxyethylmetharcrylate, hydoxyapaptite," to --hydroxyethylmethacrylate, hydroxyapatite,--.

Column 48 Line 61, Change "nintinol," to --nitinol,--.

Column 52 Line 26, Change "acetometaphen," to --acetaminophen,--.

Column 52 Line 32, Change "melenamic" to --mefenamic--.

Column 52 Line 36, Change "betamethesone," to --betamethasone--.

Column 52 Line 50, Change "infiximab)," to --infliximab),--.

Column 52 Line 52-53, Change "methothrexate," to --methotrexate--.

Column 52 Line 53, Change "vincristing," to --vincristine--.

Column 52 Line 56, Change "batimstat," to --batimastat,--.

Column 52 Line 59, Change "catchins" to --catechins--.

Column 52 Line 60, Change "Tesosentan," to --Tezosentan,--.

CERTIFICATE OF CORRECTION (continued)
U.S. Pat. No. 10,022,078 B2

Column 52 Line 61, Change "Cerivasttin)," to --Cerivastatin),--.

Column 53 Line 2, Change "aminoclycosides" to --aminoglycosides--.